United States Patent
Heinelt et al.

(10) Patent No.: US 8,466,169 B2
(45) Date of Patent: Jun. 18, 2013

(54) SF₅ DERIVATIVES AS PAR1 INHIBITORS, PRODUCTION THEREOF, AND USE AS MEDICAMENTS

(75) Inventors: Uwe Heinelt, Frankfurt am Main (DE); Volkmar Wehner, Frankfurt am Main (DE); Matthias Herrmann, Frankfurt am Main (DE); Karl Schoenafinger, Alzenau (DE); Henning Steinhagen, Sulzbach (DE)

(73) Assignee: Sanofi, Paris (FR)

( * ) Notice: Subject to any disclaimer, the term of this patent is extended or adjusted under 35 U.S.C. 154(b) by 99 days.

(21) Appl. No.: 12/851,229

(22) Filed: Aug. 5, 2010

(65) Prior Publication Data
US 2011/0034461 A1 Feb. 10, 2011

Related U.S. Application Data

(63) Continuation of application No. PCT/EP2009/000408, filed on Jan. 23, 2009.

(30) Foreign Application Priority Data

Feb. 5, 2008 (EP) .................... 08290115

(51) Int. Cl.
*A61K 31/4035* (2006.01)
*C07D 209/44* (2006.01)
*C07D 471/04* (2006.01)

(52) U.S. Cl.
USPC ............ 514/300; 514/416; 546/113; 548/471

(58) Field of Classification Search
USPC .......................................... 546/113; 548/471
See application file for complete search history.

(56) References Cited

U.S. PATENT DOCUMENTS

| 6,063,847 A | 5/2000 | Chackalamannil et al. |
| 2003/0216476 A1 | 11/2003 | Kleemann |
| 2004/0152736 A1 | 8/2004 | Chackalamannil et al. |
| 2004/0242659 A1 | 12/2004 | Tasaka et al. |
| 2005/0197370 A1 | 9/2005 | Bossenmaier et al. |

FOREIGN PATENT DOCUMENTS

| CA | 2 515 715 A1 | 9/2004 |
| EP | 1 391 452 A1 | 2/2004 |
| EP | 1391451 A1 | 2/2004 |
| WO | WO03/089248 A1 | 10/2003 |
| WO | WO2005/047239 A1 | 5/2005 |
| WO | WO2005/047240 A1 | 5/2005 |
| WO | WO2006/018954 A1 | 2/2006 |
| WO | WO2006/018955 A1 | 2/2006 |
| WO | WO2006/051623 A1 | 5/2006 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Rheumatoid arthritis [online], retrieved on Jan. 2, 2013, URL; http://www.ncbi.nlm.nih.gov/pubmedhealth/PMH0001467/.*
Welch J.T. et al., "The Synthesis and Biological Activity of Pentafluorosulfanyl Analogs of Fluoxetine, Fenfluramine, and Norfenfluramine", *Bioorganic & Medicinal Chemistry* 15:6659-6666 (2007).
Extended European Search Report dated Jun. 16, 2008 from related European Application No. 08290115.8.

* cited by examiner

*Primary Examiner* — Shawquia Young
(74) *Attorney, Agent, or Firm* — Scully, Scott, Murphy & Presser, P.C.

(57) ABSTRACT

The invention relates to novel compounds of formula I

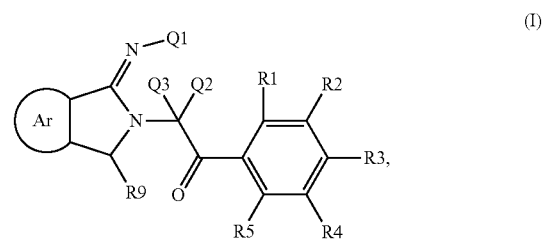

where R1, R2, R3, R4, R5, R9, Ar, Q1, Q2 and Q3 are each as defined below. The compounds of the formula I have antithrombotic activity and inhibit especially protease-activated receptor 1 (PAR1). The invention further relates to a process for preparing the compound of the formula I and to the use thereof as a medicament.

9 Claims, No Drawings

SF$_5$ DERIVATIVES AS PAR1 INHIBITORS, PRODUCTION THEREOF, AND USE AS MEDICAMENTS

FIELD OF THE INVENTION

The invention relates to novel compounds of the formula I

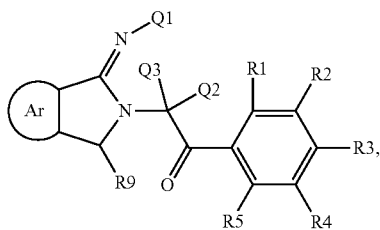

(I)

where R1, R2, R3, R4, R5, R9, Ar, Q1, Q2 and Q3 are each as defined below. The compounds of the formula I have antithrombotic activity and inhibit especially protease-activated receptor 1 (PAR1). The invention further relates to a process for preparing the compound of the formula I and to the use thereof as a medicament.

BACKGROUND OF THE INVENTION

Protease-activated receptor 1 (PAR1) is a thrombin receptor which belongs to the class of G protein-coupled receptors (GPCR). The gene for PAR1 is located on chromosome 5q13, consists of two exons and covers a region of about 27 kb. PAR1 is expressed inter alia in endothelial cells, smooth muscle cells, fibroblasts, neurons and human blood platelets. On blood platelets, PAR1 is an important receptor of signal transmission and is involved in initiating the aggregation of blood platelets. Activation of the PARs takes place by proteolytic elimination of part of the N terminus of the PARs, thus exposing a new N-terminal sequence which then activates the receptor (Pharmacol Rev 54:203-217, 2002).

The coagulation of blood is a process for controlling blood flow which is essential for the survival of mammals. The process of coagulation and the subsequent breakup of the clot after wound healing has taken place starts after damage to a vessel and can be divided into four phases:
1. The phase of vascular constriction: the blood loss into the damaged area is reduced thereby.
2. The next phase is that of platelet adhesion to the exposed collagen in the subendothelium. This primary adhesion to the matrix activates the platelets, which then secrete various activators which lead to enhancement of the activation. These activators additionally stimulate further recruitment of new platelets to the site of vessel damage and promote platelet aggregation. The platelets aggregate at the site of vessel wall damage and form a still loose platelet plug. Activation of platelets further leads to presentation of phosphatidylserine and phosphatidylinositol along the cell membrane surfaces. Exposure of these phospholipids is essential for binding and activating the multienzyme complexes of the coagulation cascade.
3. The initially still loose platelet aggregate is crosslinked by fibrin. If the thrombus comprises only platelets and fibrin, it is a white thrombus. If red blood corpuscles are additionally present, it is a red thrombus.
4. After wound healing, the thrombus is broken up by the action of the protein plasmin.

Two alternative pathways lead to the formation of a fibrin clot, the intrinsic and the extrinsic pathway. These pathways are initiated by different mechanisms, but in a later phase they converge to a common pathway of the coagulation cascade. Formation of a red thrombus or a clot at the base of a vessel wall abnormality without wound is the result of the intrinsic pathway. Fibrin clot formation as response to tissue damage or injury is the result of the extrinsic pathway. Both pathways include a relatively large number of proteins which are known as coagulation factors.

The intrinsic pathway requires coagulation factors VIII, IX, X, XI and XII and prekallikrein, high molecular weight kininogen, calcium ions and phospholipids from platelets. Each of these proteins leads to activation of factor X.

The intrinsic pathway is initiated when prekallikrein, high molecular weight kininogen, factors XI and XII bind to a negatively charged surface. This moment is referred to as the contact phase. Exposure to a vessel wall collagen is the primary stimulus of the contact phase. The result of the contact phase processes is conversion of prekallikrein into kallekrein, which in turn activates factor XII. Factor XIIa hydrolyzes further prekallekrein to kallekrein, so that the result is activation. As the activation of factor XII increases there is activation of factor XI which leads to release of bradykinin, a vasodilator. The initial phase of vasoconstriction is terminated thereby. Bradykinin is produced from the high molecular weight kininogen. In the presence of Ca$^{2+}$ ions, factor XIa activates factor IX. Factor IX is a proenzyme which contains vitamin K-dependent, c-carboxyglutamate (GLA) residues. The serine protease activity becomes evident after Ca$^{2+}$ ions have bound to these GLA residues. Several of the serine proteases in the blood coagulation cascade (factors II, VII, IX and X) contain such vitamin K-dependent GLA residues. Factor IXa cleaves factor X and leads to activation to factor Xa. The precondition for the formation of factor IXa is the formation of a protease complex of Ca$^{2+}$ ions and factors VIIIa, IXa and X on the surface of activated platelets. One of the reactions of activated platelets is the presentation of phosphatidylserine and phosphatidylinositol along the surfaces. Formation of the protease complex is made possible by exposure of these phospholipids. In this process, factor VIII acts as a receptor for factors IXa and X. Factor VIII therefore represents a cofactor in the coagulation cascade. Activation of factor VIII with formation of factor VIIIa, the actual receptor, requires only a minimal amount of thrombin. As the concentration of thrombin increases, factor VIIIa is finally cleaved further, and inactivated, by thrombin. This dual activity of thrombin in relation to factor VIII leads to the protease complex formation being self-limiting and thus the blood coagulation being localized.

PAR1 and PAR4 play a central role in the activation of human blood platelets by thrombin; activation of these receptors leads to morphological changes in blood platelets, release of ADP and aggregation of the blood platelets (Nature 413: 26-27, 2001).

PAR1 inhibitors are described for example in European patent applications EP1391451 and EP1391452, U.S. Pat. No. 6,063,847 and US 2004/0152736, and international application WO 03/089428.

DESCRIPTION OF THE INVENTION

The compounds of the formula I are notable for increased metabolic stability compared to compounds from WO2006 051623 or EP1391451, as can be shown, for example, by in vitro tests in liver microsomes. The metabolic stability can be determined, for example, by incubating the compound of the formula I in liver microsomes in the presence or absence of NADPH.

The compounds of the formula I are therefore suitable for prophylactic and therapeutic use in humans suffering from disorders associated with thromboses, embolisms, hypercoagulability or fibrotic alterations. Examples of such disorders are thrombosis, deep vein thrombosis, pulmonary embolisms, cerebral infarction, myocardial infarction, high blood pressure, inflammatory disorders, rheumatism, asthma, glomerulonephritis or osteoporosis. The compounds of the formula I can be employed for secondary prevention and are suitable both for acute and for long-term therapy. The compounds of the formula I can also be employed in combination with active ingredients which act by antithrombotic principles different from PAR1.

1) The invention therefore relates to a compound of the formula I

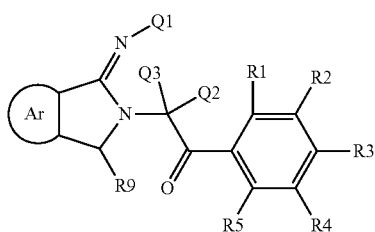

(I)

and/or any stereoisomeric or tautomeric forms of the compound of the formula I and/or mixtures of these forms in any ratio, and/or a physiologically compatible salt of the compound of the formula I, where Ar is a fused benzene, pyridine, pyrimidine, pyridazine or pyrazine ring, where the fused ring is unsubstituted or mono-, di-, tri- or tetrasubstituted independently by —($C_1$-$C_6$)-alkyl, —($C_3$-$C_6$)-cycloalkyl, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —$SO_2CF_3$, —$SF_5$, —Si[($C_1$-$C_4$)-alkyl]$_3$, —($C_1$-$C_6$)-alkylene-O—($C_1$-$C_6$)-alkyl, —($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_4$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where all or some of the hydrogen atoms in alkyl, alkylene or cycloalkyl may be replaced by fluorine, Q1 is a hydrogen atom, —($C_1$-$C_6$)-alkyl, —($C_3$-$C_6$)-cycloalkyl, —OH, —O—($C_1$-$C_6$)-alkyl or —O—($C_3$-$C_6$)-cycloalkyl, where alkyl and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine, Q2 and Q3 are the same or different and each independently a hydrogen atom, —($C_1$-$C_6$)-alkyl or —($C_3$-$C_6$)-cycloalkyl, where all or some of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where all or some of the hydrogen atoms in alkyl, alkylene or cycloalkyl may be replaced by fluorine, or R11 and R12 in the "N(R11)-R12" and "N(R11)-C(O)—R12" fragments are a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine, R1, R2, R3, R4 and R5 are the same or different and are each independently a hydrogen atom, —($C_1$-$C_6$)-alkyl, —($C_3$-$C_6$)-cycloalkyl, OH, —CN, —$NO_2$, —O—($C_1$-$C_6$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —O—($C_1$-$C_6$)-alkylene-O—($C_1$-$C_6$)-alkyl, —($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —Si[($C_1$-$C_4$)-alkyl]$_3$ or —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where all or some of the hydrogen atoms in alkyl, alkylene or cycloalkyl may be replaced by fluorine, with the proviso that at least one R1, R2, R3, R4 or R5 is —$SF_5$, R9 is a hydrogen atom, —($C_1$-$C_6$)-alkyl, —($C_3$-$C_6$)-cycloalkyl, —($C_0$-$C_4$)-alkylene-($C_6$-$C_{14}$)-aryl where aryl is unsubstituted or mono-, di- or trisubstituted independently by —O—($C_1$-$C_6$)-alkyl,
—($C_1$-$C_4$)-alkyl, OH, —($C_3$-$C_6$)-cycloalkyl or —O—($C_3$-$C_6$)-cycloalkyl,
—($C_0$-$C_4$)-alkylene-($C_4$-$C_{15}$)-Het where Het is unsubstituted or mono-, di-, tri-, tetra- or pentasubstituted independently by halogen,
—($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine,
R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or
R21 and R22 in the "N(R21)-R22" and "N(R21)-C(O)—R22" fragments are a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

2) Preference is given to a compound of the formula I where Ar is a fused benzene or pyridine ring,
where the fused ring is unsubstituted or mono-, di-, tri- or tetrasubstituted independently by —($C_1$-$C_6$)-alkyl, —($C_3$-$C_6$)-cycloalkyl, OH, —CN, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, $SO_2CH_3$, —($C_0$-$C_4$)-alkylene-N(R11)-R12, —($C_0$-$C_4$)-alkylene-N(R11)-C(O)—R12, halogen, —$SO_2CF_3$, —Si[($C_1$-$C_4$)-alkyl]$_3$, —($C_1$-$C_6$)-alkylene-O—($C_1$-$C_6$)-alkyl, —($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by
halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
—($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where all or some of the hydrogen atoms in alkyl, alkylene or cycloalkyl may be replaced by fluorine,
Q1, Q2 and Q3 are the same or different and each independently a hydrogen atom, —($C_1$-$C_6$)-alkyl or —($C_3$-$C_6$)-cycloalkyl, where all or some of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl, —$SO_2CH_3$ or —$SO_2CF_3$,
where all or some of the hydrogen atoms in alkyl, alkylene or cycloalkyl may be replaced by fluorine, or
R11 and R12 in the "N(R11)-R12" and "N(R11)-C(O)—R12" fragments are a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine,
R1, R2, R3, R4 and R5 are the same or different and are each independently a hydrogen atom, —($C_1$-$C_6$)-alkyl, —($C_3$-$C_6$)-cycloalkyl, OH, —CN, —$NO_2$, —O—($C_1$-$C_6$)-alkyl, —O—($C_3$-$C_6$)-cycloalkyl,
—($C_0$-$C_4$)-alkylene-(CO)—N(R21)-R22, —$SO_2CH_3$, —$SO_2CF_3$,
—($C_0$-$C_4$)-alkylene-C(O)—O—R21, halogen, —$SF_5$,
—($C_0$-$C_4$)-alkylene-C(O)—R21, —($C_0$-$C_4$)-alkylene-N(R21)-R22,
—($C_0$-$C_4$)-alkylene-N(R21)-C(O)—R22, —($C_1$-$C_6$)-alkylene-O—($C_1$-$C_6$)-alkyl, —O—($C_1$-$C_6$)-alkylene-O—($C_1$-$C_6$)-alkyl, —($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —Si[($C_1$-$C_4$)-alkyl]$_3$ or —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
—($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
where all or some of the hydrogen atoms in alkyl, alkylene or cycloalkyl may be replaced by fluorine,
with the proviso that at least one R1, R2, R3, R4 or R5 is —$SF_5$,
R9 is a hydrogen atom, —($C_1$-$C_6$)-alkyl, —($C_3$-$C_6$)-cycloalkyl, —($C_0$-$C_4$)-alkylene-($C_6$-$C_{14}$)-aryl where aryl is unsubstituted or mono-, di- or trisubstituted independently by —O—($C_1$-$C_6$)-alkyl,
—($C_1$-$C_4$)-alkyl, OH, —($C_3$-$C_6$)-cycloalkyl or —O—($C_3$-$C_6$)-cycloalkyl, —($C_0$-$C_4$)-alkylene-($C_4$-$C_{15}$)-Het where Het is unsubstituted or mono-, di-, tri-, tetra- or pentasubstituted independently by halogen,
—($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine,
R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments are a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

3) Particular preference is given to a compound of the formula I where

Ar is a fused benzene or pyridine ring,
  where the fused ring is unsubstituted or mono-, di-, tri- or tetrasubstituted independently by —($C_1$-$C_6$)-alkyl, —($C_3$-$C_6$)-cycloalkyl, OH, —CN, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, $SO_2CH_3$, —($C_0$-$C_4$)-alkylene-N(R11)-R12, —($C_0$-$C_4$)-alkylene-N(R11)-C(O)—R12, halogen, —Si[($C_1$-$C_4$)-alkyl]$_3$, —($C_1$-$C_6$)-alkylene-O—($C_1$-$C_6$)-alkyl or —O—($C_1$-$C_6$)-alkylene-O—($C_1$-$C_6$)-alkyl,
  where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by
  halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
  —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or
  —O—($C_3$-$C_6$)-cycloalkyl,
  where all or some of the hydrogen atoms in alkyl, alkylene or cycloalkyl may be replaced by fluorine, Q1, Q2 and Q3 are the same or different and each independently a hydrogen atom, —($C_1$-$C_6$)-alkyl or —($C_3$-$C_6$)-cycloalkyl, where all or some of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl or —$SO_2CH_3$,
  where all or some of the hydrogen atoms in alkyl, alkylene or cycloalkyl may be replaced by fluorine, or R11 and R12 in the "N(R11)-R12" and "N(R11)-C(O)—R12" fragments are a 5- to 8-membered ring which is selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine, R1, R2, R3, R4 and R5 are the same or different and are each independently a hydrogen atom, —($C_1$-$C_6$)-alkyl, —($C_3$-$C_6$)-cycloalkyl, OH, —CN, —$NO_2$, —O—($C_1$-$C_6$)-alkyl, —O—($C_3$-$C_6$)-cycloalkyl,
  —($C_0$-$C_4$)-alkylene-(CO)—N(R21)-R22, —$SO_2CH_3$,
  —($C_0$-$C_4$)-alkylene-C(O)—O—R21, halogen, —$SF_5$,
  —($C_0$-$C_4$)-alkylene-C(O)—R21, —($C_0$-$C_4$)-alkylene-N(R21)-R22,
  —($C_0$-$C_4$)-alkylene-N(R21)-C(O)—R22, —($C_1$-$C_6$)-alkylene-O—($C_1$-$C_6$)-alkyl, —O—($C_1$-$C_6$)-alkylene-O—($C_1$-$C_6$)-alkyl, —Si[($C_1$-$C_4$)-alkyl]$_3$ or —($C_4$-$C_{15}$)-Het,
  where alkyl, alkylene and cycloalkyl are each unsubstituted or mono-, di- or trisubstituted independently by —($C_1$-$C_4$)-alkyl, OH, —($C_3$-$C_6$)-cycloalkyl, —O—($C_1$-$C_6$)-alkyl or —O—($C_3$-$C_6$)-cycloalkyl, where all or some of the hydrogen atoms in alkyl or cycloalkyl may be replaced by fluorine,
  with the proviso that one R1, R2, R3, R4 or R5 is —$SF_5$, R9 is a hydrogen atom, —($C_1$-$C_6$)-alkyl or —($C_3$-$C_6$)-cycloalkyl, where all or some of the hydrogen atoms in alkyl or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
  where some or all of the hydrogen atoms in alkyl, alkylene or cycloalkyl may be replaced by fluorine, or R21 and R22 in the "N(R21)-R22" and "N(R21)-C(O)—R22" fragments are a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

4) The invention further relates to a compound of the formula I where

Ar is a fused benzene ring,
  where the fused ring is unsubstituted or mono- or disubstituted independently by —O—($C_1$-$C_6$)-alkyl, —C(O)—N(R11)-R12 or halogen, Q1, Q2 and Q3 are the same and are each a hydrogen atom, R11 and R12 are each independently a hydrogen atom or —($C_1$-$C_6$)-alkyl, R1, R2, R3, R4 and R5 are the same or different and are each independently a hydrogen atom, —($C_1$-$C_6$)-alkyl, —O—($C_1$-$C_6$)-alkyl, halogen, —$SF_5$, —($C_0$-$C_4$)-alkylene-N(R21)-R22, —O—($C_1$-$C_6$)-alkylene-O—($C_1$-$C_6$)-alkyl or —($C_0$-$C_4$)-alkylene-N(R21)-C(O)—R22,
  with the proviso that one R1, R2, R3, R4 or R5 is —$SF_5$, R9 is a hydrogen atom, R21 and R22 are each independently a hydrogen atom, —($C_1$-$C_6$)-alkyl, —($C_3$-$C_6$)-cycloalkyl, $CF_3$ or —$SO_2CH_3$,
  where some or all of the hydrogen atoms in alkyl, alkylene or cycloalkyl may be replaced by fluorine, or R21 and R22 in the "N(R21)-R22" fragment are a ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl.

5) Exceptionally preferred are compounds of the formula I including the following compounds:

2-(1-imino-1,3-dihydroisoindol-2-yl)-1-(3-pentafluorosulfanylphenyl)-ethanone as the hydrobromide, N-methyl-2-[2-(3-dimethylamino-5-pentafluorosulfanylphenyl)-2-oxoethyl]-6-ethoxy-3-imino-2,3-dihydro-1H-isoindole-5-carboxamide, N-methyl-6-ethoxy-3-imino-2-[2-(3-methylamino-5-pentafluorosulfanylphenyl)-2-oxoethyl]-2,3-dihydro-1H-isoindole-5-carboxamide, N-methyl-6-ethoxy-3-imino-2-{2-[3-pentafluorosulfanyl-5-(2,2,2-trifluoroacetylamino)phenyl]-2-oxoethyl}-2,3-dihydro-1H-isoindole-5-carboxamide, N-methyl-6-ethoxy-2-(2-{3-[ethyl-(2,2,2-trifluoroacetyl)amino]-5-pentafluorosulfanylphenyl}-2-oxoethyl)-3-imino-2,3-dihydro-1H-isoindole-5-carboxamide, N-methyl-6-ethoxy-2-[2-(3-ethylamino-5-pentafluorosulfanylphenyl)-2-oxoethyl]-3-imino-2,3-dihydro-1H-isoindole-5-carboxamide as the hydrochloride, N-methyl-2-[2-(3-amino-5-pentafluorosulfanylphenyl)-2-oxoethyl]-6-ethoxy-3-imino-2,3-dihydro-1H-isoindole-5-carboxamide, N-methyl-2-[2-(3-acetylamino-5-pentafluorosulfanylphenyl)-2-oxoethyl)-6-ethoxy-3-imino-2,3-dihydro-1H-isoindole-5-carboxamide, 2-(5,6-diethoxy-7-fluoro-1-imino-1,3-dihydroisoindol-2-yl)-1-[3-methylamino-5-(pentamethylsulfanyl)phenyl]ethanone, N-methyl-6-ethoxy-3-imino-2-{2-[3-dimethanesulfonylamino-5-(pentafluorosulfanyl)phenyl]-2-oxoethyl)-2,3-dihydro-1H-isoindole-5-carboxamide, N-methyl-2-{2-[3-(acetylmethylamino)-5-(pentafluorosulfanyl)phenyl]-2-oxoethyl}-6-ethoxy-3-imino-2,3-dihydro-1H-isoindole-5-carboxamide, N-[3-[2-(5,6-diethoxy-7-fluoro-1-imino-1,3-dihydroisoindol-2-yl)acetyl]-5-(pentafluorosulfanyl)phenyl]-N-methylacetamide, N-[3-[2-(5,6-diethoxy-7-fluoro-1-imino-1,3-dihydroisoindol-2-yl)acetyl]-5-(pentafluorosulfanyl)phenyl]isobutyramide, N-[3-[2-(5,6-diethoxy-7-fluoro-1-imino-1,3-dihydroisoindol-2-yl)acetyl]-5-(pentafluorosulfanyl)phenyl]acetamide as the hydrobromide, N-[5-[2-(5,6-diethoxy-7-fluoro-1-imino-1,3-dihydroisoindol-2-yl)acetyl]-4-methyl-2-(pentafluorosulfanyl)phenyl]acetamide, 1-[5-amino-2-methyl-4-(pentafluorosulfanyl)phenyl]-2-(5,6-diethoxy-7-fluoro-1-imino-1,3-dihydroisoindol-2-yl)ethanone, N-{3-[2-(5,6-diethoxy-7-fluoro-1-imino-1,3-dihydroisoindol-2-yl)acetyl]-5-(pentafluorosulfanylphenyl}-3,3-dimethylbutyramide, 1-{3-[2-(5,6-diethoxy-7-fluoro-1-imino-1,3-dihydroisoindol-2-yl)acetyl]-5-pentafluorosulfanylphenyl}pyrrolidine-2,5-dione, 1-[2-amino-4-(pentafluorosulfanyl)phenyl]-2-(5,6-diethoxy-7-fluoro-1-imino-1,3-dihydroisoindol-2-yl)ethanone, 1-[2-amino-5-bromo-4-(pentafluorosulfanyl)phenyl]-2-(5,6-diethoxy-7-fluoro-1-imino-1,3-dihydroisoindol-2-yl)ethanone, 2-(5,6-diethoxy-7-fluoro-1-imino-1,3-dihydroisoindol-2-yl)-1-[3-methoxy-5-(pentafluorosulfanyl)phenyl]ethanone, N-[3-[2-(5,6-diethoxy-7-fluoro-1-imino-1,3-dihydroisoindol-2-yl)acetyl]-5-(pentafluorosulfanyl)phenyl]cyclobutanecarboxamide as the hydrochloride, N-[3-[2-(5,6-diethoxy-7-fluoro-1-imino-1,3-dihydroisoindol-2-yl)acetyl]-5-(pentafluorosulfanyl)phenyl]cyclopropanecarboxamide as the hydrochloride, 2-(5,6-diethoxy-7-fluoro-1-imino-1,3-dihydroisoindol-2-yl)-1-[3-ethoxy-5-(pentafluorosulfanyl)phenyl]ethanone, N-methyl-6-ethoxy-3-imino-2-{2-[3-methoxy-5-(pentafluorosulfanyl)phenyl]-2-oxoethyl}-2,3-dihydro-1H-isoindole-5-carboxamide, 1-[3-bromo-5-(pentafluorosulfanyl)phenyl]-2-(5,6-diethoxy-7-fluoro-1-imino-1,3-dihydroisoindol-2-yl)ethanone, 1-[3-chloro-5-(pentafluorosulfanyl)phenyl]-2-(5,6-diethoxy-7-fluoro-1-imino-1,3-dihydroisoindol-2-yl)ethanone, 1-[2-bromo-4-(pentafluorosulfanyl)phenyl]-2-(5,6-diethoxy-7-fluoro-1-imino-1,3-dihydroisoindol-2-yl)ethanone, 1-[2-chloro-4-(pentafluorosulfanyl)phenyl]-2-(5,6-diethoxy-7-fluoro-1-imino-1,3-dihydroisoindol-2-yl)ethanone, 2-(5,6-diethoxy-7-fluoro-1-imino-1,3-dihydroisoindol-2-yl)-1-[3-morpholin-4-yl-5-(pentafluorosulfanyl)phenyl]ethanone or 2-(5,6-diethoxy-7-fluoro-1-imino-1,3-dihydroisoindol-2-yl)-1-[3-(2-methoxyethoxy)-5-(pentafluorosulfanyl)phenyl]ethanone as the hydrochloride.

The expression "$(C_1-C_4)$-alkyl" or "$(C_1-C_6)$-alkyl" is understood to mean hydrocarbon radicals whose carbon chain is straight or branched and contains 1 to 4 or 1 to 6 carbon atoms, for example methyl, ethyl, propyl, isopropyl, butyl, isobutyl, sec-butyl, tert-butyl, pentyl, isopentyl, neopentyl, 1-ethylpropyl, hexyl, 2,3-dimethylbutyl or neohexyl.

The expression "—$(C_0-C_4)$-alkylene" is understood to mean hydrocarbon radicals whose carbon chain is straight or branched and contains 1 to 4 carbon atoms, for example methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethylethylene, 1-methylpropylene, 2-methylpropylene. "—$C_0$-alkylene" is a covalent bond.

The expression "—O—$(C_1-C_6)$-alkyl" is understood to mean alkoxy radicals whose carbon chain is straight or branched and contains 1 to 6 carbon atoms, for example methoxy, ethoxy, propoxy, isopropoxy, butoxy, isobutoxy, tert-butoxy, 1-pentoxy, 2-pentoxy, 3-pentoxy, 1-hexoxy, 2-hexoxy or 3-hexoxy.

The expression "$(C_3-C_6)$-cycloalkyl" is understood to mean radicals such as compounds which derive from 3- to 6-membered monocycles such as cyclopropane, cyclobutane, cyclopentane or cyclohexane.

The expression "—O—$(C_3-C_6)$-cycloalkyl" is understood to mean cycloalkoxy radicals such as compounds which derive from 3- to 6-membered monocycles such as cyclopropoxy, cyclobutoxy, cyclopentoxy or cyclohexoxy.

The expression "—$(C_6-C_{14})$-aryl" is understood to mean aromatic carbon radicals having 6 to 14 carbon atoms in the ring. —$(C_6-C_{14})$-Aryl radicals are, for example, phenyl, 1-naphthyl, 2-naphthyl, anthryl or fluorenyl. Naphthyl radicals and especially phenyl radicals are preferred aryl radicals.

The expression "Ar is a fused benzene ring" is understood to mean bicyclic ring systems which, together with the dihydropyrrole ring in formula I, form a 2,3-dihydro-1H-isoindole ring which has the following structure:

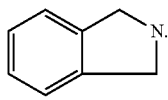

In the case that "Ar is a fused pyridine ring", this is understood to mean bicyclic ring systems which, together with the dihydropyrrole ring in formula I, form, for example, a 2,3-dihydro-1H-pyrrolo[3,4-c]pyridine ring which has the following structure:

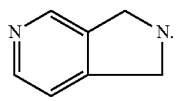

In the case that "Ar is a fused pyrimidine ring", this is understood to mean bicyclic ring systems which, together with the dihydropyrrole ring in formula I, form, for example, a 6,7-dihydro-5H-pyrrolo[3,4-d]pyrimidine ring which has the following structure:

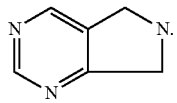

In the case that "Ar is a fused pyridazine ring", this is understood to mean bicyclic ring systems which, together with the dihydropyrrole ring in formula I, form, for example, a 6,7-dihydro-5H-pyrrolo[3,4-d]pyridazine ring which has the following structure:

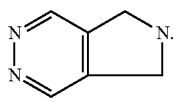

In the case that "Ar is a fused pyrazine ring", this is understood to mean bicyclic ring systems which, together with the dihydropyrrole ring in formula I, form, for example, a 6,7-dihydro-5H-pyrrolo[3,4-b]pyrazine ring which has the following structure:

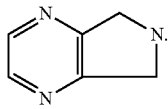

The expression "—($C_4$-$C_{15}$)-Het" is understood to mean ring systems which have 4 to 15 carbon atoms and are present in one, two or three ring systems joined to one another and which, according to ring size, may contain one, two, three or four identical or different heteroatoms from the group of oxygen, nitrogen and sulfur. Examples of these ring systems are acridinyl, azepinyl, azetidinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl radicals. The expressions "R11 and R12 in the "N(R11)-R12" and "N(R11)-C(O)—R12" fragments are a 5- to 8-membered ring which is formed together with the nitrogen atom "N" or the "N—C(O)" group to form cyclic amines, imides or lactams which contain up to 2 further heteroatoms from the group of N, O and S" and "R11 and R12 in the "N(R21)-R22" and "N(R21)-C(O)—R22" fragments are a 5- to 8-membered ring which is formed together with the nitrogen atom "N" or the "N—C(O)" group to form cyclic amines, imides or lactams which contain up to 2 further heteroatoms from the group of N, O and S" are understood to mean, for example, ring systems such as cyclic amines such as azetidinyl, pyrrolidinyl, piperidinyl, piperazinyl, azepinyl, imidazolyl, morpholinyl or thiomorpholinyl, in the case of the imides radicals such as pyrrolidine-2,5-dionyl, piperidine-2,6-dionyl, piperazine-2,6-dionyl, morpholine-3,5-dionyl, and in the case of the lactams radicals such as pyrrolidin-2-onyl, piperidin-2-onyl, piperazin-2-onyl, morpholin-3-onyl.

The rearranged expression "alkyl, alkylene or cycloalkyl in which all or some of the hydrogen atoms are replaced by fluorine" is understood to mean a partly or fully fluorinated alkyl, alkylene or cycloalkyl radical which derives, for example, for alkyl from the following radicals: —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$, —$CF_2$—$CF_2$—$CH_2F$, —$CH(CF_3)_2$, —$CH(CHF_2)_2$, —$CH(CFH_2)_2$, —$CH(CFH_2)(CHF_2)$, —$CH(CFH_2)(CF_3)$, —$CH(CFH_2)(CH_3)$, —$CH(CHF_2)(CH_3)$, —$CH(CF_3)(CH_3)$, —$CF(CF_3)_2$, —$CF(CHF_2)_2$, —$CF(CFH_2)_2$, —$CF(CFH_2)$ (CHF$_2$), —CF(CFH$_2$)(CF$_3$), —CF(CFH$_2$)(CH$_3$), —CF(CHF$_2$)(CH$_3$), —CF(CF$_3$)(CH$_3$), and also the further possible combinations for butyl, pentyl and hexyl, which, like propyl, may also be branched, for alkylene, for example, from the following radicals: —CF$_2$—, —CHF—, —CHF—CF$_2$—, —CHF—CHF—, —CHF—CH$_2$—, —CF$_2$—CF$_2$—, —CF$_2$—CH$_2$F, and also the further possible combinations for propylene, butylene, pentylene and hexylene, which may also be branched, and for cycloalkyl, for example, from the radicals

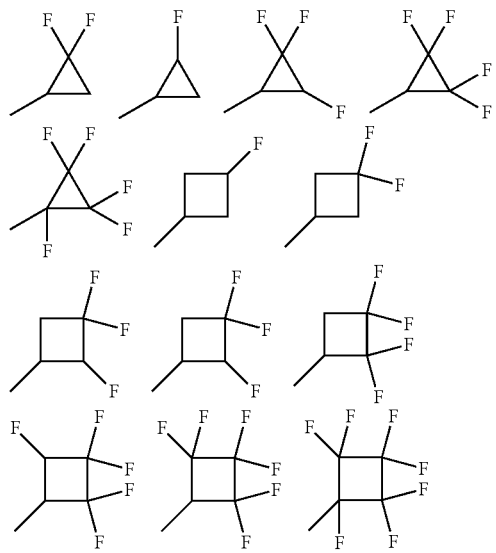

and also the analogous larger cyclopentyl and cyclohexyl rings.

The expression "halogen" is understood to mean fluorine, chlorine, bromine or iodine, preference being given to fluorine, chlorine or bromine, especially to fluorine or chlorine.

The expressions described above can also be combined as desired, as done, for example, in "—(C$_1$-C$_6$)-alkylene-O—(C$_1$-C$_6$)-alkyl".

Functional groups of the intermediates used, for example amino or carboxyl groups in the compound of the formula I, may be masked by suitable protecting groups. Suitable protecting groups for amino functions are, for example, the t-butoxycarbonyl, the benzyloxycarbonyl or the phthaloyl group, and also the trityl or tosyl protecting group. Suitable protecting groups for the carboxyl function are, for example, alkyl, aryl or arylalkyl esters. Protecting groups can be introduced and removed by techniques which are well known or are described here (see Greene, T. W., Wuts, P. G. M., *Protective Groups in Organic Synthesis* (1999), 3rd Ed., Wiley-Interscience, or Kocienski, P. J., *Protecting Groups* (2004), 3rd Ed., Thieme). The expression "protecting group" may also include corresponding polymer-bound protecting groups.

The inventive compounds can be prepared by well-known processes or by processes described here.

The invention further relates to a process for preparing the compound of the formula I and/or a stereoisomeric form of the compound of the formula I and/or a physiologically compatible salt of the compound of the formula I, which comprises a) reacting a compound of the formula II

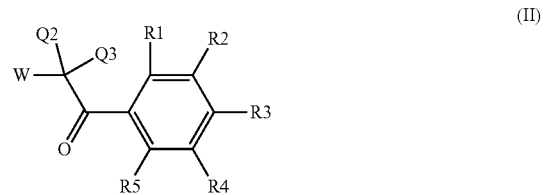

wherein R1, R2, R3, R4, R5, Q2 and Q3 are each as defined in formula I and W is chloride, bromide, mesylate or tosylate with a compound of the formula III

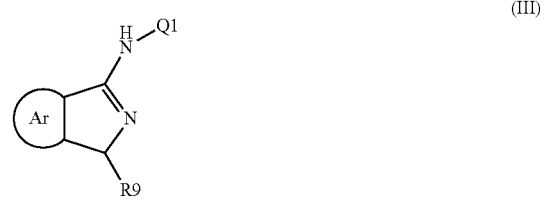

where Ar, R9 and Q1 are each as defined in formula I, with or without addition of base, in a solvent, to give a compound of the formula I, or b) reacting a compound of the formula VII

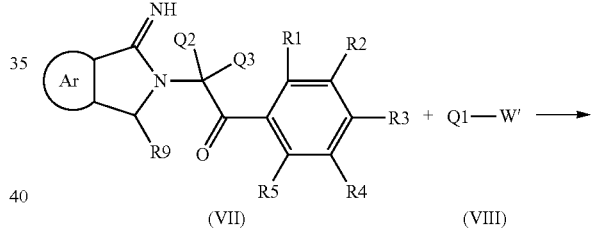

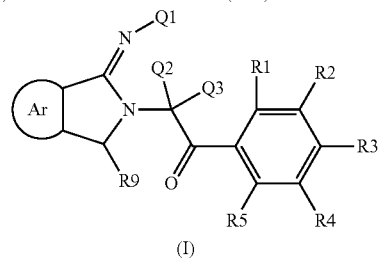

where R1, R2, R3, R4, R5, R9, Ar, Q1, Q2 and Q3 are each as defined in formula I with the compound Q1-W' where W' is chloride, bromide, mesylate, tosylate, methylsulfate or a similar good leaving group, with or without addition of base, to give a compound of the formula I, or c) either isolating the compound of the formula I prepared by process a) or b) in free form or releasing it from physiologically unacceptable salts or, in the case of presence of acidic or basic groups, converting them to physiologically acceptable salts, or d) separating a compound of the formula I prepared by process a) or b), or a suitable precursor of the formula I, which, owing to its chemical structure, occurs in enantiomeric or diastereomeric forms into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and detachment of the chiral auxiliary groups.

The invention further relates to a process for preparing the compound of the formula I according to scheme 1, where one R1, R2, F3, R4 or R5 is SF$_5$.

Scheme 1:

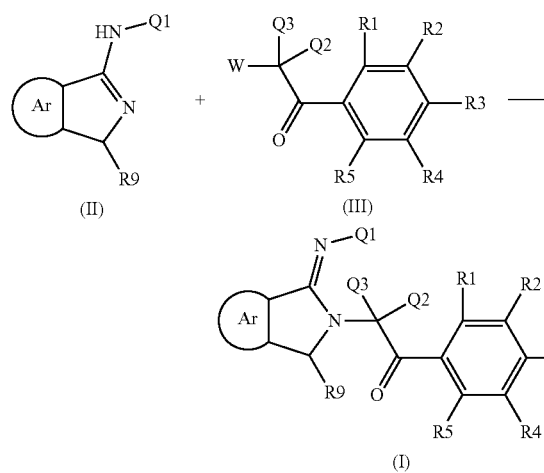

The reactants II and III, with II optionally present in the form of a salt, are converted at RT or slightly elevated temperature of 40° C. to 60° C., advantageously when II is in the form of a salt in the presence of a base, preferably Hünig's base, in a solvent, preferably dimethylformamide (DMF) or dioxane, to give the compound of the formula I. The R1, R2, R3, R4, R5, Ar and Q radicals are each as defined in formula I, W is a good leaving group such as chloride, bromide, mesylate or tosylate, preferably bromide or mesylate.

Some compounds of the formula I may also occur in isomeric forms, in which case Q1 in the following subformula of formula I may have either (E) or (Z) configuration:

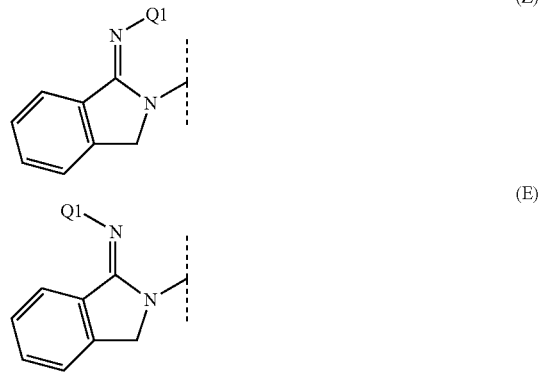

Some compounds of the formula II are commercially available or can be obtained by literature methods (WO2006 018954/5, WO2006 018954, EP 1 391 451). One route to the pentafluorosulfanyl derivatives of the formula III—compound of the formula III in which one R1, R2, R3, R4 or R5 is SF$_5$—is described hereinafter.

In general, acetyl bromides (W=Br) of the pentafluorosulfanyl derivatives of the IIIa type in which one R1, R2, R3, R4 or R5 is SF$_5$ can be prepared as described in scheme 2.

Scheme 2:

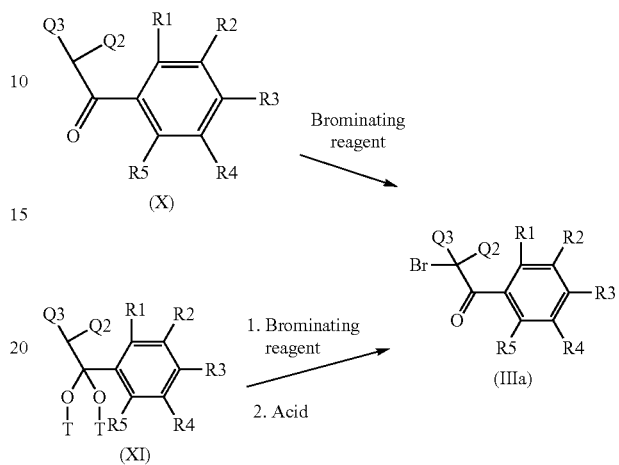

The acetophenone derivatives of the formula X, in which one R1, R2, R3, R4 or R5 is SF$_5$ can either be brominated directly, for example with Br$_2$, N-bromosuccinimide (NBS) or phenyltrimethyltribromide, preferably in glacial acetic acid, methanol or methanol/THF mixtures, to give compounds of the formula IIIa, or else the corresponding ketals XI of the acetophenone derivatives X, in which one R1, R2, R3, R4 or R5 is SF$_5$, are brominated with, for example, the above brominating reagents, preferably phenyltrimethyl tribromide. Subsequently, the compounds of the formula IIIa are obtained by cleaving the ketals in the presence of acid, for example hydrochloric acid, hydrobromic acid, sulfuric acid, trifluoroacetic acid, preferably sulfuric acid.

The ketals of the formulae XI and XI' can be obtained proceeding from the ketones of the formula X by ketalization reactions known to those skilled in the art. The reaction to give the compounds of the formula XI in methanol with methyl orthoformate is preferably performed in the presence of DL-10-camphorsulfonic acid (scheme 3).

Scheme 3:

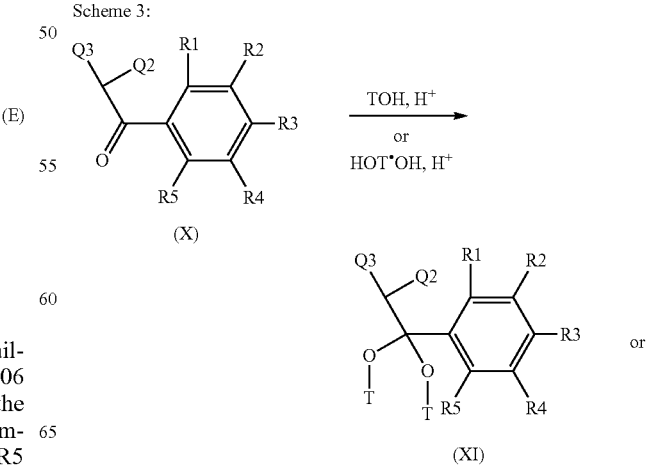

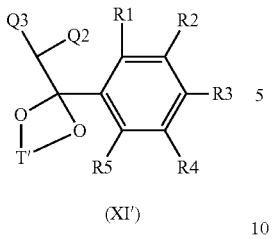

(XI')

The R1, R2, R3, R4 and R5 radicals, where one R1, R2, R3, R4 or R5 is SF$_5$, are each as defined in formula I. The T radical corresponds to a —(C$_1$-C$_4$)-alkyl group. The T' radical corresponds to ethylene, propylene or butylene, or forms, together with the —O—C—O— group, a 1,3-dioxo ring of ring size 5, 6 or 7. Ketals of this type are obtained by reaction with alkylene glycols such as ethylene glycol in the presence of acids such as sulfuric acid or para-toluenesulfonic acid and/or dehydrating agents. In the simplest case, toluene is employed in the presence of catalytic amounts of para-toluenesulfonic acid on a water separator.

Compounds of the formula X with more complex substitution, in which one R1, R2, R3, R4 or R5 is pentafluorosulfanyl (SF$_5$), and at least one further R1, R2, R3, R4 or R5 radical is as defined in formula I, can be obtained proceeding from commercially available pentafluorosulfanyl derivatives. Commercially unavailable derivatives can be obtained in analogy to known preparation processes (Tetrahedron 56 (2000) 3399; Organic Letters 4 (17) (2002) 3013; WO 2005/047240). For 1-(3-dimethylamino-5-pentafluorosulfanylphenyl)ethanone, one synthesis route is shown in scheme 4.

Scheme 4:

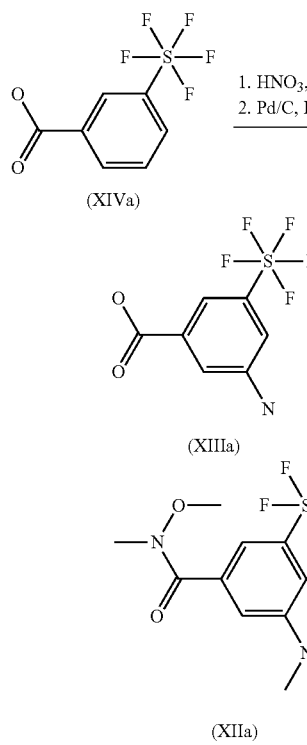

Proceeding from commercially available 3-(pentafluorosulfanyl)benzoic acid XIVa, reactions known to those skilled in the art were used first to nitrate it and then to reduce it to the amine with palladium on charcoal in the presence of hydrogen. The 3-amino-5-pentafluorosulfanylbenzoic acid XIIIa obtained was then dimethylated on the amine nitrogen under Eschweiler-Clark conditions, the carboxylic acid was converted with thionyl chloride to the acid chloride and the latter was reacted with O,N-dimethylhydroxylamine. The 3-dimethylamino-N-methoxy-N-methyl-5-pentafluorosulfanylbenzamide XIIa thus obtained was converted with methylmagnesium bromide to the corresponding pentafluorosulfanyl derivatives of the formula Xa.

Scheme 5:

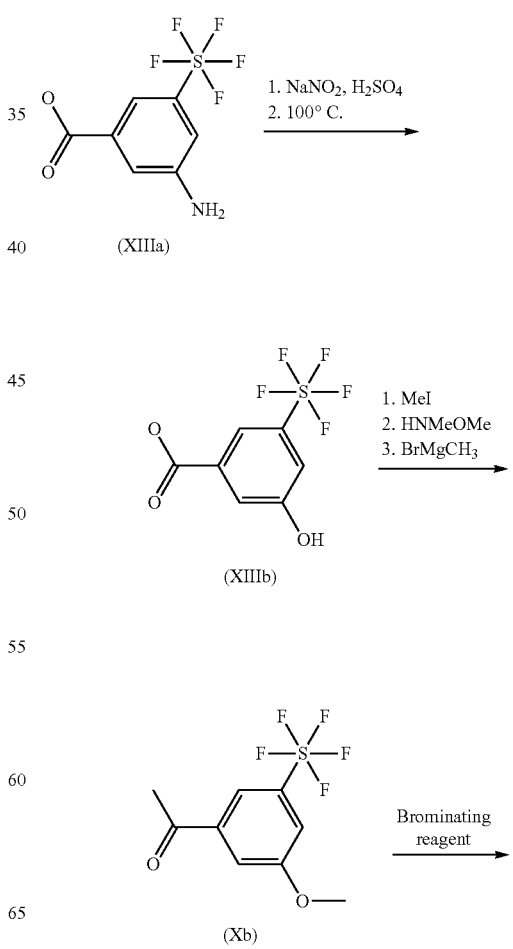

-continued

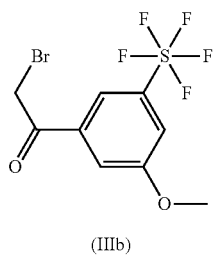

(IIIb)

Phenolic 3-(pentafluorosulfanyl)benzoic acid derivatives of the formula XIIIb can, as shown in scheme 5, be obtained proceeding from 3-amino-5-pentafluorosulfanylbenzoic acid XIIIa by diazotization and hydrolysis. Subsequent methylation, formation of the Weinreb amide and reaction with methylmagnesium bromide affords the phenol ether Xb which can be brominated according to scheme 2 to the acyl bromide IIIb.

A compound of the formula I prepared according to scheme 1, or a suitable precursor of the formula I which, owing to its chemical structure, occurs in enantiomeric forms can be separated into the pure enantiomers by salt formation with enantiomerically pure acids or bases, chromatography on chiral stationary phases or derivatization by means of chiral enantiomerically pure compounds such as amino acids, separation of the diastereomers thus obtained, and detachment of the chiral auxiliary groups (process c), or the compound of the formula I prepared according to scheme 1 can either be isolated in free form or, in the case of the presence of acidic or basic groups, converted to physiologically compatible salts (process d).

Acidic or basic products of the compound of the formula I may be in the form of their salts or in free form. Pharmacologically acceptable salts are preferred, for example alkali metal or alkaline earth metal salts or hydrochlorides, sulfates, hemisulfates, methylsulfonates, p-toluenesulfonates, all possible phosphates, and salts of amino acids, natural bases or carboxylic acids such as lactates, citrates, tartrates, acetates, adipates, fumarates, gluconates, glutamates, maleates or pamoates.

Physiologically tolerated salts are prepared from compounds of the formula I capable of salt formation, including their stereoisomeric forms, in process step c) in a manner known per se. If compounds of the formula I contain acidic functionality, stable alkali metal, alkaline earth metal or optionally substituted ammonium salts can be formed with basic reagents such as hydroxides, carbonates, bicarbonates, alkoxides, and ammonia or organic bases, for example trimethyl- or triethylamine, ethanolamine, diethanolamine or triethanolamine, trometamol or else basic amino acids, for instance lysine, ornithine or arginine. Basic groups of the compounds of the formula I form acid addition salts with acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid.

In process step d), the compound of the formula I, if it occurs as a mixture of diastereomers or enantiomers or results as mixtures thereof in the chosen synthesis, is separated into the pure stereoisomers either by chromatography on an optionally chiral support material or, if the racemic compound of the formula I is capable of salt formation, it is also possible to carry out a fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatographic methods on chiral stationary phases after appropriate derivatization known to the skilled worker. To separate enantiomers of the racemic carboxylic acids, the diastereomeric salts of differing solubility are formed with an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I which contain a basic group such an amino group, with optically active acids such as (+)-camphor-10-sulfonic acid, D- and L-tartaric acid, D- and L-lactic acid, and (+) and (−)-mandelic acid, into the pure enantiomers. It is also possible to convert chiral compounds containing alcohol or amine functions with appropriately activated or, where appropriate, N-protected enantiopure amino acids into the corresponding esters or amides, or conversely chiral carboxylic acids with carboxy-protected enantiopure amino acids into the amides or with enantiopure hydroxycarboxylic acids such as lactic acid into the corresponding chiral esters. The chirality of the amino acid or alcohol residue which has been introduced in enantiopure form can then be utilized to separate the isomers by carrying out a separation of the diastereomers which are now available by crystallization or chromatography on suitable stationary phases, and then eliminating the included chiral moiety again by suitable methods.

A further possibility for some of the compounds of the formula I is to prepare the framework structures using diastereomerically or enantiomerically pure starting materials. It is thus possible also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of the separations can likewise be achieved by proceeding in two or more stages.

The invention also relates to medicaments characterized by an effective content of at least one compound of the formula I and/or a physiologically tolerated salt of the compound of the formula I and/or an optionally stereoisomeric form of the compound of the formula I, together with a pharmaceutically suitable and physiologically compatible carrier, additive and/or other active ingredients and excipients.

Owing to the pharmacological properties, the compounds of the invention are suitable for example for prophylaxis, secondary prevention and therapy of all those disorders which can be treated by inhibition of the protease-activated receptor 1 (PAR1). Thus, the compounds of the invention are suitable both for a prophylactic and a therapeutic use on humans. They are suitable both for acute treatment and for long-term therapy. The compounds of the formula I can be employed in patients suffering from impairments of well being or diseases associated with thromboses, embolisms, hypercoagulability, fibrotic changes or inflammatory disorders.

These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. The compounds of the formula I can further be employed in all procedures leading to contact of blood with foreign surfaces, such as for dialysis patients and patients with indwelling catheters. Compounds of the formula I can be employed in order to reduce the risk of thrombosis following surgical procedures such as knee and hip joint operations.

Compounds of the formula I are suitable for the treatment of patients with disseminated intravascular coagulation, sepsis and other intravascular events associated with inflammation. The compounds of the formula I are further suitable for the prophylaxis and treatment of patients with atherosclerosis, diabetes and metabolic syndrome and the sequelae thereof. Impairments of the hemostatic system (for example fibrin deposits) have been implicated in mechanisms leading to tumor growth and tumor metastasis, and in inflammatory and degenerative articular disorders such as rheumatoid arthritis and arthrosis. Compounds of the formula I are suitable for retarding or preventing such processes.

Further indications for the use of the compounds of the formula I are fibrotic changes in the lung such as chronic obstructive pulmonary disease, adult respiratory distress syndrome (ARDS) and in the eye such as fibrin deposits following eye operations. Compounds of the formula I are also suitable for the prevention and/or treatment of scarring.

The medicaments of the invention can be administered by oral, inhalational, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for manufacturing a medicament, which comprises making a suitable dosage form from at least one compound of the formula I with a pharmaceutically suitable and physiologically compatible carrier and, where appropriate, further suitable active ingredients, additives or excipients.

Suitable solid or pharmaceutical formulations are, for example, granules, powders, coated tablets, tablets, (micro) capsules, suppositories, syrups, solutions, suspensions, emulsions, drops or injectable solutions, and products with protracted release of active ingredient, in the production of which customary aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water, physiological saline and monohydric or polyhydric alcohols such as glycerol.

The pharmaceutical products are preferably manufactured and administered in dosage units, where each unit comprises as active ingredient a particular dose of the compound of the formula I of the invention. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 10 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

Compounds of the formula I can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics. Suitable platelet aggregation inhibitors in this connection are cyclooxygenase 1 inhibitors such as aspirin, irreversible $P2Y_{12}$ antagonists such as clopidogrel or prasugrel, reversible $P2Y_{12}$ antagonists such as cangrelor or AZD6140 and thromboxane $A_2$/prostaglandin $H_2$ antagonists such as terutroban. It has already been possible to show additive effects of PAR1 blockade in combination with $P2Y_{12}$ blockade for example (Eur. Heart J. 2007, 28, Abstract Supplement, 188).

EXAMPLES

End products were generally characterized by a chromatographic method with mass spectrometry (LCUV/ESI-MS coupling), and $^1$H NMR. The compounds are described by reporting the corresponding retention time in the ion current (LC-MS rt) and the corresponding M+H$^+$ signal in the case of positive ionization in the corresponding mass spectrum. When no M+H$^+$ mass signal could be obtained, the $^1$H NMR data were reported as an alternative. Abbreviations used are either explained or correspond to the usual conventions. Unless stated otherwise, chromatographic separations were carried out on silica gel with ethyl acetate/heptane or dichloromethane/methanol mixtures as the eluent.

Solvents were evaporated generally under reduced pressure at 35° C. to 45° C. on a rotary evaporator, which is referred to by phrases such as "freed of the solvent", "concentrated", "concentrated by rotary evaporation", "dried", "solvent removed or drawn off". Unless stated otherwise, the LCUV/MS analyses were carried out under the following conditions:
System: Agilent 1100 HPLC-System coupled to 1100 LC/MSD
Column: YMC J'sphere ODS H80 20×2.1 mm, packing material 4 μm
Eluent: ACN:H$_2$O+0.05% TFA (flow rate 1 ml/min)
Gradient: 4:96 (0 min)→95:5 (2 min)→95:5 (2.4 min)→4:96 (2.45 min)
Ionization: ESI$^+$ Alternatively, and designated with "met. b", the following conditions were selected:
System: Agilent 1200 HPLC-System coupled to 6120 LC/MS
Column: Luna C18, 10×2.0 mm, packing material 3 μm
Eluent: ACN:H$_2$O+0.05% TFA (flow rate 1.1 ml/min)
Gradient: 7:93 (0 min)→95:5 (1 min)→95:5 (1.45 min)→7:93 (1.5 min)
Ionization: ESI$^+$ Preparative HPLC on reversed-phase (RP) silica gel was carried out by the following methods:
Method A, standard method when no other is mentioned in the text Column: Merck (Darmstadt) Purosphere® RP18 25×250 mm, 10 μm
Eluent: ACN:H$_2$O+0.05% TFA (flow rate 25 ml/min)
Gradient: 10:90 (0 min)→90:10 (40 min)
Method B
Column: Merck (Darmstadt) Purosphere® RP18 25×250 mm, 10 μm
Eluent: ACN:H$_2$O+0.05% TFA (flow rate 25 ml/min)
Gradient: 0:100 (0 min)→0:100 (5 min)→20:80 (20 min)
In examples 22d) and 23 c), method C was used:
Method C
Column: Agilent Prep-C18, 30×250 mm, 10 μm
Eluent: ACN:H$_2$O+0.05% TFA (flow rate 75 ml/min)
Gradient: 10:90 (0 min)→90:10 (12.5 min)→90:10 (15 min) →10:90 (15.5 min)→10:90 (17.5 min)

The reactions took place in standard reaction apparatus such as single-neck or multineck flasks, which, unless stated otherwise, according to the need, had a capacity of 5 ml to 2000 ml and, as required, were equipped with a septum, stopper, condenser, stirrer or other equipment. Unless mentioned otherwise, all reactions took place under argon as protective gas and were stirred with magnetic stirrers.

Microwave reactions were carried out in the Emrys Optimizer from Personal Chemistry in vessels of capacity from 0.5 to 10 ml according to the need.

Abbreviations used:
abs. absolute
ACN acetonitrile
Boc butoxycarbonyl
DCM dichloromethane
DIPEA N,N-diisopropylethylamine (Hünig's base)
DME dimethoxyethane
DMF dimethylformamide
DMSO dimethyl sulfoxide
h hour(s)
EA ethyl acetate
LC-MS rt retention time of the compound in the ion current
LCUV/MS ultraviolet liquid chromatography/mass spectrometry
min minute(s)
MtB ether tert-butyl methyl ether
MeOH methanol
RF reflux
RT room temperature (20° C. to 25° C.)
TFA trifluoroacetic acid
THF tetrahydrofuran

Example 1

2-(1-Imino-1,3-dihydroisoindol-2-yl)-1-(3-pentafluorosulfanylphenyl)ethanone as the hydrobromide 1a)
2-Bromo-1-(3-pentafluorosulfanylphenyl)ethanone 3-Pentafluorosulfanylacetophenone (400 mg) was initially charged in glacial acetic acid (10 ml), and bromine (91 μl, dissolved in 1 ml of glacial acetic acid) was slowly added dropwise. After stirring at RT for 4 hours, the mixture was left to stand overnight and then freed of the solvent. The residue was twice taken up with toluene and dried. The resulting crude product was purified by means of preparative HPLC. The product-containing fractions were combined, freed of the acetonitrile and freeze-dried. 252 mg of the desired compound were obtained.

LC-MS rt: 1.69 min [M+H]$^+$: 324.9

1b) 3H-Isoindol-1-ylamine as the hydrobromide

Ammonia (250 ml) was condensed into a flask, and α-bromo-o-toluntrile (20 g) dissolved in THF (100 ml) was slowly added dropwise at −78° C. over 1.5 h while stirring. After stirring for one hour, the cooling bath was removed and the mixture was left to stand overnight, such that most of the ammonia could evaporate. The residue was admixed with water, and the resulting mixture was reduced under reduced pressure and admixed with ethyl acetate. The ethyl acetate phase was removed and the residue was extracted again with ethyl acetate. The combined ethyl acetate phases were washed three times with water and the aqueous phases were combined with the aqueous residue. The aqueous phase was reduced by half under reduced pressure and then freeze-dried. 19.9 g of the title compound were obtained.

LC-MS rt: 0.33 min [M+H]$^+$: 133.1

1c) 2-(1-Imino-1,3-dihydroisoindol-2-yl)-1-(3-pentafluorosulfanylphenyl)ethanone as the hydrobromide 3H-Isoindol-1-ylamine as the hydrobromide (800 mg) was dissolved in a little water, admixed with solid sodium hydroxide pellets and extracted repeatedly with ethyl acetate. The combined ethyl acetate phases were dried over magnesium sulfate, filtered and concentrated. A portion of the resulting free base (30 mg) was dissolved in absolute THF (5 ml), and 2-bromo-1-(3-pentafluorosulfanylphenyl)ethanone (73 mg), dissolved in absolute THF (1 ml), was added dropwise while stirring. The mixture was stirred at RT for a further 6 h and then placed in a refrigerator over the weekend. The precipitate formed was filtered off with suction and dissolved in a water/acetonitrile mixture, and the solution was freeze-dried. 58 mg of the title compound were obtained.

LC-MS rt: 1.21 min [M+H]$^+$: 377.0

Example 2

N-Methyl-2-[2-(3-dimethylamino-5-pentafluorosulfanylphenyl)-2-oxoethyl]-6-ethoxy-3-imino-2,3-dihydro-1H-isoindole-5-carboxamide as the trifluoroacetic acid salt

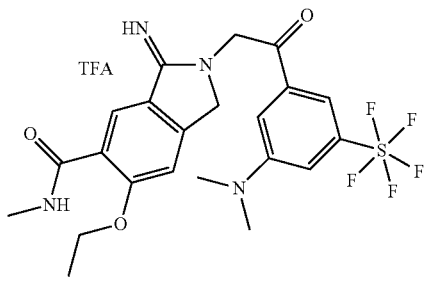 [SMILES: CCOc1cc2c(cc1C(=O)NC)C(=N)N(CC(=O)c1cc(N(C)C)cc(S(F)(F)(F)(F)F)c1)C2]

2a) 3-Amino-5-pentafluorosulfanylbenzoic acid

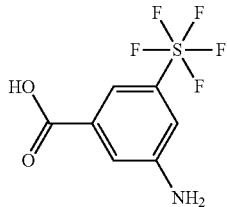

3-Pentafluorosulfanylbenzoic acid (3.0 g) was dissolved in fuming nitric acid (20 ml) and stirred at RT with exclusion of moisture. Then concentrated sulfuric acid (1.5 ml) was added and the mixture was stirred at 75° C. After stirring at 75° C. for 6 h, the mixture was left to stand overnight, then further sulfuric acid (1.5 ml) was added and the mixture was heated to 75° C. for 8 h while stirring. After being left to stand overnight, the mixture was added to ice-water and stirred for 2 h. The crystallization which set in was completed in a refrigerator overnight. Then the precipitate was filtered off with suction and dried under high vacuum. 2.7 g of 3-pentafluorosulfanyl-5-nitrobenzoic acid were obtained. A further 530 mg were obtained from the mother liquor after extracting three times with methylene chloride, drying the combined methylene chloride phases over magnesium sulfate and concentrating the solvent. Subsequently, the 3-pentafluorosulfanyl-5-nitrobenzoic acid (2.7 g) was dissolved in methanol (70 ml), Raney nickel (about 500 mg) was added and hydrogenation was effected under a hydrogen atmosphere (hydrogen balloon). After 2 h, the catalyst was filtered off and the filter-residue was washed thoroughly with methanol. The filtrate was concentrated and dried under high vacuum. 2.3 g of crude product were obtained, which were converted directly in the next stage.

LC-MS rt: 1.21 min [M+H]$^+$: 264.0

2b) 3-Dimethylamino-5-pentafluorosulfanylbenzoic acid

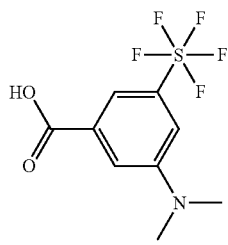 [SMILES: CN(C)c1cc(C(=O)O)cc(S(F)(F)(F)(F)F)c1]

Two microwave vessels were each charged with 3-amino-5-pentafluorosulfanylbenzoic acid (800 mg), formic acid (6 ml) and 37% formalin solution (4 ml). The two vessels were then heated to 110° C. for 30 min. After cooling, the solutions were combined and added to ice-water. After extracting three times with ethyl acetate, the combined organic phases were dried with magnesium sulfate, filtered and concentrated. 1.76 g of the title compound were obtained, which were converted directly in the next stage.

LC-MS rt: 1.48 min [M+H]$^+$: 292.0

2c) 3-Dimethylamino-N-methoxy-N-methyl-5-pentafluorosulfanylbenzamide

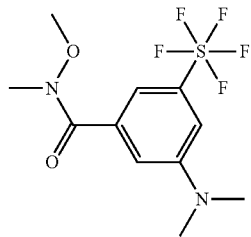

3-Dimethylamino-5-pentafluorosulfanylbenzoic acid (1.0 g) was dissolved in methylene chloride (60 ml). Thionyl chloride (5 ml) was added while stirring and the mixture was stirred at RT for 2 h. To complete the reaction, the mixture was subsequently heated to reflux for 3 h. After cooling, the solvent was drawn off, the residue was dissolved in methylene chloride (50 ml), and N,O-dimethylhydroxylamine hydrochloride (315 mg) and Hünig's base (1 ml) were added. After stirring for one hour, the solvent was drawn off, and the residue was taken up with ethyl acetate and washed 5 times with water. The organic phase was dried with magnesium sulfate, filtered and concentrated. 980 mg of the title compound were obtained, which were converted directly in the next stage.

LC-MS rt: 1.53 min [M+H]$^+$: 335.0

2d) 1-(3-Dimethylamino-5-pentafluorosulfanylphenyl)ethanone

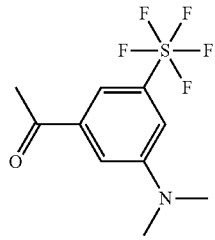 [SMILES: CC(=O)c1cc(N(C)C)cc(S(F)(F)(F)(F)F)c1]

3-Dimethylamino-N-methoxy-N-methyl-5-pentafluoro-sulfanylbenzamide (980 mg) was dissolved in abs. THF (50 ml), and methylmagnesium bromide solution (2.1 ml; 3M solution in diethyl ether) was added dropwise while stirring at 0° C. After the addition had ended, the ice bath was removed and the mixture was stirred at RT for 1 h. To complete the reaction, more methylmagnesium bromide solution (0.3 ml) was added and the mixture was stirred for a further 2 h. After storing overnight in a refrigerator, the reaction mixture was admixed with 1 N hydrochloric acid while cooling. Addition of water and ethyl acetate was followed by extraction twice more with ethyl acetate, and the combined organic phases were dried with magnesium sulfate, filtered and concentrated. The residue was purified by means of chromatography on silica gel (100/0 to 50/50 n-heptane/ethyl acetate within 30 min). The product-containing fractions were combined, the solvent was removed and the residue was dried under high vacuum. 650 mg of the title compound were obtained.

LC-MS rt: 1.69 min [M+H]$^+$: 290.0

2e) [3-(1,1-Dimethoxyethyl)-5-pentafluorosulfa-nylphenyl]dimethylamine

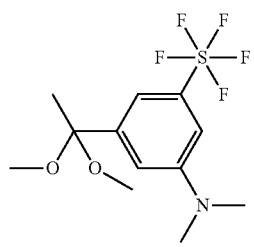

1-(3-Dimethylamino-5-pentafluorosulfanylphenyl)etha-none (650 mg) was dissolved in methanol (50 ml) and admixed while stirring with trimethyl orthoformate (715 mg) and DL-10-camphorsulfonic acid (10 mg). After stirring for 3 h, more orthoformate (200 mg) was added, and the mixture was stirred for 2 h and left to stand overnight. Then the solvent was drawn off and the residue was dried under high vacuum. 730 mg of crude product were obtained, which were converted directly in the next stage.

$^1$H NMR (400 MHz, DMSO-d$_6$) [ppm]: 7.10 (1H); 6.99 (1H); 6.93 (1H); 3.10 (6H); 2.98 (6H); 1.47 (3H)

2f) [3-(2-Bromo-1,1-dimethoxyethyl)-5-pentafluoro-sulfanylphenyl]dimethylamine and [3-(2-bromo-1,1-dimethoxyethyl)-5-pentafluorosulfanylphenyl]me-thylamine

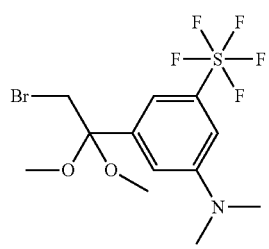

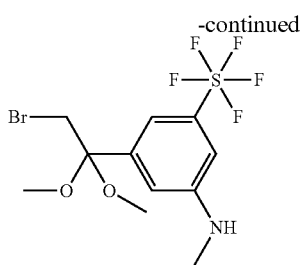

[3-(1,1-Dimethoxyethyl)-5-pentafluorosulfanylphenyl] dimethylamine (730 mg) was dissolved in a mixture of methanol (15 ml) and THF (15 ml). Phenyltrimethyl tribromide (818 mg) was added while stirring. After 3 h, the reaction was completed by adding more phenyltrimethyl tribromide (205 mg) and stirring at 60° C. for 2 h. After standing overnight, sodium thiosulfate solution, water and ethyl acetate were added. The aqueous phase was extracted three times more with ethyl acetate. The combined extracts were dried with magnesium sulfate, filtered and concentrated. The residue was purified by means of chromatography on silica gel (100/0 to 50/50 n-heptane/ethyl acetate within 30 min). The product-containing fractions were combined, the solvent was removed and the residue was dried under high vacuum. 490 mg of the dimethylamino compound and 144 mg of the monomethylamino compound were obtained.

Dimethylamine Derivative:
$^1$H NMR (500 MHz, DMSO-d$_6$) [ppm]: 7.14 (1H); 7.00 (1H); 6.95 (1H); 3.85 (2H); 3.14 (6H); 2.99 (6H)

Monomethylamine Derivative:
$^1$H NMR (500 MHz, DMSO-d$_6$) [ppm]: 7.02 (1H); 6.91 (1H); 6.84 (1H); 6.34 (1H); 3.80 (2H); 3.14 (6H); 2.71 (3H)

2g) 2-Bromo-1-(3-dimethylamino-5-pentafluorosul-fanylphenyl)ethanone

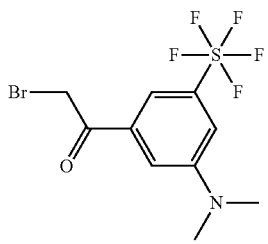 [SMILES: CN(C)c1cc(C(=O)CBr)cc(S(F)(F)(F)(F)F)c1]

[3-(2-Bromo-1,1-dimethoxyethyl)-5-pentafluorosulfa-nylphenyl]dimethylamine (230 mg) was suspended in water (2.3 ml) and then concentrated sulfuric acid (2.3 ml) was added dropwise while cooling. After stirring at RT for 2 h, the mixture was diluted with water (20 ml) and extracted three times with ethyl acetate. The combined organic phases were washed twice with saturated sodium hydrogencarbonate solution, dried over magnesium sulfate, filtered and concentrated. The residue was dissolved in acetonitrile/water, frozen and freeze-dried overnight. 170 mg of the desired compound were obtained.

LC-MS rt: 1.80 min [M+H]$^+$: 367.9

2h) N-Methyl-2-[2-(3-dimethylamino-5-pentafluoro-sulfanylphenyl)-2-oxoethyl]-6-ethoxy-3-imino-2,3-dihydro-1H-isoindole-5-carboxamide as the trifluoroacetic acid salt N-Methyl-3-amino-6-ethoxy-1H-isoindole-5-carboxamide (15 mg, purchased from Chembiotek) was dissolved in absolute DMF (2 ml), and 2-bromo-1-(3-dimethylamino-5-pentafluorosulfanylphenyl)ethanone (25 mg) dissolved in absolute THF (2.5 ml) was added dropwise while stirring. Since barely any reaction was evident after stirring at RT for 3 hours and leaving to stand overnight, the solvent was removed under reduced pressure, the residue was taken up with ethanol, and the mixture was heated to reflux. After 2 h, the reaction mixture was concentrated and purified by means of preparative HPLC. The product-containing fraction was freed of the acetonitrile and freeze-dried. 2 mg of the desired compound were obtained.

LC-MS rt: 1.24 min [M+H]$^+$: 521.0

Example 3

N-Methyl-6-ethoxy-3-imino-2-[2-(3-methylamino-5-pentafluorosulfanylphenyl)-2-oxoethyl]-2,3-dihydro-1H-isoindole-5-carboxamide as the trifluoroacetic acid salt

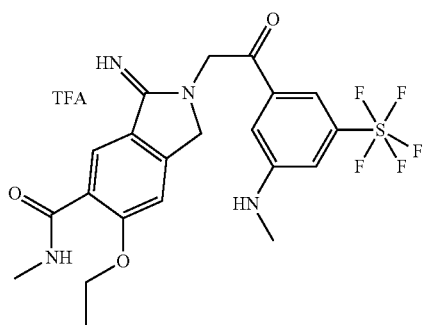 [SMILES: CCOc1cc2c(cc1C(=O)NC)C(=N)N(CC(=O)c1cc(NC)cc(S(F)(F)(F)(F)F)c1)C2]

3a) 2-Bromo-1-(3-methylamino-5-pentafluorosulfanylphenyl)ethanone

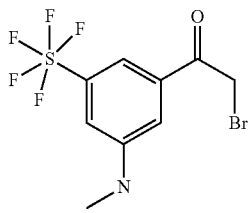

[3-(2-Bromo-1,1-dimethoxyethyl)-5-pentafluorosulfanylphenyl]methylamine (400 mg, example 2f) was suspended in water (4 ml) and then admixed with concentrated sulfuric acid (4 ml) while cooling with ice. After stirring at RT for 4 h, the mixture was poured onto ice-water and adjusted to pH 8 with saturated sodium hydrogencarbonate solution, and the aqueous phase was extracted three times with ethyl acetate. The combined extracts were dried over magnesium sulfate, filtered and concentrated. 312 mg of the desired product were obtained.

LC-MS rt: 1.67 min [M+H]$^+$: 353.9

3b) N-Methyl-6-ethoxy-3-imino-2-[2-(3-methylamino-5-pentafluorosulfanylphenyl)-2-oxoethyl]-2,3-dihydro-1H-isoindole-5-carboxamide as the trifluoroacetic acid salt N-Methyl-3-amino-6-ethoxy-1H-isoindole-5-carboxamide (40 mg, purchased from Chembiotek) was admixed with absolute DMF (8 ml), and 2-bromo-1-(3-methylamino-5-pentafluorosulfanylphenyl)ethanone (61 mg), dissolved in absolute DMF (1 ml), was added while stirring. After stirring for 1 h and leaving to stand overnight, the reaction mixture was concentrated and the residue was purified by means of preparative HPLC. The product-containing fractions were combined, freed of the acetonitrile and freeze-dried. 50 mg of the desired compound were obtained.

LC-MS rt: 1.23 min [M+H]$^+$: 507.0

Example 4

N-Methyl-6-ethoxy-3-imino-2-{2-[3-pentafluorosulfanyl-5-(2,2,2-trifluoroacetylamino)phenyl]-2-oxoethyl}-2,3-dihydro-1H-isoindole-5-carboxamide as the trifluoroacetic acid salt

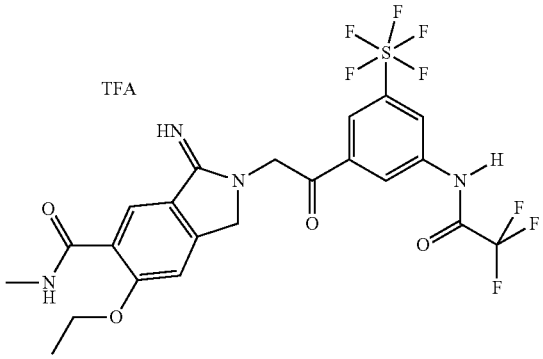 [SMILES: CCOc1cc2c(cc1C(=O)NC)C(=N)N(CC(=O)c1cc(NC(=O)C(F)(F)F)cc(S(F)(F)(F)(F)F)c1)C2]

4a) N-Methoxy-N-methyl-5-nitro-3-pentafluorosulfanylbenzamide

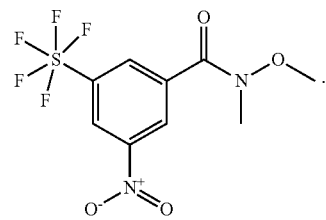 [SMILES: CON(C)C(=O)c1cc([N+](=O)[O-])cc(S(F)(F)(F)(F)F)c1]

3-Pentafluorosulfanyl-5-nitrobenzoic acid (4.0 g, example 2a) was dissolved while stirring in thionyl chloride (25 ml) and kept under reflux with exclusion of moisture for 10 h. After standing at RT overnight, excess thionyl chloride was removed under reduced pressure, and the resulting residue was dissolved in dichloromethane (50 ml) and admixed while stirring with N,O-dimethylhydroxylamine×HCl (1.25 g) and diethylisopropylamine (1.66 g). After stirring at RT for 1 h, the mixture was concentrated under reduced pressure, and the residue was dissolved in ethyl acetate and washed 5 times with water. The organic phase was dried over magnesium sulfate, filtered and concentrated. The 4.2 g of crude product obtained were used directly in the next stage.

LC-MS rt: 1.50 min [M+H]⁺: 337.0

4b) 3-Amino-N-methoxy-N-methyl-5-pentafluoro-sulfanylbenzamide

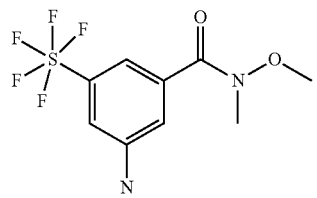 [SMILES: CON(C)C(=O)c1cc(N)cc(S(F)(F)(F)(F)F)c1]

N-Methoxy-N-methyl-5-nitro-3-pentafluorosulfanylbenzamide (4.2 g) was dissolved in methanol (120 ml), and Raney nickel (approx. 700 mg) was added. With a hydrogen balloon attached, hydrogenation was effected on a magnetic stirrer. After 5 h, the catalyst was filtered off and washed with methanol. The filtrate was concentrated under reduced pressure and the residue was purified by means of preparative chromatography. The product-containing fractions were combined, freed of the acetonitrile, basified with sodium hydrogencarbonate solution and extracted three times with ethyl acetate. The combined extracts were dried over magnesium sulfate, filtered and concentrated. 1.73 g of the desired compound were obtained.

LC-MS rt: 1.27 min [M+H]⁺: 307.0

4c) N-Methoxy-N-methyl-5-pentafluorosulfanyl-3-(2,2,2-trifluoroacetylamino)benzamide

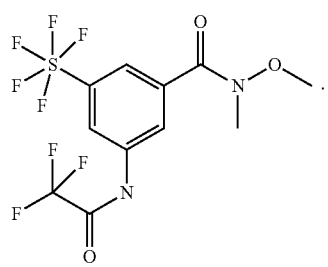 [SMILES: CON(C)C(=O)c1cc(NC(=O)C(F)(F)F)cc(S(F)(F)(F)(F)F)c1]

3-Amino-N-methoxy-N-methyl-5-pentafluorosulfanyl-benzamide (1.45 g) was dissolved in methylene chloride (15 ml), and triethylamine (0.8 ml) followed by trifluoroacetic anhydride (0.85 ml) were added with the exclusion of moisture while stirring. After stirring at RT for 3 h and standing overnight, water and saturated sodium hydrogencarbonate solution were added, the phases were separated and the methylene chloride phase was washed three times more with water, dried over magnesium sulfate, filtered and concentrated. The resulting product (1.75 g) was used without further purification in the next stage.

LC-MS rt: 1.53 min [M+H]⁺: 403.0

4d) N-(3-Acetyl-5-pentafluorosulfanylphenyl)-2,2,2-trifluoroacetamide and 1-[3-amino-5-(pentafluorosulfanyl)phenyl]ethanone trifluoroacetic acid salt

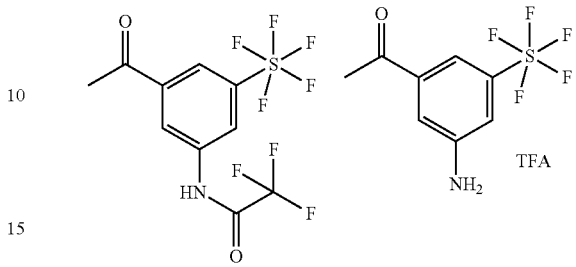

N-Methoxy-N-methyl-5-pentafluorosulfanyl-3-(2,2,2-trifluoroacetylamino)benzamide (540 mg) was dissolved in absolute THF (30 ml) and stirred at 0° C. with lithium hexamethyldisilazide (312 µl, 23% in tert-butyl methyl ether) for 30 min. At 0° C., methylmagnesium bromide (2.5 ml, 3M in diethyl ether) was then added dropwise while stirring. After stirring at RT for 6 h and leaving to stand overnight, 1 N hydrochloric acid was added dropwise while cooling, followed by water and ethyl acetate. The organic phase was removed and the water phase was extracted twice more with ethyl acetate. The combined ethyl acetate phases were dried over magnesium sulfate, filtered and concentrated. The crude product was purified by means of preparative chromatography. The product-containing fractions were combined, freed of the acetonitrile and extracted three times with ethyl acetate. The combined extracts were dried over magnesium sulfate, filtered and concentrated. 315 mg of N-(3-acetyl-5-pentafluorosulfanylphenyl)-2,2,2-trifluoroacetamide LC-MS rt: 1.60 min [M+H]⁺: 358.0 and 42 mg of 1-[3-amino-5-(pentafluorosulfanyl)phenyl]ethanone trifluoroacetic acid salt were obtained.

LC-MS rt: 1.37 min [M+H]⁺: 262.0

4e) N-[3-(2-Bromoacetyl)-5-pentafluorosulfanylphenyl]-2,2,2-trifluoroacetamide

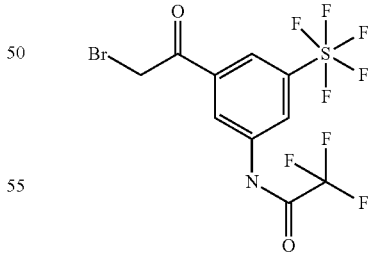

N-(3-Acetyl-5-pentafluorosulfanylphenyl)-2,2,2-trifluoroacetamide (110 mg) was dissolved in a mixture of methanol (2 ml) and THF (2 ml). Phenyltrimethyl tribromide (115 mg) was added in solid form while stirring. After stirring for 3 h and leaving to stand overnight, further phenyltrimethyl tribromide (29 mg) was added and the mixture was heated to 60° C. After 2 h, the cooled reaction mixture was added to dilute citric acid and extracted three times with ethyl acetate. After drawing off the solvent, the residue was dissolved in acetonitrile (3 ml) and admixed with 2N sulfuric acid (2 ml). After stirring for 2 h, water and ethyl acetate were added, the phases were separated and the aqueous phase was extracted three times with ethyl acetate. The combined extracts were dried over magnesium sulfate, filtered and concentrated. The residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 58 mg of the desired compound were obtained.

LC-MS rt: 1.72 min [M+H]$^+$: 436.0

4f) N-Methyl-6-ethoxy-3-imino-2-{2-[3-pentafluorosulfanyl-5-(2,2,2-trifluoroacetylamino)phenyl]-2-oxoethyl}-2,3-dihydro-1H-isoindole-5-carboxamide as the trifluoroacetic acid salt N-Methyl-3-amino-6-ethoxy-1H-isoindole-5-carboxamide (30 mg, purchased from Chembiotek) was reacted with N-[3-(2-bromoacetyl)-5-pentafluorosulfanylphenyl]-2,2,2-trifluoroacetamide (50 mg) analogously to example 3b). 31 mg of the desired compound were obtained.

LC-MS rt: 1.30 min [M+H]$^+$: 589.0

Example 5

N-Methyl-6-ethoxy-2-(2-{3-[ethyl-(2,2,2-trifluoroacetyl)amino]-5-pentafluorosulfanylphenyl}-2-oxoethyl)-3-imino-2,3-dihydro-1H-isoindole-5-carboxamide as the trifluoroacetic acid salt

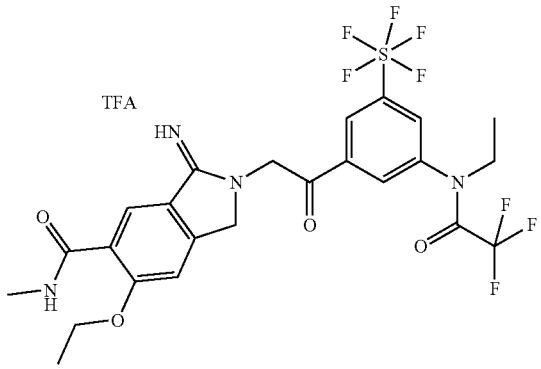 [SMILES: CCOc1cc2c(cc1C(=O)NC)C(=N)N(CC(=O)c1cc(N(CC)C(=O)C(F)(F)F)cc(S(F)(F)(F)(F)F)c1)C2]

5a) N-(3-Acetyl-5-pentafluorosulfanylphenyl)-N-ethyl-2,2,2-trifluoroacetamide

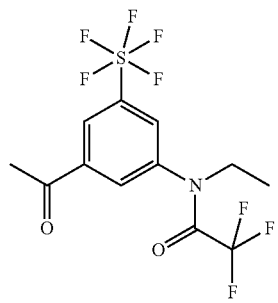 [SMILES: CCN(C(=O)C(F)(F)F)c1cc(C(C)=O)cc(S(F)(F)(F)(F)F)c1]

N-(3-Acetyl-5-pentafluorosulfanylphenyl)-2,2,2-trifluoroacetamide (100 mg, example 4d) was dissolved in absolute dimethoxyethane (5 ml) in a microwave insert and admixed with powdered potassium carbonate (40 mg). After adding iodoethane (60 µl), the mixture was heated to 100° C. in the microwave for 30 min. Subsequently, further iodomethane (60 µl) was added and the mixture was heated again to 100° C. for 30 min. This operation was repeated once more. Then the mixture was worked up by adding it to a mixture of water, ethyl acetate and 1 N HCl. Removal of the organic phase was followed by extraction three times more with ethyl acetate. The combined extracts were dried over magnesium sulfate, filtered and concentrated. The residue was purified by means of preparative HPLC. The product-containing fractions were combined, freed of the acetonitrile and extracted three times with ethyl acetate. The combined extracts were dried over magnesium sulfate, filtered and concentrated. 50 mg of the desired compound were obtained.

LC-MS rt: 1.68 min [M+H]$^+$: 386.0

5b) N-[3-(2-Bromoacetyl)-5-pentafluorosulfanylphenyl]-N-ethyl-2,2,2-trifluoroacetamide

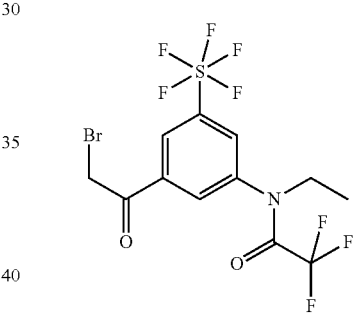

N-(3-Acetyl-5-pentafluorosulfanylphenyl)-N-ethyl-2,2,2-trifluoroacetamide (50 mg) was brominated analogously to example 4e), except that, in this case, the reaction was worked up after stirring at RT for 4 h. After purification, 40 mg of the desired product were obtained.

LC-MS rt: 1.79 min [M+H]$^+$: 464.0

5c) N-Methyl-6-ethoxy-2-(2-{3-[ethyl-(2,2,2-trifluoroacetyl)amino]-5-pentafluorosulfanylphenyl}-2-oxoethyl)-3-imino-2,3-dihydro-1H-isoindole-5-carboxamide as the trifluoroacetic acid salt N-Methyl-3-amino-6-ethoxy-1H-isoindole-5-carboxamide (18 mg, purchased from Chembiotek) was reacted with N-[3-(2-bromoacetyl)-5-pentafluorosulfanylphenyl]-N-ethyl-2,2,2-trifluoroacetamide (35 mg) analogously to example 3b). 16 mg of the desired compound were obtained.

LC-MS rt: 1.28 min [M+H]$^+$: 617.2

Example 6

N-Methyl-6-ethoxy-2-[2-(3-ethylamino-5-pentafluorosulfanylphenyl)-2-oxoethyl]-3-imino-2,3-dihydro-1H-isoindole-5-carboxamide as the hydrochloride

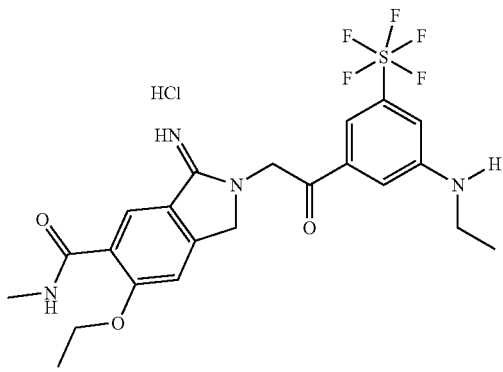 [SMILES: CCNc1cc(C(=O)CN2Cc3cc(OCC)c(C(=O)NC)cc3C2=N)cc(S(F)(F)(F)(F)F)c1 ; Cl]

N-Methyl-6-ethoxy-2-(2-{3-[ethyl-(2,2,2-trifluoroacetyl)amino]-5-pentafluorosulfanylphenyl}-2-oxoethyl)-3-imino-2,3-dihydro-1H-isoindole-5-carboxamide as the trifluoroacetic acid salt (11 mg, example 5c) was admixed with water (1.5 ml), and conc. sulfuric acid (1.5 ml) was added while stirring and cooling with ice. Subsequently, the mixture was heated to 80° C. for 5 h. After cooling, the solution was added slowly while cooling with ice and stirring to a mixture of ethyl acetate and 10N sodium hydroxide solution. The aqueous phase was extracted five times with ethyl acetate. The combined extracts were dried over magnesium sulfate, filtered and concentrated. The residue was dissolved in a mixture of water and acetonitrile. 0.1N HCl was used to adjust the pH to 2 and then the mixture was freeze-dried. 5 mg of the desired compound were obtained.

LC-MS rt: 1.29 min [M+H]⁺: 521.1

Example 7

N-Methyl-2-[2-(3-amino-5-pentafluorosulfanylphenyl)-2-oxoethyl]-6-ethoxy-3-imino-2,3-dihydro-1H-isoindole-5-carboxamide as the trifluoroacetic acid salt

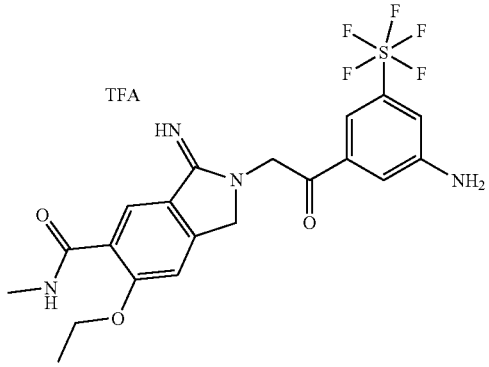 [SMILES: CCOc1cc2c(cc1C(=O)NC)C(=N)N(CC(=O)c1cc(N)cc(S(F)(F)(F)(F)F)c1)C2 ; "TFA"]

N-methyl-6-ethoxy-3-imino-2-{2-[3-pentafluorosulfanyl-5-(2,2,2-trifluoro-acetylamino)phenyl]-2-oxoethyl}-2,3-dihydro-1H-isoindole-5-carboxamide trifluoroacetic acid salt (20 mg, example 4f) was admixed with 2N sulfuric acid (2 ml) and DMF (0.75 ml) and, after adding one drop of conc. sulfuric acid, heated to 80° C. for 3 h. After cooling, the mixture was adjusted to pH 9 with saturated potassium carbonate solution and the water phase was extracted three times with ethyl acetate. The combined extracts were dried over magnesium sulfate, filtered and concentrated. The residue was purified by means of preparative HPLC. The product-containing fractions were combined, freed of the acetonitrile and freeze-dried. 3.4 mg of the desired compound were obtained.

LC-MS rt: 1.15 min [M+H]⁺: 493.0

Example 8

N-Methyl-2-[2-(3-acetylamino-5-pentafluorosulfanylphenyl)-2-oxoethyl]-6-ethoxy-3-imino-2,3-dihydro-1H-isoindole-5-carboxamide as the trifluoroacetic acid salt

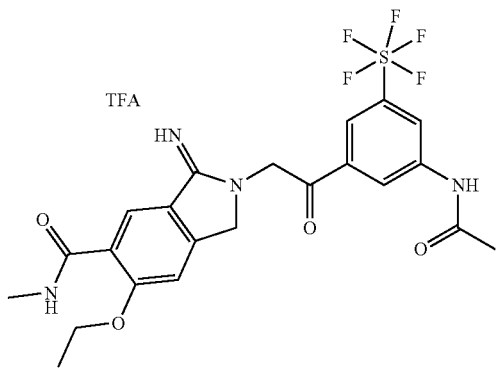 [SMILES: CCOc1cc2c(cc1C(=O)NC)C(=N)N(CC(=O)c1cc(NC(C)=O)cc(S(F)(F)(F)(F)F)c1)C2 ; "TFA"]

8a) N-[3-Acetyl-5-(pentafluorosulfanyl)phenyl]acetamide

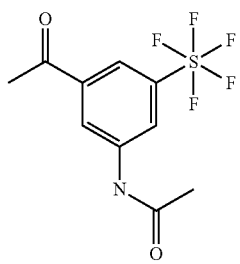 [SMILES: CC(=O)Nc1cc(C(C)=O)cc(S(F)(F)(F)(F)F)c1]

1-[3-Amino-5-(pentafluorosulfanyl)phenyl]ethanone trifluoroacetic acid salt (100 mg, example 4d) was dissolved in methylene chloride (10 ml), and triethylamine (120 μl) was added. Acetic anhydride (30 μl) was then added dropwise while stirring. After stirring for 4 h, the mixture was left to stand overnight and then further acetic anhydride (30 μl) was added. After stirring for a further 6 h, the reaction mixture was again left to stand overnight and then concentrated. The residue was taken up with ethyl acetate and water, and adjusted to pH 9 with saturated sodium hydrogencarbonate solution, and the aqueous phase was extracted twice more with ethyl acetate. The combined extracts were dried over magnesium sulfate, filtered and concentrated. 80 mg of the desired compound were obtained.

LC-MS rt: 1.34 min [M+H]$^+$: 304.0

8b) N-[3-(2-Bromoacetyl)-5-pentafluorosulfanylphenyl]acetamide

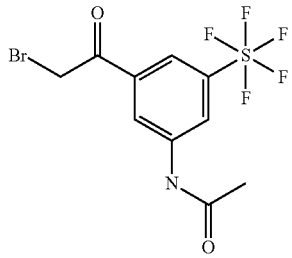

N-[3-Acetyl-5-(pentafluorosulfanyl)phenyl]acetamide (80 mg) was dissolved in a mixture of methanol (2.5 ml) and THF (2.5 ml), and phenyltrimethyl tribromide (100 mg) was added while stirring. After stirring at RT for 5 h, further phenyltrimethyl tribromide (25 mg) was added and the mixture was heated to 60° C. for 2 h. After cooling, the reaction mixture was added to 2N sulfuric acid and the aqueous phase was extracted three times with ethyl acetate. The combined extracts were dried over magnesium sulfate, filtered and concentrated. The residue was purified by means of preparative HPLC. The product-containing fractions were combined, freed of the acetonitrile, basified with sodium hydrogencarbonate and extracted three times with ethyl acetate. The combined extracts were dried over magnesium sulfate, filtered and concentrated. 24 mg of the desired compound were obtained.

LC-MS rt: 1.49 min [M+H]$^+$: 382.0

8c) N-Methyl-2-[2-(3-acetylamino-5-pentafluorosulfanylphenyl)-2-oxo-ethyl]-6-ethoxy-3-imino-2,3-dihydro-1H-isoindole-5-carboxamide as the trifluoroacetic acid salt N-Methyl-3-amino-6-ethoxy-1H-isoindole-5-carboxamide (13 mg, purchased from Chembiotek) was reacted with N-[3-(2-bromoacetyl)-5-pentafluorosulfanylphenyl]acetamide (21 mg) analogously to example 3b). 11 mg of the desired compound were obtained.

LC-MS rt: 1.17 min [M+H]$^+$: 535.0

Example 9

2-(5,6-Diethoxy-7-fluoro-1-imino-1,3-dihydroisoindol-2-yl)-1-[3-methylamino-5-(pentamethylsulfanyl)phenyl]ethanone as the trifluoroacetic acid salt

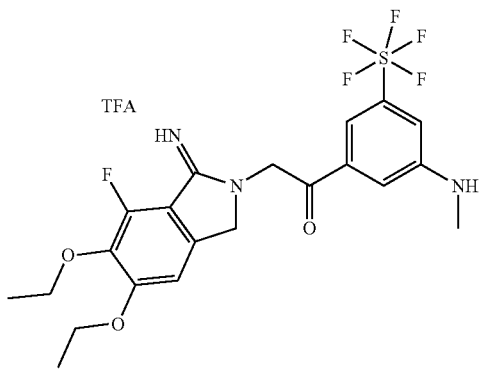 [SMILES: CCOc1cc2c(c(F)c1OCC)C(=N)N(CC(=O)c1cc(NC)cc(S(F)(F)(F)(F)F)c1)C2]

5,6-Diethoxy-7-fluoro-3H-isoindol-1-ylamine (60 mg, prepared according to EP 1391451 or CA 2515715) was initially charged in absolute DMF (5 ml), and 2-bromo-1-(3-methylamino-5-pentafluorosulfanylphenyl)ethanone (98 mg, example 3a), dissolved in DMF (1 ml), was added dropwise at RT while stirring. After stirring at 60° C. for 6 h, the solvent was drawn off under reduced pressure and the residue was purified by means of preparative HPLC. The product-containing fractions were combined, freed of the acetonitrile and freeze-dried. 36 mg of the title compound were obtained.

LC-MS rt: 1.31 min [M+H]$^+$: 512.3

Example 10

N-Methyl-6-ethoxy-3-imino-2-{2-[3-dimethanesulfonylamino-5-(pentafluorosulfanyl)phenyl]-2-oxoethyl}-2,3-dihydro-1H-isoindole-5-carboxamide as the trifluoroacetic acid salt

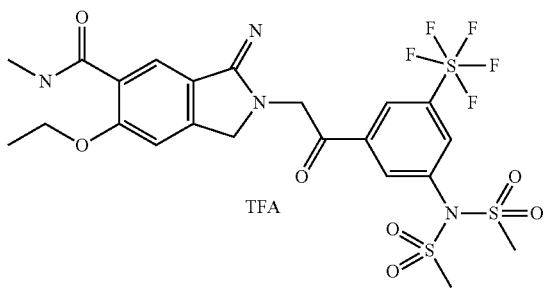 [SMILES: CCOc1cc2c(cc1C(=O)NC)C(=N)N(CC(=O)c1cc(N(S(C)(=O)=O)S(C)(=O)=O)cc(S(F)(F)(F)(F)F)c1)C2]

10a) 1-(3-Dimethanesulfonylamino-5-pentafluorosulfanylphenyl)ethanone

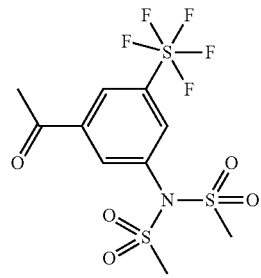 [SMILES: CC(=O)c1cc(N(S(C)(=O)=O)S(C)(=O)=O)cc(S(F)(F)(F)(F)F)c1]

1-[3-Amino-5-(pentafluorosulfanyl)phenyl]ethanone trifluoroacetic acid salt (100 mg, example 4d) was dissolved in methylene chloride (10 ml), triethylamine (120 µl) was added, and methanesulfonyl chloride (21 µl) was added while stirring. After 2 h, the mixture was left to stand overnight and then further methanesulfonyl chloride (20 µl) was added. After a further 2 h, the solvent was drawn off and the residue was taken up with ethyl acetate and water, and adjusted to pH 9 with saturated sodium hydrogencarbonate solution, and the aqueous phase was extracted twice more with ethyl acetate. The combined extracts were dried over magnesium sulfate, filtered and concentrated. The residue was purified by means of preparative HPLC. The product-containing fractions were combined, freed of the acetonitrile and freeze-dried. 36 mg of the title compound were obtained.

$^1$H NMR (400 MHz, DMSO-d$_6$) [ppm]: 8.49 (1H); 8.40 (1H); 8.31 (1H); 3.62 (6H); 2.71 (3H)

10b) 2-Bromo-1-(3-dimethanesulfonylamino-5-pentafluorosulfanylphenyl)ethanone

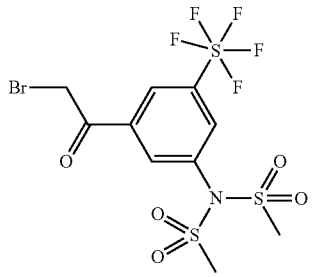 [SMILES: CS(=O)(=O)N(c1cc(C(=O)CBr)cc(S(F)(F)(F)(F)F)c1)S(C)(=O)=O]

1-(3-Dimethanesulfonylamino-5-pentafluorosulfanylphenyl)ethanone (33 mg) was brominated analogously to example 8b), by stirring the reaction mixture in 2N sulfuric acid for 2 h, and it was possible to dispense with a preparative purification. 40 mg of the title compound were obtained.

¹H NMR (400 MHz, CDCl₃) [ppm]: 8.47 (1H); 8.09 (1H); 7.97 (1H); 4.42 (2H); 3.46 (6H)

10c) N-Methyl-6-ethoxy-3-imino-2-{2-[3-dimethanesulfonylamino-5-(pentafluorosulfanyl)phenyl]-2-oxoethyl}-2,3-dihydro-1H-isoindole-5-carboxamide as the trifluoroacetic acid salt N-Methyl-3-amino-6-ethoxy-1H-isoindole-5-carboxamide (9 mg, purchased from Chembiotek) was reacted with N-[3-(2-bromo-acetyl)-5-pentafluorosulfanylphenyl]-N-ethyl-2,2,2-trifluoroacetamide (19 mg) analogously to example 3b). 6 mg of the desired compound were obtained.

LC-MS rt: 1.20 min [M+H]⁺: 649.0

Example 11

N-Methyl-2-{2-[3-(acetylmethylamino)-5-(pentafluorosulfanyl)phenyl]-2-oxoethyl}-6-ethoxy-3-imino-2,3-dihydro-1H-isoindole-5-carboxamide as the trifluoroacetic acid salt

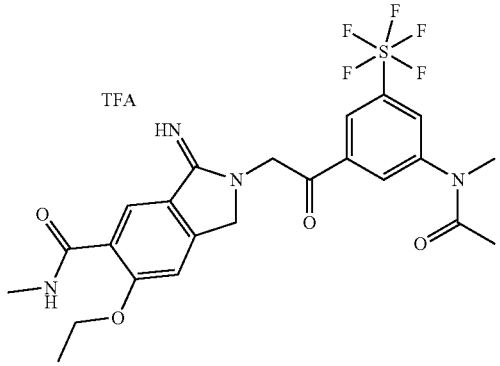 [SMILES: CCOc1cc2c(cc1C(=O)NC)C(=N)N(CC(=O)c1cc(N(C)C(C)=O)cc(S(F)(F)(F)(F)F)c1)C2]

11a) N-[3-Acetyl-5-(pentafluorosulfanyl)phenyl]-2,2,2-trifluoro-N-methylacetamide

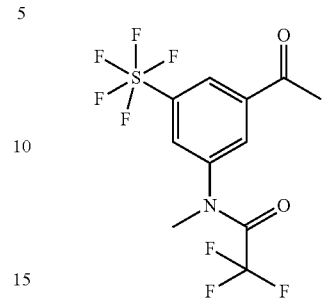

In a microwave insert, N-(3-acetyl-5-pentafluorosulfanylphenyl)-2,2,2-trifluoroacetamide (250 mg, example 4d) was dissolved in absolute dimethoxyethane (7.5 ml), and powdered potassium carbonate and iodomethane were added.

Subsequently, the mixture was heated to 100° C. in the microwave for 40 min. Once further N-(3-acetyl-5-pentafluorosulfanylphenyl)-2,2,2-trifluoroacetamide (3×250 mg) had been converted in the manner described, the four batches were worked up together, having been decanted from the potassium carbonate into 1N hydrochloric acid while cooling with ice. After repeatedly washing the potassium carbonate residue with dimethoxyethane, the aqueous phase was extracted five times with ethyl acetate. The combined extracts were dried over magnesium sulfate, filtered and concentrated. The residue was purified by means of preparative HPLC. The product-containing fractions were combined, freed of the acetonitrile and extracted five times with ethyl acetate. The combined extracts were dried over magnesium sulfate, filtered and concentrated. 650 mg of the desired compound were obtained.

LC-MS rt: 1.62 min [M+H]⁺: 372.0

11b) N-[3-(2-Bromoacetyl)-5-(pentafluorosulfanyl)phenyl]-2,2,2-trifluoro-N-methylacetamide

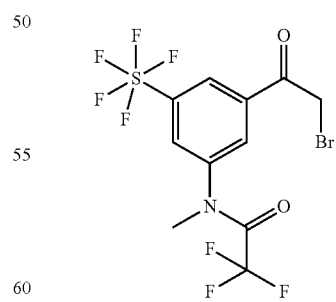

N-[3-Acetyl-5-(pentafluorosulfanyl)phenyl]-2,2,2-trifluoro-N-methylacetamide (650 mg) was brominated analogously to example 8b). 780 mg of the title compound were obtained, which were converted further without purification.

LC-MS rt: 1.73 min [M+H]⁺: 449.9

11c) 2-Bromo-1-[3-methylamino-5-(pentafluorosulfanyl)phenyl]ethanone

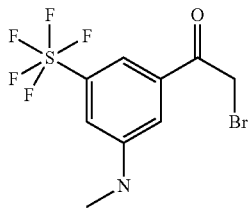 [SMILES: CNc1cc(C(=O)CBr)cc(S(F)(F)(F)(F)F)c1]

N-[3-(2-Bromoacetyl)-5-(pentafluorosulfanyl)phenyl]-2,2,2-trifluoro-N-methylacetamide (780 mg) was converted correspondingly to example 6 to detach the trifluoroacetyl group. The crude product was purified by means of preparative HPLC. The product-containing fractions were combined, freed of the acetonitrile, basified with sodium hydrogencarbonate and extracted three times with ethyl acetate. The combined extracts were dried over magnesium sulfate, filtered and concentrated. 124 mg of the desired compound were obtained.

LC-MS rt: 1.67 min [M+H]$^+$: 353.9

11d) N-[3-(2-Bromoacetyl)-5-(pentafluorosulfanyl)phenyl]-N-methylacetamide

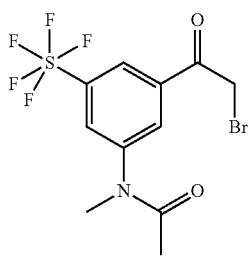 [SMILES: CC(=O)N(C)c1cc(C(=O)CBr)cc(S(F)(F)(F)(F)F)c1]

2-Bromo-1-[3-methylamino-5-(pentafluorosulfanyl)phenyl]ethanone (100 mg) was initially charged in methylene chloride (5 ml), and acetyl bromide (21 µl) was added while stirring. After stirring for 2 h, further acetyl bromide (21 µl) was added and the mixture was stirred for another 2 h. After leaving the mixture to stand overnight, acetyl bromide (21 µl) was added once again. After a further 4 h, the reaction mixture was concentrated and the residue was purified by means of preparative HPLC. The product-containing fractions were combined, freed of the acetonitrile, basified with sodium hydrogencarbonate and extracted three times with ethyl acetate. The combined extracts were dried over magnesium sulfate, filtered and concentrated. 50 mg of the desired compound were obtained.

LC-MS rt: 1.47 min [M+H]$^+$: 396.0

11e) N-Methyl-2-{2-[3-(acetylmethylamino)-5-(pentafluorosulfanyl)phenyl]-2-oxoethyl}-6-ethoxy-3-imino-2,3-dihydro-1H-isoindole-5-carboxamide as the trifluoroacetic acid salt N-Methyl-3-amino-6-ethoxy-1H-isoindole-5-carboxamide (9 mg, purchased from Chembiotek) was reacted with N-[3-(2-bromoacetyl)-5-(pentafluorosulfanyl)phenyl]-N-methylacetamide (15 mg) analogously to example 3b). 9 mg of the desired compound were obtained.

LC-MS rt: 1.09 min [M+H]$^+$: 549.0

Example 12

N-[3-[2-(5,6-diethoxy-7-fluoro-1-imino-1,3-dihydroisoindol-2-yl)acetyl]-5-(pentafluorosulfanyl)phenyl]-N-methylacetamide as the trifluoroacetic acid salt

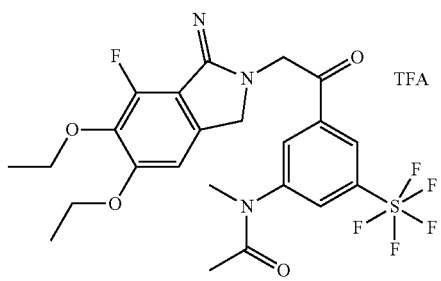 [SMILES: CCOc1cc2c(c(F)c1OCC)C(=N)N(CC(=O)c1cc(N(C)C(C)=O)cc(S(F)(F)(F)(F)F)c1)C2]

5,6-Diethoxy-7-fluoro-3H-isoindol-1-ylamine (10 mg, prepared according to EP 1391451 or CA 2515715) was initially charged in absolute DMF (1.5 ml), and N-[3-(2-bromoacetyl)-5-(pentafluorosulfanyl)phenyl]-N-methylacetamide (16 mg, example 11d), dissolved in DMF (0.5 ml), was added dropwise at RT while stirring. After stirring at RT for 3 h, the mixture was left to stand overnight, then the solvent was drawn off under reduced pressure. The residue was purified by means of preparative HPLC. The product-containing fractions were combined, freed of the acetonitrile and freeze-dried. 15 mg of the title compound were obtained.

LC-MS rt: 1.23 min [M+H]$^+$: 554.0

Example 13

N-[3-[2-(5,6-Diethoxy-7-fluoro-1-imino-1,3-dihydroisoindol-2-yl)acetyl]-5-(pentafluorosulfanyl)phenyl]isobutyramide as the trifluoroacetic acid salt

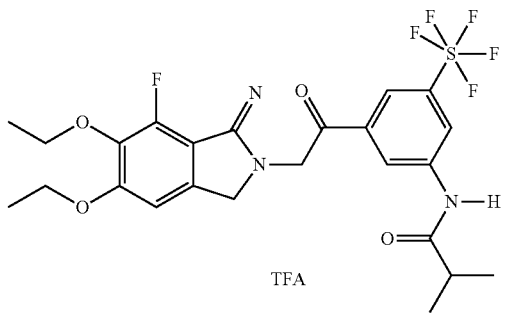 [SMILES: CCOc1cc2c(c(F)c1OCC)C(=N)N(CC(=O)c1cc(NC(=O)C(C)C)cc(S(F)(F)(F)(F)F)c1)C2]

13a) N-[3-(2-Bromoacetyl)-5-(pentafluorosulfanyl)phenyl]isobutyramide

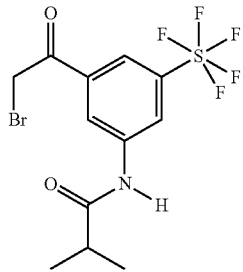 [SMILES: CC(C)C(=O)Nc1cc(C(=O)CBr)cc(S(F)(F)(F)(F)F)c1]

Proceeding from 1-[3-amino-5-(pentafluorosulfanyl)phenyl]ethanone trifluoroacetate (80 mg, example 4d), 30 mg of the title compound were prepared analogously to examples 8a) and b). The acylating agent used was isobutyryl chloride instead of acetic anhydride.
LC-MS rt: 1.67 min [M+H]$^+$: 410.0

13b) N-[3-[2-(5,6-Diethoxy-7-fluoro-1-imino-1,3-dihydroisoindol-2-yl)acetyl]-5-(pentafluorosulfanyl)phenyl]isobutyramide as the trifluoroacetic acid salt 5,6-Diethoxy-7-fluoro-3H-isoindol-1-ylamine (7 mg, prepared according to EP 1391451 or CA 2515715) was reacted according to example 12 with N-[3-(2-bromoacetyl)-5-(pentafluorosulfanyl)phenyl]isobutyramide (12 mg). 7 mg of the desired product were obtained.
LC-MS rt: 1.34 min [M+H]$^+$: 568.2

Example 14

N-[3-[2-(5,6-Diethoxy-7-fluoro-1-imino-1,3-dihydroisoindol-2-yl)acetyl]-5-pentafluorosulfanyl)phenyl]acetamide as the hydrobromide

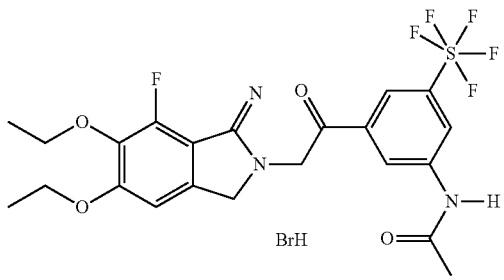 [SMILES: CCOc1cc2c(c(F)c1OCC)C(=N)N(CC(=O)c1cc(NC(C)=O)cc(S(F)(F)(F)(F)F)c1)C2 ; Br]

14a) 3-Acetylamino-N-methoxy-N-methyl-5-(pentafluorosulfanyl)benzamide

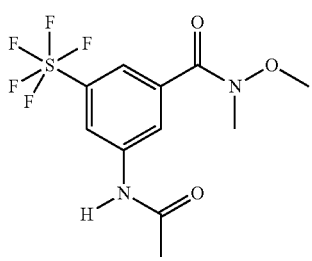 [SMILES: CON(C)C(=O)c1cc(NC(C)=O)cc(S(F)(F)(F)(F)F)c1]

3-Amino-N-methoxy-N-methyl-5-pentafluorosulfanyl-benzamide (1.2 g, example 4b) was reacted analogously to example 4c) with acetic anhydride instead of with trifluoroacetic anhydride. 1.3 g of the desired compound were isolated.
LC-MS rt: 1.26 min [M+H]$^+$: 349.0

14b) N-[3-Acetyl-5-(pentafluorosulfanyl)phenyl]acetamide

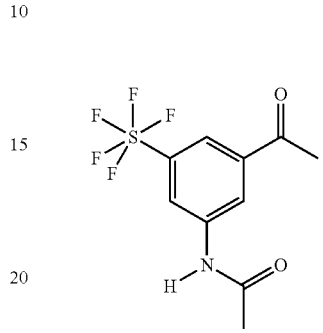

3-Acetylamino-N-methoxy-N-methyl-5-(pentafluorosulfanyl)benzamide (1.2 g) was converted analogously to example 4d). A crude product purification was carried out, which was effected using silica gel with dichloromethane-methanol as the eluent. 859 mg of the desired compound were obtained.
LC-MS rt: 1.34 min [M+H]$^+$: 304.0

14c) N-[3-(2-bromoacetyl)-5-(pentafluorosulfanyl)phenyl]acetamide

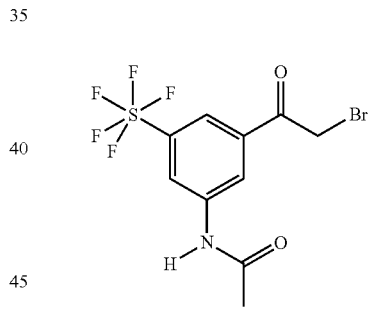

N-[3-Acetyl-5-(pentafluorosulfanyl)phenyl]acetamide (859 mg) was brominated according to example 8b). However, the crude product was purified using silica gel with ethyl acetate/heptane as the eluent. 480 mg of the desired compound were obtained.
LC-MS rt: 1.47 min [M+H]$^+$: 382.0

14d) N-[3-[2-(5,6-Diethoxy-7-fluoro-1-imino-1,3-dihydroisoindol-2-yl)acetyl]-5-pentafluorosulfanyl)phenyl]acetamide as the hydrobromide At 7° C., 5,6-diethoxy-7-fluoro-3H-isoindol-1-ylamine (149 mg, prepared according to EP 1391451 or CA 2515715) was dissolved in absolute THF (6 ml), and added dropwise while stirring to a solution of N-[3-(2-bromoacetyl)-5-(pentafluorosulfanyl)phenyl]acetamide (281 mg) in absolute THF (2 ml). Then the cooling bath was removed and the mixture was stirred at RT for 6 h. After leaving to stand overnight, the precipitate formed was filtered off with suction, washed with a little THF and dissolved in an acetonitrile-water mixture.

After freeze-drying, 200 mg of the title compound were obtained.
LC-MS rt: 1.28 min [M+H]+: 540.2

Example 15
N-[5-[2-(5,6-Diethoxy-7-fluoro-1-imino-1,3-dihydroisoindol-2-yl)acetyl]-4-methyl-2-(pentafluorosulfanyl)phenyl]acetamide as the trifluoroacetic acid salt

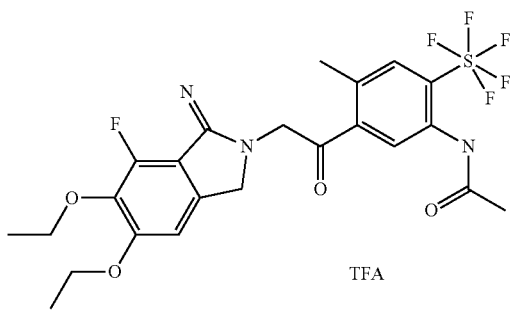 [SMILES: CCOc1cc2c(c(F)c1OCC)C(=N)N(CC(=O)c1cc(NC(C)=O)c(S(F)(F)(F)(F)F)cc1C)C2]

TFA 15a) 5-Amino-N-methoxy-2,N-dimethyl-4-(pentafluorosulfanyl)benzamide

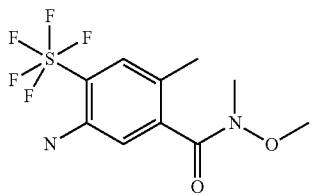 [SMILES: CON(C)C(=O)c1cc(N)c(S(F)(F)(F)(F)F)cc1C]

5-Amino-2-methyl-4-(pentafluorosulfanyl)benzoic acid (500 mg, WO 2005/47239) was dissolved in methylene chloride (30 ml) and admixed while stirring with N,O-dimethylhydroxylamine hydrochloride (176 mg), 1-propanephosphonic anhydride (1.1 ml) and triethylamine (0.25 ml). After stirring for 4 h and leaving to stand overnight, the reaction mixture was concentrated, the residue was taken up with ethyl acetate and the solution was washed twice with potassium hydrogen sulfate solution and twice with sodium hydrogencarbonate solution. After drying over magnesium sulfate, the organic phase was filtered and concentrated. The resulting crude product (500 mg) was converted further directly.
LC-MS rt: 1.33 min [M+H]+: 321.0

15b) 5-Acetylamino-N-methoxy-2,N-dimethyl-4-(pentafluorosulfanyl)benzamide

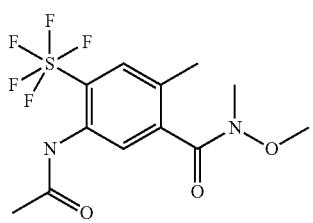 [SMILES: CON(C)C(=O)c1cc(NC(C)=O)c(S(F)(F)(F)(F)F)cc1C]

5-Amino-N-methoxy-2,N-dimethyl-4-(pentafluorosulfanyl)benzamide (200 mg) was dissolved in dichloromethane (10 ml) and then triethylamine (100 µl) and acetyl chloride (50 µl) were added while stirring. After 2 h, further acetyl chloride was added (50 µl) and the mixture was stirred for 4 h. Then the reaction mixture was admixed with water and saturated sodium hydrogencarbonate solution, and the organic phase was removed and washed three times with water. After drying over magnesium sulfate, the organic phase was filtered and concentrated. The residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 170 mg of the desired compound were obtained.
LC-MS rt: 1.12 min [M+H]+: 363.0

15c) N-[5-Acetyl-4-methyl-2-(pentafluorosulfanyl)phenyl]acetamide

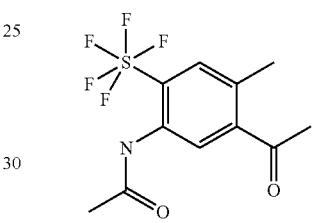

5-Acetylamino-N-methoxy-2,N-dimethyl-4-(pentafluorosulfanyl)benzamide (170 mg) was converted analogously to example 4d). 130 mg of crude product were obtained, which was used directly in the next stage.
LC-MS rt: 1.22 min [M+H]+: 318.0

15d) N-[5-(2-Bromoacetyl)-4-methyl-2-(pentafluorosulfanyl)phenyl]acetamide

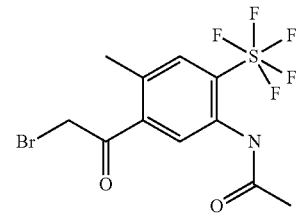 [SMILES: CC(=O)Nc1cc(C(=O)CBr)c(C)cc1S(F)(F)(F)(F)F]

N-[5-Acetyl-4-methyl-2-(pentafluorosulfanyl)phenyl]acetamide (130 mg) was brominated according to example 8b). 41 mg of the desired compound were obtained.
LC-MS rt: 1.39 min [M+H]+: 395.9

15e) N-[5-[2-(5,6-Diethoxy-7-fluoro-1-imino-1,3-dihydroisoindol-2-yl)-acetyl]-4-methyl-2-(pentafluorosulfanyl)phenyl]acetamide as the trifluoroacetic acid salt 5,6-Diethoxy-7-fluoro-3H-isoindol-1-ylamine (11 mg, prepared according to EP 1391451 or CA 2515715) was reacted with N-[5-(2-bromoacetyl)-4-methyl-2-(pentafluorosulfanyl)phenyl]acetamide (18 mg) according to example 12. 15 mg of the desired product were obtained.

LC-MS rt: 1.24 min [M+H]⁺: 554.2

Example 16

1-[5-Amino-2-methyl-4-(pentafluorosulfanyl)phenyl]-2-(5,6-diethoxy-7-fluoro-1-imino-1,3-dihydroisoindol-2-yl)ethanone as the trifluoroacetic acid salt

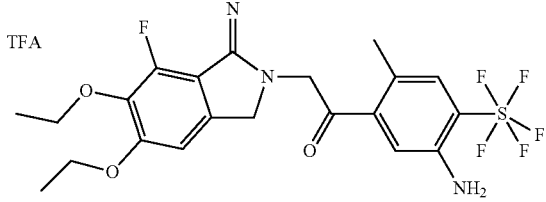 [SMILES: CCOc1cc2c(c(F)c1OCC)C(=N)N(CC(=O)c1cc(N)c(S(F)(F)(F)(F)F)cc1C)C2]

N-[5-[2-(5,6-Diethoxy-7-fluoro-1-imino-1,3-dihydroisoindol-2-yl)acetyl]-4-methyl-2-(pentafluorosulfanyl) phenyl]acetamide trifluoroacetic acid salt (9 mg, example 15) was converted analogously to example 6. For workup, the mixture was diluted with water and the aqueous phase was extracted three times with ethyl acetate. The combined extracts were washed with saturated sodium hydrogencarbonate solution to free them of acid, dried with magnesium sulfate, filtered and concentrated. The residue was purified by means of preparative HPLC. The product-containing fractions were combined, freed of the acetonitrile and freeze-dried. 4 mg of the title compound were obtained.

LC-MS rt: 1.38 min [M+H]⁺: 512.2

Example 17

N-{3-[2-(5,6-Diethoxy-7-fluoro-1-imino-1,3-dihydroisoindol-2-yl)acetyl]-5-pentafluorosulfanylphenyl}-3,3-dimethylbutyramide as the trifluoroacetic acid salt

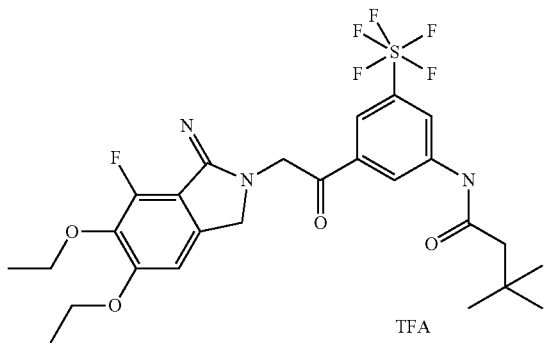 [SMILES: CCOc1cc2c(c(F)c1OCC)C(=N)N(CC(=O)c1cc(NC(=O)CC(C)(C)C)cc(S(F)(F)(F)(F)F)c1)C2]

17a) N-[3-(2-Bromoacetyl)-5-(pentafluorosulfanyl) phenyl]-3,3-dimethylbutyramide

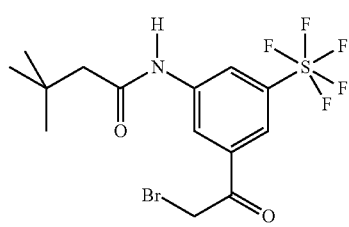 [SMILES: CC(C)(C)CC(=O)Nc1cc(C(=O)CBr)cc(S(F)(F)(F)(F)F)c1]

N-[3-(2-Bromoacetyl)-5-(pentafluorosulfanyl)phenyl]-3, 3-dimethylbutyramide (100 mg) was synthesized proceeding from 3-amino-N-methoxy-N-methyl-5-pentafluorosulfanyl-benzamide (200 mg, example 4b)) analogously to example 14a-c).

LC-MS rt: 1.82 min [M+H]⁺: 438.0

17b) N-{3-[2-(5,6-Diethoxy-7-fluoro-1-imino-1,3-dihydroisoindol-2-yl)acetyl]-5-pentafluorosulfanylphenyl}-3,3-dimethylbutyramide as the trifluoroacetic acid salt 5,6-Diethoxy-7-fluoro-3H-isoindol-1-ylamine (13 mg, prepared according to EP 1391451 or CA 2515715) was reacted with N-[3-(2-bromoacetyl)-5-(pentafluorosulfanyl) phenyl]-3,3-dimethylbutyramide (24 mg) according to example 12. 13 mg of the desired product were obtained.

LC-MS rt: 1.39 min [M+H]⁺: 596.2

Example 18

1-{3-[2-(5,6-Diethoxy-7-fluoro-1-imino-1,3-dihydroisoindol-2-yl)acetyl]-5-pentafluorosulfanylphenyl}pyrrolidine-2,5-dione as the trifluoroacetic acid salt

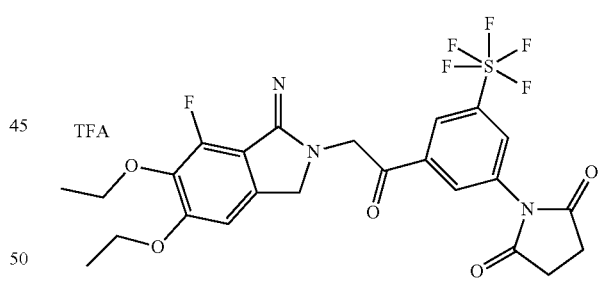

18a) 1-[3-Amino-5-(pentafluorosulfanyl)phenyl]ethanone

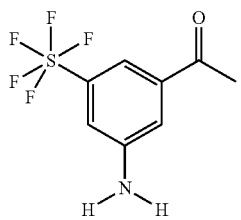 [SMILES: CC(=O)c1cc(N)cc(S(F)(F)(F)(F)F)c1]

N-(3-Acetyl-5-pentafluorosulfanylphenyl)-2,2,2-trifluoroacetamide (3.3 g, example 4d) was converted according to example 6. The resulting crude product was purified with ethyl acetate/n-heptane using silica gel. 1.1 g of the desired product were obtained.

LC-MS rt: 1.37 min [M+H]⁺: 262.0

18b) 1-[3-Acetyl-5-(pentafluorosulfanyl)phenyl]pyrrolidine-2,5-dione

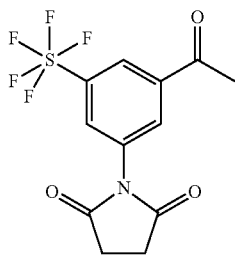 [SMILES: CC(=O)c1cc(N2C(=O)CCC2=O)cc(S(F)(F)(F)(F)F)c1]

1-[3-Amino-5-(pentafluorosulfanyl)phenyl]ethanone (200 mg) was mixed with succinic acid (90 mg) in a flask, and then polyphosphoric acid (10 ml) was added. The mixture was heated to 130° C. for 8 h while stirring and, after leaving to stand overnight, further succinic acid (50 mg) was added and the mixture was heated to 130° C. for a further 4 h. After cooling, the mixture was stirred into ice-water and the aqueous solution was extracted five times with ethyl acetate. The combined extracts were washed with saturated sodium hydrogencarbonate solution, dried over magnesium sulfate, filtered and concentrated. The residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 42 mg of the desired compound were obtained.

¹H NMR (400 MHz, CDCl₃) [ppm]: 8.33 (1H); 8.09 (1H); 7.97 (1H), 2.97 (4H); 2.67 (3H)

18c) 1-[3-(2-Bromoacetyl)-5-(pentafluorosulfanyl)phenyl]pyrrolidine-2,5-dione

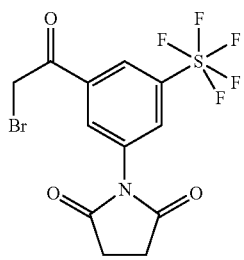 [SMILES: O=C(CBr)c1cc(N2C(=O)CCC2=O)cc(S(F)(F)(F)(F)F)c1]

1-[3-Acetyl-5-(pentafluorosulfanyl)phenyl]pyrrolidine-2,5-dione (42 mg) was brominated analogously to example 8b). 19 mg of the desired bromide were obtained.

¹H NMR (400 MHz, DMSO-d₆) [ppm]: 8.47 (1H); 8.18 (2H); 5.04 (2H); 2.80 (4H)

18d) 1-{3-[2-(5,6-Diethoxy-7-fluoro-1-imino-1,3-dihydroisoindol-2-yl)acetyl]-5-pentafluorosulfanylphenyl}pyrrolidine-2,5-dione as the trifluoroacetic acid salt 5,6-Diethoxy-7-fluoro-3H-isoindol-1-ylamine (9 mg, prepared according to EP 1391451 or CA 2515715) was reacted with 1-[3-(2-bromoacetyl)-5-(pentafluorosulfanyl)phenyl]pyrrolidine-2,5-dione (18 mg) according to example 12. 9 mg of the desired product were obtained.

LC-MS rt: 1.26 min [M+H]⁺: 580.2

Example 19

1-[2-Amino-4-(pentafluorosulfanyl)phenyl]-2-(5,6-diethoxy-7-fluoro-1-imino-1,3-dihydroisoindol-2-yl)ethanone as the trifluoroacetic acid salt

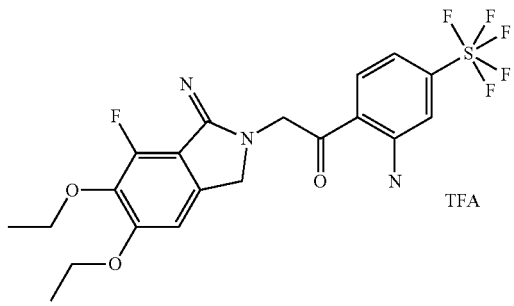 [SMILES: CCOc1cc2c(c(F)c1OCC)C(=N)N(CC(=O)c1ccc(S(F)(F)(F)(F)F)cc1N)C2]

19a) 2-Amino-4-(pentafluorosulfanyl)benzoic acid

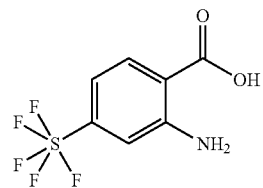 [SMILES: Nc1cc(S(F)(F)(F)(F)F)ccc1C(=O)O]

4-(Pentafluorosulfanyl)benzoic acid (4 g) was first nitrated and then reduced analogously to example 2a). 2.1 g of the desired compound were obtained.

LC-MS rt: 1.35 min [M+H]⁺: 264.0

19b) 2-Amino-N-methoxy-N-methyl-4-(pentafluorosulfanyl)benzamide

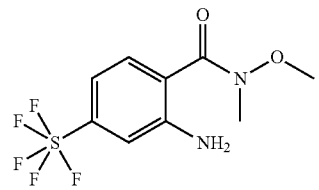 [SMILES: CON(C)C(=O)c1ccc(S(F)(F)(F)(F)F)cc1N]

2-Amino-4-(pentafluorosulfanyl)benzoic acid (2.0 g) was reacted with N,O-dimethylhydroxylamine hydrochloride analogously to example 15a). 2.3 g of the desired product were obtained.

LC-MS rt: 1.33 min [M+H]⁺: 307.0

19c) N-Methoxy-N-methyl-4-(pentafluorosulfanyl)-2-(2,2,2-trifluoroacetylamino)benzamide

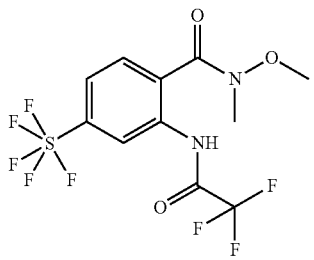 [SMILES: CON(C)C(=O)c1ccc(S(F)(F)(F)(F)F)cc1NC(=O)C(F)(F)F]

2-Amino-N-methoxy-N-methyl-4-(pentafluorosulfanyl)benzamide (2.3 g) was reacted with trifluoroacetic anhydride analogously to example 4c). 2.7 g of the desired product were obtained.

LC-MS rt: 1.54 min [M+H]$^+$: 403.0

19d) N-[2-Acetyl-5-(pentafluorosulfanyl)phenyl]-2,2,2-trifluoroacetamide and 1-[2-amino-4-(pentafluorosulfanyl)phenyl]ethanone

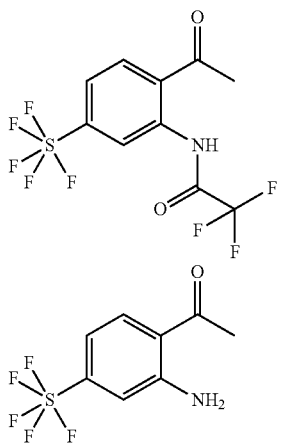

N-Methoxy-N-methyl-4-(pentafluorosulfanyl)-2-(2,2,2-trifluoroacetylamino)benzamide (2.7 g) was converted analogously to example 4d), except that the ethyl acetate phase, before the drying with magnesium sulfate, was washed with saturated sodium hydrogencarbonate solution to free it of acid and the residue was purified using silica gel with dichloromethane as the eluent. 1.45 g of N-[2-acetyl-5-(pentafluorosulfanyl)-phenyl]-2,2,2-trifluoroacetamide LC-MS rt: 1.77 min [M+H]$^+$: 358.0
and
310 mg of 1-[2-amino-4-(pentafluorosulfanyl)phenyl]ethanone were obtained.

LC-MS rt: 1.52 min [M+H]$^+$: 262.0

19e) 1-[2-Amino-4-(pentafluorosulfanyl)phenyl]-2-bromoethanone

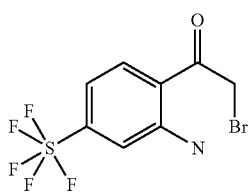 [SMILES: Nc1cc(S(F)(F)(F)(F)F)ccc1C(=O)CBr]

N-[2-Acetyl-5-(pentafluorosulfanyl)phenyl]-2,2,2-trifluoroacetamide (200 mg) was brominated according to example 8b). 28 mg of the desired compound were obtained. Alternatively, 1-[2-amino-4-(pentafluorosulfanyl)phenyl]-2-bromoethanone was also preparable as described in example 20b).

LC-MS rt: 1.61 min [M+H]$^+$: 339.9

19f) 1-[2-Amino-4-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (19 mg, prepared according to EP 1391451 or CA 2515715) was reacted with 1-[2-amino-4-(pentafluorosulfanyl)phenyl]-2-bromoethanone (27 mg) according to example 12. 21 mg of the desired product were obtained.

LC-MS rt: 1.26 min [M+H]$^+$: 498.0

Example 20

1-[2-Amino-5-bromo-4-(pentafluorosulfanyl)phenyl]-2-(5,6-diethoxy-7-fluoro-1-imino-1,3-dihydroisoindol-2-yl)ethanone as the trifluoroacetic acid salt

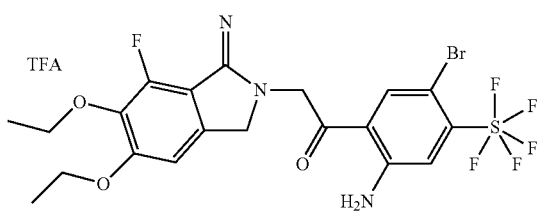 [SMILES: CCOc1cc2c(c(F)c1OCC)C(=N)N(CC(=O)c1cc(Br)c(S(F)(F)(F)(F)F)cc1N)C2]

20a) N-[2-Acetyl-5-(pentafluorosulfanyl)phenyl]acetamide

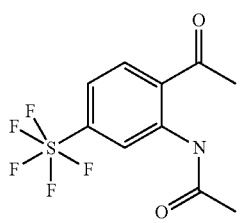 [SMILES: CC(=O)Nc1cc(S(F)(F)(F)(F)F)ccc1C(C)=O]

1-[2-Amino-4-(pentafluorosulfanyl)phenyl]ethanone (150 mg, example 19d) was dissolved in methylene chloride (5 ml). After adding triethylamine (95 µl) and acetyl chloride (51 µl), the mixture was stirred at RT for 4 h. Then methylene chloride, water and saturated sodium hydrogencarbonate solution were added. The organic phase was removed, washed three times with water, dried over magnesium sulfate, filtered and concentrated. 165 mg of the desired product were obtained.

LC-MS rt: 1.45 min [M+H]$^+$: 304.0

20b) 1-[2-Amino-5-bromo-4-(pentafluorosulfanyl)phenyl]-2-bromoethanone and 1-[2-amino-4-(pentafluorosulfanyl)phenyl]-2-bromoethanone

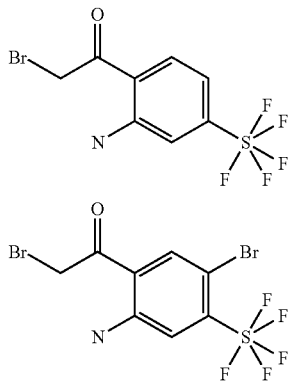

N-[2-Acetyl-5-(pentafluorosulfanyl)phenyl]acetamide (80 mg) was converted according to example 8b). After workup and chromatography, 21 mg of 1-[2-amino-4-(pentafluorosulfanyl)phenyl]-2-bromoethanone LC-MS rt: 1.61 min [M+H]+: 339.9 and 24 mg of 1-[2-amino-5-bromo-4-(pentafluorosulfanyl)phenyl]-2-bromoethanone were obtained.

LC-MS rt: 1.73 min [M+H]+: 417.8

20c) 1-[2-Amino-5-bromo-4-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (13 mg, prepared according to EP 1391451 or CA 2515715) was reacted with 1-[2-amino-5-bromo-4-(pentafluorosulfanyl)phenyl]-2-bromoethanone (23 mg) according to example 12. 10 mg of the desired product were obtained.

LC-MS rt: 1.31 min [M+H]+: 576.0

Example 21

2-(5,6-Diethoxy-7-fluoro-1-imino-1,3-dihydroisoindol-2-yl)-1-[3-methoxy-5-(pentafluorosulfanyl)phenyl]ethanone as the trifluoroacetic acid salt

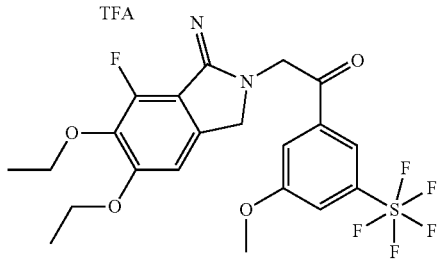 [SMILES: CCOc1cc2c(c(F)c1OCC)C(=N)N(CC(=O)c1cc(OC)cc(S(F)(F)(F)(F)F)c1)C2]

21a) 3-Hydroxy-5-(pentafluorosulfanyl)benzoic acid

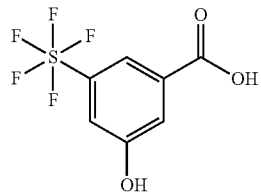 [SMILES: O=C(O)c1cc(O)cc(S(F)(F)(F)(F)F)c1]

3-Amino-5-pentafluorosulfanylbenzoic acid (1.5 g, example 2a)) was dissolved in 35% sulfuric acid (45 ml) and cooled to −5° C., and a solution of sodium nitrite (387 mg) in water (40 ml) was added dropwise within 10 min. After 40 min, the cooling bath was removed and the mixture was heated to 100° C. After 4 h, the mixture was cooled and the solution was decanted. The clear acidic solution was extracted five times with ethyl acetate. The combined extracts were dried over magnesium sulfate, filtered and concentrated. The crude product was crystallized from ethyl acetate/heptane. 1 g of the desired compound was obtained.

$^1$H NMR (400 MHz, DMSO-d$_6$) [ppm]: 10.72 (1H); 7.71 (1H); 7.57 (1H); 7.46 (1H)

21b) Methyl 3-methoxy-5-(pentafluorosulfanyl)benzoate

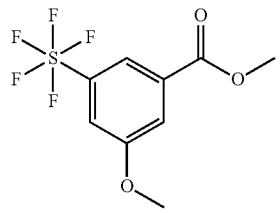 [SMILES: COC(=O)c1cc(OC)cc(S(F)(F)(F)(F)F)c1]

3-Hydroxy-5-(pentafluorosulfanyl)benzoic acid (84 mg) was dissolved in absolute DMF (5 ml). Iodomethane (100 µl) was then added while stirring, followed by finely powdered potassium carbonate (175 mg). After stirring at 40° C. for 3 hours, the mixture was cooled and admixed with water (20 ml). The mixture was then extracted four times with ether (10 ml). The combined extracts were washed once each with 1N sodium hydroxide solution (10 ml) and water (10 ml), dried over magnesium sulfate, filtered and concentrated. 81 mg of the desired compound were obtained.

LC-MS rt: 1.71 min [M+H]+: 293.0

21c) 3,N-Dimethoxy-N-methyl-5-(pentafluorosulfanyl)benzamide

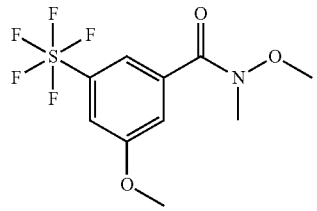 [SMILES: COc1cc(C(=O)N(C)OC)cc(S(F)(F)(F)(F)F)c1]

Methyl 3-methoxy-5-(pentafluorosulfanyl)benzoate (81 mg) was dissolved in absolute THF (5 ml), and N,O-dimethylhydroxylamine hydrochloride (42 mg) was added. Then the mixture was cooled to −15° C., and isopropylmagnesium bromide solution (0.21 ml, 2 M in THF) was added dropwise. After 20 min, the cooling bath was removed and the mixture was stirred at RT for 1 h. To complete the reaction, the mixture was twice more cooled to −15° C., isopropylmagnesium bromide solution (0.1 ml each time) was added dropwise and the mixture was stirred at RT for 1 h. Then ammonium chloride solution was added (10 ml) and the aqueous phase was extracted three times with ethyl acetate. The combined extracts were dried over magnesium sulfate, filtered and concentrated. 70 mg of the desired compound were obtained.

LC-MS rt: 1.49 min [M+H]$^+$: 322.0

21d) 1-[3-Methoxy-5-(pentafluorosulfanyl)phenyl]ethanone

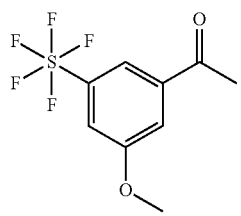 [SMILES: COc1cc(C(C)=O)cc(S(F)(F)(F)(F)F)c1]

3,N-Dimethoxy-N-methyl-5-(pentafluorosulfanyl)benzamide (70 mg) was dissolved in absolute THF, and methylmagnesium bromide (185 µl, 2 M in diethyl ether) was added dropwise at 0° C. while stirring. After addition, the ice bath was removed and the mixture was stirred at RT for 2 h. 1N hydrochloric acid was then added dropwise while cooling, followed by water and ethyl acetate. The organic phase was removed and the aqueous phase was extracted twice more with ethyl acetate. The combined extracts were dried over magnesium sulfate, filtered and concentrated. The residue was purified by means of preparative HPLC. The product-containing fractions were combined, freed of the acetonitrile and extracted three times with ethyl acetate. The combined extracts were dried over magnesium sulfate, filtered and concentrated. 34 mg of the desired compound were obtained.

LC-MS rt: 1.60 min [M+H]$^+$: 277.0

21e) 2-Bromo-1-[3-methoxy-5-(pentafluorosulfanyl)phenyl]ethanone

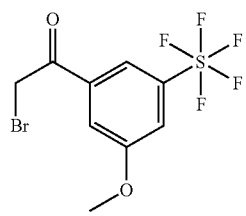 [SMILES: COc1cc(C(=O)CBr)cc(S(F)(F)(F)(F)F)c1]

1-[3-Methoxy-5-(pentafluorosulfanyl)phenyl]ethanone (34 mg) was dissolved in absolute methanol (3 ml). To this were added, while stirring, DL-camphorsulfonic acid (0.6 mg) and trimethyl orthoformate (40 mg). After stirring for 4 h, the mixture was left to stand overnight and then absolute THF (3 ml) and phenyltrimethylammonium tribromide (40 mg) were added while stirring. After stirring at RT for 2 h, the mixture was stirred at 50° C. for 3 h, left to stand over the weekend and, after adding further phenyltrimethylammonium tribromide (20 mg), stirred at 50° C. for another 5 h. The reaction mixture was concentrated, and the residue was taken up with acetonitrile and admixed with 5N sulfuric acid while stirring. After stirring for 2 h, the mixture was concentrated and the residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 15 mg of the desired compound were obtained.

LC-MS rt: 1.71 min [M+H]$^+$: 354.9

21f) 2-(5,6-Diethoxy-7-fluoro-1-imino-1,3-dihydroisoindol-2-yl)-1-[3-methoxy-5-(pentafluorosulfanyl)phenyl]ethanone as the trifluoroacetic acid salt 5,6-Diethoxy-7-fluoro-3H-isoindol-1-ylamine (9 mg, prepared according to EP 1391451 or CA 2515715) was reacted with 2-bromo-1-[3-methoxy-5-(pentafluorosulfanyl)phenyl]ethanone (15 mg) according to example 12. 8 mg of the desired product were obtained.

LC-MS rt: 1.35 min [M+H]$^+$: 513.1

Example 22

N-[3-[2-(5,6-Diethoxy-7-fluoro-1-imino-1,3-dihydroisoindol-2-yl)acetyl]-5-(pentafluorosulfanyl)phenyl]cyclobutanecarboxamide as the hydrochloride

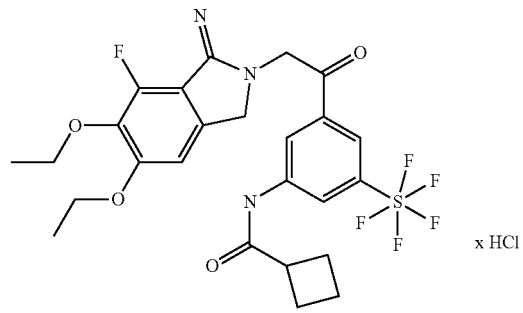 [SMILES: CCOc1cc2c(c(F)c1OCC)C(=N)N(CC(=O)c1cc(NC(=O)C3CCC3)cc(S(F)(F)(F)(F)F)c1)C2]

22a) 1-[3-Amino-5-(pentafluorosulfanyl)phenyl]ethanone

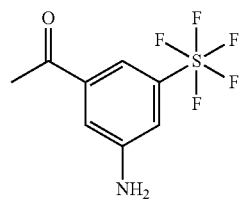 [SMILES: CC(=O)c1cc(N)cc(S(F)(F)(F)(F)F)c1]

N-(3-Acetyl-5-pentafluorosulfanylphenyl)-2,2,2-trifluoroacetamide (4 g, for preparation see example 4d) was suspended in 6 ml of water and 12 ml of acetonitrile, and 6 ml of concentrated sulfuric acid were added dropwise to this suspension. After stirring at 75° C. for 4 h and leaving to stand at RT overnight, the reaction was completed by adding another 2 ml of concentrated sulfuric acid and heating the mixture at 75° C. for 3 h. The reaction mixture was poured onto icewater and extracted with ethyl acetate. The ethyl acetate phase was washed to neutrality with saturated sodium hydrogencarbonate solution, dried over magnesium sulfate, filtered and concentrated. The crude product was purified by means of chromatography on silica gel. The product-containing fractions were combined and the solvent (heptane/ethyl acetate) was concentrated under reduced pressure. 2.53 g of 1-[3-amino-5-(pentafluorosulfanyl)phenyl]ethanone were obtained.

LC-MS rt: 1.32 min [M+H]⁺: 262.0

22b) N-[3-Acetyl-5-(pentafluorosulfanyl)phenyl]cyclobutylamide

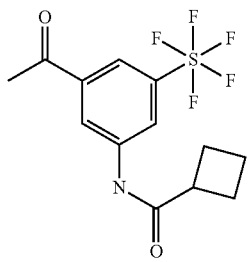 [SMILES: CC(=O)c1cc(NC(=O)C2CCC2)cc(S(F)(F)(F)(F)F)c1]

1-[3-Amino-5-(pentafluorosulfanyl)phenyl]ethanone (2 g) was dissolved in methylene chloride (30 ml), triethylamine (2.13 ml) was added and then cyclobutanecarbonyl chloride (1.362 g) was added while stirring. After stirring for 2 h, the reaction mixture was admixed with water and the phases were separated. The aqueous phase was extracted with methylene chloride, and the combined extracts were dried over magnesium sulfate, filtered and concentrated. The crude product was purified by means of chromatography on silica gel. The product-containing fractions were combined and the solvent (heptane/ethyl acetate) was removed under reduced pressure. 2.31 g of N-[3-acetyl-5-(pentafluorosulfanyl)phenyl]cyclobutylamide were obtained.

LC-MS rt: 1.53 min [M+H]⁺: 344.06

22c) N-[3-(2-Bromoacetyl)-5-pentafluorosulfanylphenyl]cyclobutylamide

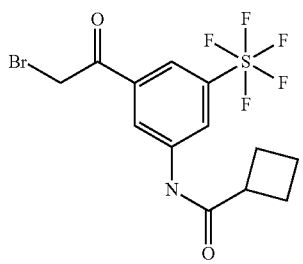 [SMILES: O=C(CBr)c1cc(NC(=O)C2CCC2)cc(S(F)(F)(F)(F)F)c1]

N-[3-Acetyl-5-(pentafluorosulfanyl)phenyl]cyclobutylamide (2.3 g) was dissolved in a mixture of methanol (30 ml) and THF (30 ml), and phenyltrimethyl tribromide (3.778 g) was added while stirring. After stirring at RT for 5 h, the reaction mixture was heated to 50° C. for 2 h and left to stand at RT overnight. The mixture was poured onto an aqueous solution of citric acid and, after stirring for 60 min, extracted twice with ethyl acetate. The combined extracts were dried over magnesium sulfate, filtered and concentrated. The residue was purified by means of chromatography on silica gel. The product-containing fractions were combined and the solvent (heptane/ethyl acetate) was removed under reduced pressure. The residue was dissolved in methylene chloride, and the solvent was removed under reduced pressure and high vacuum. 1.7 g of the desired compound were obtained.

LC-MS rt: 1.68 min [M+H]⁺: 421.9

22d) N-[3-[2-(5,6-Diethoxy-7-fluoro-1-imino-1,3-dihydroisoindol-2-yl)acetyl]-5-(pentafluorosulfanyl)phenyl]cyclobutanecarboxamide as the hydrochloride 5,6-Diethoxy-7-fluoro-3H-isoindol-1-ylamine (150 mg, prepared according to EP 1391451 or CA 2515715) and N-[3-(2-bromoacetyl)-5-pentafluorosulfanylphenyl]cyclobutylamide (292 mg) were stirred at RT in absolute DMF (5 ml) for 4 h, and the reaction mixture was left to stand overnight. The solvent was removed under reduced pressure and the residue was purified by means of preparative HPLC. The product-containing fractions were combined, freed of the acetonitrile and freeze-dried. For conversion to the hydrochloride, the residue was freeze-dried with two equivalents of 1N hydrochloric acid. 110 mg of the title compound were obtained.

LC-MS rt: 1.32 min [M+H]⁺: 580.2

Example 23

N-[3-[2-(5,6-Diethoxy-7-fluoro-1-imino-1,3-dihydroisoindol-2-yl)acetyl]-5-(pentafluorosulfanyl)phenyl]cyclopropanecarboxamide as the hydrochloride

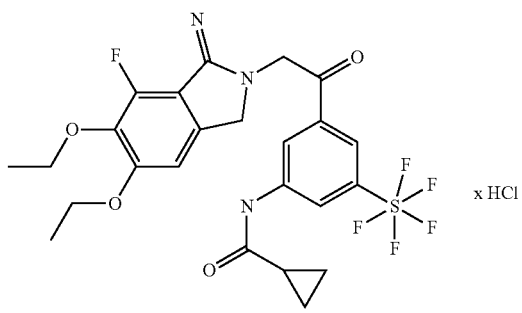 [SMILES: CCOc1cc2c(c(F)c1OCC)C(=N)N(CC(=O)c1cc(NC(=O)C3CC3)cc(S(F)(F)(F)(F)F)c1)C2]

23a) N-[3-Acetyl-5-(pentafluorosulfanyl)phenyl]cyclopropylamide

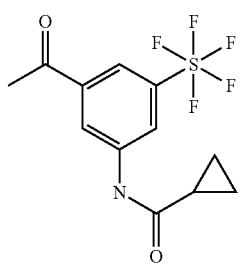 [SMILES: CC(=O)c1cc(NC(=O)C2CC2)cc(S(F)(F)(F)(F)F)c1]

1-[3-Amino-5-(pentafluorosulfanyl)phenyl]ethanone (2 g, see example 22a) was dissolved in methylene chloride (30 ml), and triethylamine (2.13 ml) was added, and then, while stirring, cyclopropanecarbonyl chloride (1.2 g). After stirring for 2 h, the reaction mixture was admixed with water and the phases were separated. The aqueous phase was extracted with methylene chloride, and the combined extracts were dried over magnesium sulfate, filtered and concentrated. The crude product was purified by means of chromatography on silica gel. The product-containing fractions were combined and the solvent (heptane/ethyl acetate) was removed under reduced pressure. 2.29 g of N-[3-acetyl-5-(pentafluorosulfanyl)phenyl]cyclopropylamide were obtained.

LC-MS rt: 1.51 min [M+H]⁺: 330.1

23b) N-[3-(2-Bromoacetyl)-5-pentafluorosulfanylphenyl]cyclobutylamide

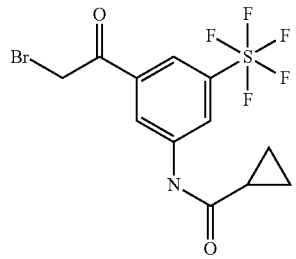 [SMILES: O=C(CBr)c1cc(NC(=O)C2CC2)cc(S(F)(F)(F)(F)F)c1]

N-[3-Acetyl-5-(pentafluorosulfanyl)phenyl]cyclopropylamide (2.29 g) was dissolved in a mixture of methanol (30 ml) and THF (30 ml), and phenyltrimethyl tribromide (3.921 g) was added while stirring. After stirring at RT for 2 h, the reaction mixture was heated to 50° C. for 2 h and left to stand at RT overnight. The mixture was poured onto an aqueous solution of citric acid and, after stirring for 60 min, extracted twice with ethyl acetate. The combined extracts were dried over magnesium sulfate, filtered and concentrated. The residue was purified by means of chromatography on silica gel. The product-containing fractions were combined and the solvent (heptane/ethyl acetate) was removed under reduced pressure. The residue was dissolved in methylene chloride, the solvent was removed under reduced pressure, and the residue thus obtained was dissolved in 100 ml of acetonitrile, admixed with 30 ml of 2N sulfuric acid and left to stand at RT overnight. The reaction mixture was diluted with water and extracted with ethyl acetate. The organic phase was washed with saturated sodium hydrogencarbonate solution, dried over magnesium sulfate, filtered and concentrated. The residue was purified by means of chromatography on silica gel. The product-containing fractions were combined and the solvent (heptane/ethyl acetate) was removed under reduced pressure. 888 mg of the desired compound were obtained.

LC-MS rt: 1.59 min [M+H]⁺: 407.9

23c) N-[3-[2-(5,6-Diethoxy-7-fluoro-1-imino-1,3-dihydroisoindol-2-yl)acetyl]-5-(pentafluorosulfanyl)phenyl]cyclopropanecarboxamide as the hydrochloride 5,6-Diethoxy-7-fluoro-3H-isoindol-1-ylamine (150 mg, prepared according to EP 1391451 or CA 2515715) and N-[3-(2-bromoacetyl)-5-pentafluorosulfanylphenyl]cyclopropylamide (283 mg) were stirred at RT in absolute DMF (5 ml) for 4 h and the reaction mixture was left to stand overnight. The solvent was removed under reduced pressure and the residue was purified by preparative HPLC twice and subsequent chromatography using silica gel with methylene chloride/ethanol. The product-containing fractions were combined, freed of the solvent and freeze-dried. For conversion to the hydrochloride, the residue was freeze-dried with two equivalents of 1N hydrochloric acid. 57 mg of the title compound were obtained.

LC-MS rt: 1.26 min [M+H]⁺: 566.1

Example 24

2-(5,6-Diethoxy-7-fluoro-1-imino-1,3-dihydroisoindol-2-yl)-1-[3-ethoxy-5-(pentafluorosulfanyl)phenyl]ethanone as the hydrobromide

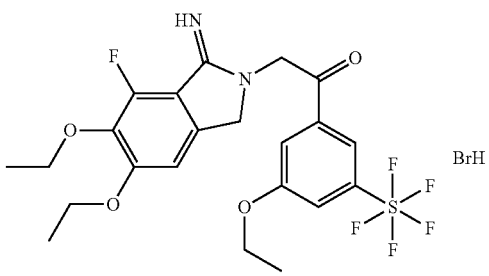 [SMILES: CCOc1cc(C(=O)CN2Cc3cc(OCC)c(OCC)c(F)c3C2=N)cc(S(F)(F)(F)(F)F)c1 ; Br]

24a) Ethyl 3-ethoxy-5-(pentafluorosulfanyl)benzoate

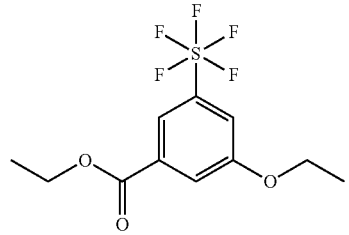 [SMILES: CCOC(=O)c1cc(OCC)cc(S(F)(F)(F)(F)F)c1]

3-Hydroxy-5-(pentafluorosulfanyl)benzoic acid (4.76 g; example 21a) was reacted analogously to example 21b) with ethyl iodide (7.27 ml) in the presence of potassium carbonate. 4.8 g of the title compound were obtained.

LC-MS rt: 1.97 min [M+H]⁺: 321.0

24b) 3-Ethoxy-N-methoxy-N-methyl-5-(pentafluorosulfanyl)benzamide

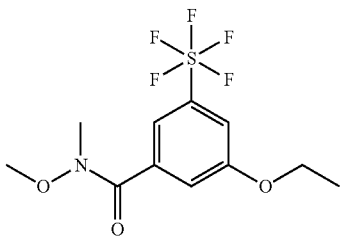 [SMILES: CCOc1cc(C(=O)N(C)OC)cc(S(F)(F)(F)(F)F)c1]

Ethyl 3-ethoxy-5-(pentafluorosulfanyl)benzoate (4.8 g) was dissolved in THF (150 ml) and admixed with N,O-dimethylhydroxylamine hydrochloride (2.20 g). The mixture was cooled to approx. −15° C. under argon, and isopropylmagnesium chloride (22.5 ml, 2 M in THF) was added dropwise within 10 min. After stirring at −15° C. for 20 min, the cooling bath was removed and the mixture was stirred at RT for another 1 h. Then saturated ammonium chloride solution was added and the mixture was extracted three times with EA. The combined organic phases were dried over magnesium sulfate, filtered and concentrated. The residue was purified using silica gel (120 g cartridge, n-heptane/MtB ether gradient of 20-100% within 60 min). 2.80 g of the title compound were obtained.

LC-MS rt: 1.60 min [M+H]$^+$: 336.0

24c)
1-[3-Ethoxy-5-(pentafluorosulfanyl)phenyl]ethanone

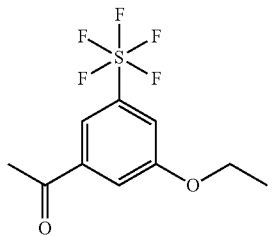 [SMILES: CCOc1cc(C(C)=O)cc(S(F)(F)(F)(F)F)c1]

3-Ethoxy-N-methoxy-N-methyl-5-(pentafluorosulfanyl)benzamide (2.6 g) was dissolved in THF (60 ml). After cooling to 0° C., methylmagnesium bromide (6.46 ml, 3 M in ether) was added dropwise. Thereafter, the cooling bath was removed and stirring was continued at RT. After 1 h, the mixture was acidified with 1N hydrochloric acid, admixed with water and extracted by shaking twice with EA. The EA phases were dried over magnesium sulfate, filtered and concentrated. 2.25 g of the title compound were obtained.

LC-MS rt: 1.72 min [M+H]$^+$: 291.0

24d) 2-Bromo-1-[3-ethoxy-5-(pentafluorosulfanyl)phenyl]ethanone

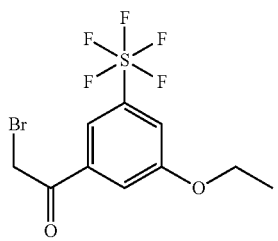 [SMILES: CCOc1cc(C(=O)CBr)cc(S(F)(F)(F)(F)F)c1]

1-[3-Ethoxy-5-(pentafluorosulfanyl)phenyl]ethanone (2.07 g) was dissolved in THF (80 ml) and phenyltrimethylammonium tribromide (2.90 g) was added while stirring. After stirring at RT for 3 h, the mixture was diluted with DCM and washed once with 5% sodium thiosulfate solution. The DCM phase was dried over magnesium sulfate, filtered and concentrated. The residue was purified using silica gel (120 g cartridge, n-heptane/MtB ether gradient of 0-20% within 60 min). 2.07 g of the title compound were obtained.

LC-MS rt: 1.83 min [M+H]$^+$: 368.9

24e) 2-(5,6-Diethoxy-7-fluoro-1-imino-1,3-dihydroisoindol-2-yl)-1-[3-ethoxy-5-(pentafluorosulfanyl)phenyl]ethanone as the hydrobromide 5,6-Diethoxy-7-fluoro-3H-isoindol-1-ylamine (30 mg, prepared according to EP 1391451 or CA 2515715) was suspended in THF (5 ml). After stirring at RT for 5 min, 2-bromo-1-[3-ethoxy-5-(pentafluorosulfanyl)phenyl]ethanone (46 mg, dissolved in 5 ml of THF) was added dropwise. After stirring at RT for 7 h, the mixture was left to stand overnight and the precipitate was then filtered off with suction. After drying under high vacuum, 29 mg of the title compound were obtained.

Preparative HPLC purification of the mother liquor afforded, after freeze-drying, a further 15 mg in the form of the trifluoroacetic acid salt.

LC-MS rt: 1.33 min [M+H]$^+$: 527.2

Example 25

N-Methyl-6-ethoxy-3-imino-2-{2-[3-methoxy-5-(pentafluorosulfanyl)phenyl]-2-oxoethyl}-2,3-dihydro-1H-isoindole-5-carboxamide as the trifluoroacetic acid salt

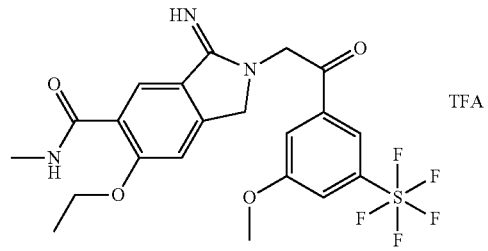 [SMILES: CCOc1cc2c(cc1C(=O)NC)C(=N)N(CC(=O)c1cc(OC)cc(S(F)(F)(F)(F)F)c1)C2]

N-Methyl-3-amino-6-ethoxy-1H-isoindole-5-carboxamide (20 mg, purchased from Chembiotek) was reacted with 2-bromo-1-[3-methoxy-5-(pentafluorosulfanyl)phenyl]ethanone (31 mg, example 21e), worked up and purified analogously to example 12). 25 mg of the title compound were obtained.

LC-MS rt: 1.19 min [M+H]$^+$: 508.0

Example 26

1-[3-Bromo-5-(pentafluorosulfanyl)phenyl]-2-(5,6-diethoxy-7-fluoro-1-imino-1,3-dihydroisoindol-2-yl)ethanone as the trifluoroacetic acid salt

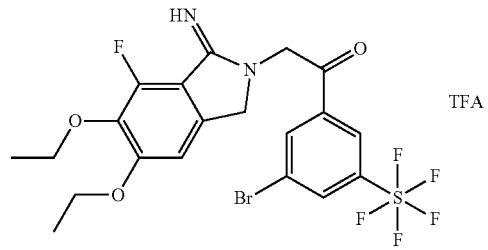 [SMILES: CCOc1cc2c(c(F)c1OCC)C(=N)N(CC(=O)c1cc(Br)cc(S(F)(F)(F)(F)F)c1)C2]

26a) 3-Bromo-5-(pentafluorosulfanyl)benzoic acid

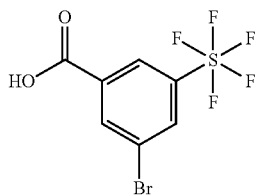

3-Amino-5-(pentafluorosulfanyl)benzoic acid (1.1 g; example 2a) was dissolved in 24% hydrogen bromide solution (40 ml). While stirring and cooling, sodium nitrite solution (290 mg dissolved in 20 ml of water) was added dropwise, in the course of which the temperature was not to exceed 5° C. On completion of formation of the diazonium salt, copper(I) bromide solution (720 mg dissolved in 15 ml of 48% hydrobromic acid) was cooled to 0° C. while stirring and the above diazonium salt solution was slowly added dropwise. Then the cooling bath was removed and the mixture was stirred at RT for 3 h. Thereafter, the reaction mixture was diluted with water and extracted repeatedly with EA. The combined EA phases were dried over magnesium sulfate, filtered and concentrated. The residue was dissolved in 500 ml of EA and filtered through a glass frit filled with a 10 cm silica gel layer. The filter layer was washed thoroughly with EA. The clear filtrate was concentrated, and solvent residues were drawn off under high vacuum. 800 mg of the title compound were obtained.

Further product was obtained by washing the silica gel with 550 ml of a DCM/methanol mixture (10:1). After concentrating and drying, a further 550 mg of product were thus isolated.

$^1$H NMR (400 MHz, DMSO-$d_6$) [ppm]: 8.46 (1H); 8.32 (1H); 8.25 (1H)

26b) 3-Bromo-N-methoxy-N-methyl-5-(pentafluorosulfanyl)benzamide

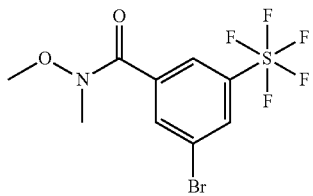 [SMILES: CON(C)C(=O)c1cc(Br)cc(S(F)(F)(F)(F)F)c1]

3-Bromo-5-(pentafluorosulfanyl)benzoic acid (1.35 g) was dissolved in thionyl chloride (10 ml) while stirring, and kept under reflux with exclusion of moisture for 5 h. Then the thionyl chloride was drawn off, the residue was taken up in DCM (40 ml) and the solution was admixed with N,O-dimethylhydroxylamine hydrochloride (381 mg). Subsequently Hünig's base (0.7 ml) was added and then the mixture was stirred for 2 h. Thereafter, the mixture was dried, the residue was taken up with EA and the solution was washed five times with water. The EA phase was dried over magnesium sulfate, filtered and concentrated. The residue was purified using silica gel (60 g cartridge, 4:1 n-heptane/EA). 1.1 g of the title compound were obtained.

LC-MS rt: 1.13 min [M+H]$^+$: 370.0 (met. b)

26c) 1-[3-Bromo-5-(pentafluorosulfanyl)phenyl]ethanone

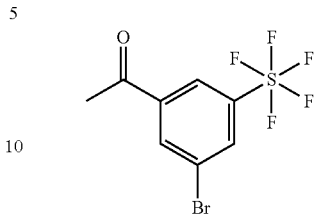

3-Bromo-N-methoxy-N-methyl-5-(pentafluorosulfanyl)benzamide (1.1 g) was converted and worked up analogously to 21d). Purification by means of HPLC was not necessary. 935 mg of the title compound were obtained.

LC-MS rt: 1.18 min [M+H]$^+$: 324.9 (met. b)

26d) 2-Bromo-1-[3-bromo-5-(pentafluorosulfanyl)phenyl]ethanone

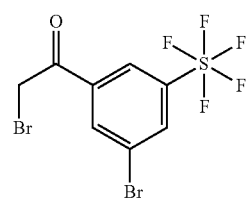 [SMILES: O=C(CBr)c1cc(Br)cc(S(F)(F)(F)(F)F)c1]

1-[3-Bromo-5-(pentafluorosulfanyl)phenyl]ethanone (50 mg) was initially charged dissolved in glacial acetic acid (3 ml), and bromine (50 µl of a solution of 475 mg of bromine in 1 ml of glacial acetic acid) was slowly added dropwise. After stirring at RT for 30 min, the mixture was heated to 60° C. for 3 h and then a further 15 µl of the bromine solution were added. After 2 h, the mixture was left to stand overnight, then heated again to 60° C., and a further 10 µl of the bromine solution were added. After 1 h, the mixture was diluted with toluene and dried. The residue was purified by means of preparative HPLC, and the product-containing fractions were combined, freed of the acetonitrile, alkalized with saturated sodium hydrogencarbonate solution and extracted three times with EA. The combined EA phases were dried over magnesium sulfate, filtered and concentrated. 16 mg of the title compound were obtained.

$^1$H NMR (400 MHz, DMSO-$d_6$) [ppm]: 8.50 (1H); 8.48 (1H); 8.33 (1H); 5.08 (2H)

26e) 1-[3-Bromo-5-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (18 mg, prepared according to EP 1391451 or CA 2515715) was suspended in THF (2 ml). After stirring at RT for 5 min, 2-bromo-1-[3-bromo-5-(pentafluorosulfanyl)phenyl]ethanone (30 mg, dissolved in 2 ml of THF) was added dropwise. After stirring at RT for 5 h, the mixture was left to stand overnight and then the solvent was drawn off. The residue was purified by means of preparative HPLC and then the product-containing fractions were combined, freed of the acetonitrile and freeze-dried. 7.5 mg of the title compound were obtained.
LC-MS rt: 1.33 min [M+H]+: 561.0

Example 27

1-[3-Chloro-5-(pentafluorosulfanyl)phenyl]-2-(5,6-diethoxy-7-fluoro-1-imino-1,3-dihydroisoindol-2-yl) ethanone as the trifluoroacetic acid salt

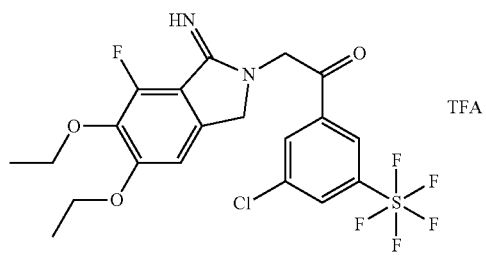 [SMILES: CCOc1cc2c(c(F)c1OCC)C(=N)N(CC(=O)c1cc(Cl)cc(S(F)(F)(F)(F)F)c1)C2]

27a)
1-[3-Chloro-5-(pentafluorosulfanyl)phenyl]ethanone

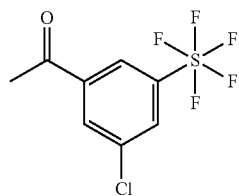 [SMILES: CC(=O)c1cc(Cl)cc(S(F)(F)(F)(F)F)c1]

1-[3-Amino-5-(pentafluorosulfanyl)phenyl]ethanone (150 mg, ex. 22a) was dissolved in semiconcentrated hydrochloric acid (6 ml). While stirring and cooling, sodium nitrite solution (40 mg dissolved in water) was added dropwise, in the course of which the temperature was not to exceed 5° C. On completion of formation of the diazonium salt, copper(I) chloride solution (68 mg dissolved in 2 ml of concentrated hydrochloric acid) was cooled to 0° C. while stirring and the above diazonium salt solution was slowly added dropwise. Then the cooling bath was removed, and the mixture was stirred at RT for 3 h and left to stand overnight. Then the reaction mixture was diluted with water and extracted repeatedly with EA. The combined EA phases were washed with saturated sodium hydrogencarbonate solution, dried over magnesium sulfate, filtered and concentrated. The residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 104 mg of the desired compound were obtained.

$^1$H NMR (400 MHz, DMSO-$d_6$) [ppm]: 8.38 (1H); 8.32 (1H); 8.22 (1H); 2.67 (3H)

27b) 2-Bromo-1-[3-chloro-5-(pentafluorosulfanyl) phenyl]ethanone

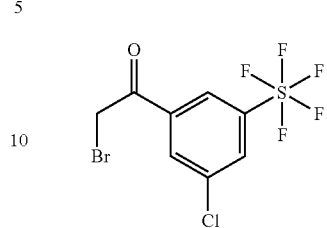

1-[3-Chloro-5-(pentafluorosulfanyl)phenyl]ethanone (100 mg) was converted, worked up and isolated analogously to example 26d). 60 mg of the title compound were obtained.
LC-MS rt: 1.80 min [M+H]+: 358.9

27c) 1-[3-Chloro-5-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (20 mg, prepared according to EP 1391451 or CA 2515715) and 2-bromo-1-[3-chloro-5-(pentafluorosulfanyl)phenyl]ethanone (30 mg) were converted analogously to example 26e). 15 mg of the title compound were obtained.
LC-MS rt: 1.32 min [M+H]+: 517.0

Example 28

1-[2-Bromo-4-(pentafluorosulfanyl)phenyl]-2-(5,6-diethoxy-7-fluoro-1-imino-1,3-dihydroisoindol-2-yl) ethanone as the trifluoroacetic acid salt

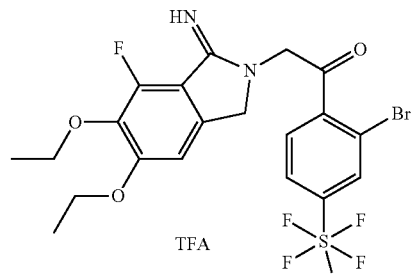

28a) 1-[2-Bromo-4-(pentafluorosulfanyl)phenyl] ethanone and 2-bromo-1-[2-bromo-4-(pentafluorosulfanyl)phenyl]ethanone

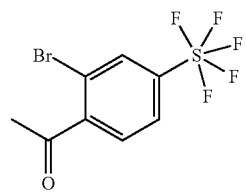

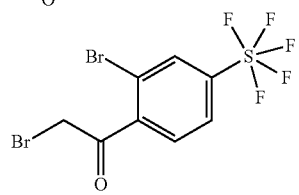

1-[2-Amino-4-(pentafluorosulfanyl)phenyl]ethanone (130 mg, example 19d) was dissolved in 24% hydrogen bromide solution (6 ml). While stirring and cooling, sodium nitrite solution (35 mg dissolved in 3 ml of water) was added dropwise. On completion of formation of the diazonium salt, copper(I) bromide solution (86 mg dissolved in 2 ml of 48% hydrobromic acid) was cooled to 0° C. while stirring and the above diazonium salt solution was slowly added dropwise. Then the cooling bath was removed and the mixture was stirred at RT for 5 h and left to stand over the weekend. Thereafter, the mixture was heated to 50° C. for 4 h. After cooling, the reaction mixture was diluted with water and extracted repeatedly with EA. The combined EA phases were washed with saturated sodium hydrogencarbonate solution, dried over magnesium sulfate, filtered and concentrated. The residue was purified by means of prepative HPLC. The particular product-containing fractions were combined, freed of the acetonitrile, admixed with saturated sodium hydrogencarbonate solution and extracted three times with ethyl acetate. The combined extracts were dried over magnesium sulfate, filtered and concentrated. 36 mg of 1-[2-bromo-4-(pentafluorosulfanyl)phenyl]ethanone and 36 mg of 2-bromo-1-[2-bromo-4-(pentafluorosulfanyl)phenyl]ethanone were obtained. 1-[2-Bromo-4-(pentafluorosulfanyl)phenyl]ethanone $^1$H NMR (400 MHz, DMSO-$d_6$) [ppm]: 8.28 (1H); 8.08 (1H); 7.86 (1H); 2.60 (3H)

2-Bromo-1-[2-bromo-4-(pentafluorosulfanyl)phenyl]ethanone $^1$H NMR (400 MHz, DMSO-$d_6$) [ppm]: 8.34 (1H); 8.14 (1H); 7.98 (1H); 4.90 (2H)

28b) 1-[2-Bromo-4-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (20 mg, prepared according to EP 1391451 or CA 2515715) and 2-bromo-1-[2-bromo-4-(pentafluorosulfanyl)phenyl]ethanone (34 mg) were converted, worked up and purified analogously to example 26e). 11 mg of the title compound were obtained.

LC-MS rt: 1.33 min [M+H]$^+$: 561.0

Example 29

1-[2-Chloro-4-(pentafluorosulfanyl)phenyl]-2-(5,6-diethoxy-7-fluoro-1-imino-1,3-dihydroisoindol-2-yl)ethanone as the trifluoroacetic acid salt

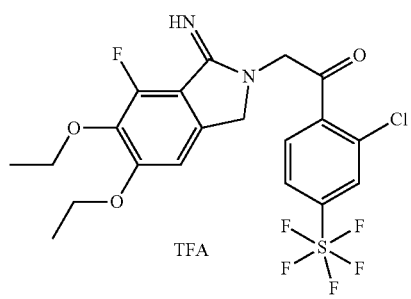 [SMILES: CCOc1cc2c(c(F)c1OCC)C(=N)N(CC(=O)c1ccc(S(F)(F)(F)(F)F)cc1Cl)C2]

29a)
1-[2-Chloro-4-(pentafluorosulfanyl)phenyl]ethanone

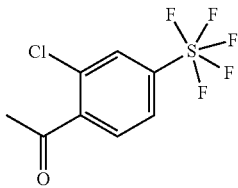 [SMILES: CC(=O)c1ccc(S(F)(F)(F)(F)F)cc1Cl]

1-[2-Amino-4-(pentafluorosulfanyl)phenyl]ethanone (170 mg, example 19d) was converted, worked up and purified analogously to example 27a). 86 mg of the title compound were obtained.

$^1$H NMR (400 MHz, DMSO-$d_6$) [ppm]: 8.18 (1H); 8.04 (1H); 7.90 (1H); 2.61 (3H)

29b) 2-Bromo-1-[2-chloro-4-(pentafluorosulfanyl)phenyl]ethanone

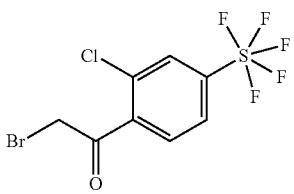 [SMILES: O=C(CBr)c1ccc(S(F)(F)(F)(F)F)cc1Cl]

1-[2-Chloro-4-(pentafluorosulfanyl)phenyl]ethanone (70 mg) was brominated analogously to example 8b). However, the mixture was stirred in the 2N sulfuric acid at 50° C. for 4 h. 31 mg of the title compound were obtained.

$^1$H NMR (400 MHz, DMSO-$d_6$) [ppm]: 8.25 (1H); 8.10 (1H); 8.03 (1H); 4.91 (2H)

29c) 1-[2-Chloro-4-(pentafluorosulfanyl)phenyl]-2-(5,6-diethoxy-7-fluoro-1-imino-1,3-dihydroisoindol-2-yl)ethanone as the trifluoroacetic acid salt 5,6-Diethoxy-7-fluoro-3H-isoindol-1-ylamine (19 mg, prepared according to EP 1391451 or CA 2515715) and 2-bromo-1-[2-chloro-4-(pentafluorosulfanyl)phenyl]ethanone (29 mg) were converted analogously to example 26e). 18 mg of the title compound were obtained.

LC-MS rt: 1.30 min [M+H]$^+$: 517.0

Example 30

2-(5,6-Diethoxy-7-fluoro-1-imino-1,3-dihydroisoindol-2-yl)-1-[3-morpholin-4-yl-5-(pentafluorosulfanyl)phenyl]ethanone as the trifluoroacetic acid salt

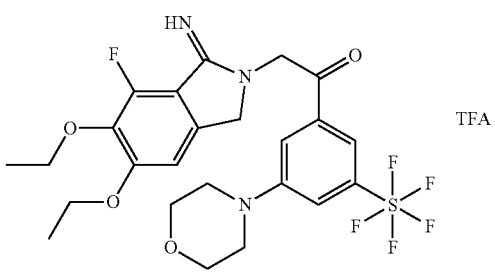 [SMILES: CCOc1cc2c(c(F)c1OCC)C(=N)N(CC(=O)c1cc(N3CCOCC3)cc(S(F)(F)(F)(F)F)c1)C2]

30a) N-Methoxy-N-methyl-3-morpholin-4-yl-5-(pentafluorosulfanyl)benzamide

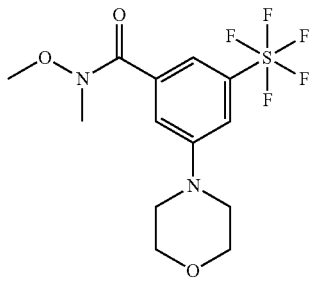 [SMILES: CON(C)C(=O)c1cc(N2CCOCC2)cc(S(F)(F)(F)(F)F)c1]

3-Amino-N-methoxy-N-methyl-5-(pentafluorosulfanyl) benzamide (6.3 g, example 4b) was dissolved in DMF (80 ml), and cesium carbonate (10.1 g), sodium iodide (0.62 g) and bis(2-bromoethyl)ether (19.37 g) were added. The mixture was divided between 10 microwave vessels, each of which was heated in the microwave to 130° C. for 3 h. Subsequently, the batches were combined and freed of the solvent. The residue was taken up in EA and washed with water. The EA phase was dried and concentrated. The residue was purified using silica gel (120 g cartridge, n-heptane/EA gradient of 0-100% within 30 min). 2.48 g of the title compound were obtained.

LC-MS rt: 1.41 min [M+H]$^+$: 377.0

30b) 1-[3-Morpholin-4-yl-5-(pentafluorosulfanyl) phenyl]ethanone

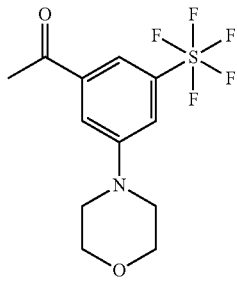 [SMILES: CC(=O)c1cc(N2CCOCC2)cc(S(F)(F)(F)(F)F)c1]

N-Methoxy-N-methyl-3-morpholin-4-yl-5-(pentafluorosulfanyl)benzamide (2.38 g) was dissolved in THF (50 ml), methylmagnesium bromide (4.22 ml, 3 M in ether) was added dropwise at 0° C. and then the mixture was stirred at RT for 2 h. Then 1N hydrochloric acid (100 ml) was added, and the mixture was diluted with water and extracted by shaking three times with EA. Thereafter, the combined EA phases were dried over magnesium sulfate, filtered and concentrated. The residue was purified using silica gel (80 g cartridge, n-heptane/EA gradient of 0-70% within 40 min). 1.1 g of the title compound were obtained.

LC-MS rt: 1.57 min [M+H]$^+$: 332.0

30c) 2-Bromo-1-[3-morpholin-4-yl-5-(pentafluorosulfanyl)phenyl]ethanone

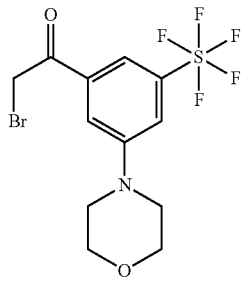 [SMILES: O=C(CBr)c1cc(N2CCOCC2)cc(S(F)(F)(F)(F)F)c1]

1-[3-Morpholin-4-yl-5-(pentafluorosulfanyl)phenyl]ethanone (1.1 g) was dissolved in methanol/THF (20/20 ml), and phenyltrimethylammonium tribromide (1.25 g) was added while stirring. After stirring at RT for 27 h, 20% citric acid (50 ml) was added and the mixture was stirred for 1 h. After adding DCM (100 ml), the DCM phase was removed, dried and concentrated. The residue was dissolved in acetonitrile (100 ml), and 2N sulfuric acid (20 ml) was added to the solution. After stirring at RT for 24 h, water was added and the mixture was extracted with EA. The EA phase was washed with saturated sodium hydrogencarbonate solution, dried and concentrated. The residue was purified using silica gel (80 g cartridge, n-heptane/EA gradient of 0-60% within 40 min). 866 mg of the title compound were obtained.

LC-MS rt: 1.69 min [M+H]$^+$: 410.0

30d) 2-(5,6-Diethoxy-7-fluoro-1-imino-1,3-dihydroisoindol-2-yl)-1-[3-morpholin-4-yl-5-(pentafluorosulfanyl)phenyl]ethanone as the trifluoroacetic acid salt 5,6-Diethoxy-7-fluoro-3H-isoindol-1-ylamine (9 mg, prepared according to EP 1391451 or CA 2515715) and 2-bromo-1-[3-morpholin-4-yl-5-(pentafluorosulfanyl)phenyl]ethanone (15 mg) were converted, worked up and purified analogously to example 26e). 15 mg of the title compound were obtained.

LC-MS rt: 0.97 min [M+H]$^+$: 568.2 (met. b)

Example 31

2-(5,6-Diethoxy-7-fluoro-1-imino-1,3-dihydroisoindol-2-yl)-1-[3-(2-methoxyethoxy)-5-(pentafluorosulfanyl)phenyl]ethanone hydrochloride

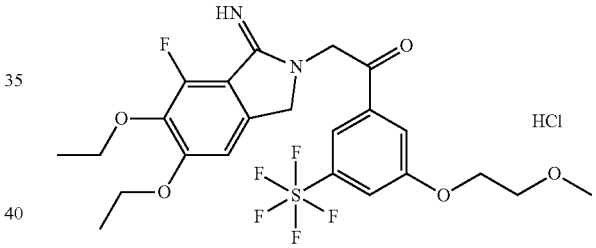

31a) 1-[3-Amino-5-(pentafluorosulfanyl)phenyl]ethanone

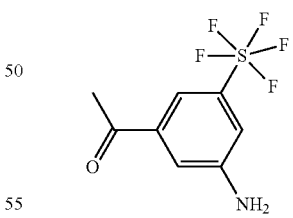

N-(3-Acetyl-5-pentafluorosulfanylphenyl)-2,2,2-trifluoroacetamide (9.4 g, example 4d) was admixed with semiconcentrated sulfuric acid (200 ml), and DCM (15 ml) was added for dissolution. After stirring at 100° C. for 7 h, the mixture was left to stand overnight. Then the mixture was added to ice-water and extracted with EA. The combined EA phases were washed with saturated sodium hydrogencarbonate solution, dried over magnesium sulfate, filtered and concentrated by rotary evaporation. 6.36 g of the title compound were obtained.

LC-MS rt: 1.38 min [M+H]$^+$: 262.0

31b) 1-[3-Hydroxy-5-(pentafluorosulfanyl)phenyl]ethanone

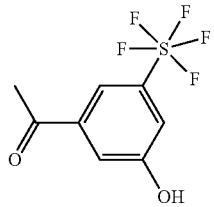 [SMILES: CC(=O)c1cc(O)cc(S(F)(F)(F)(F)F)c1]

1-[3-Amino-5-(pentafluorosulfanyl)phenyl]ethanone (3.00 g) was dissolved while heating in 35% aqueous sulfuric acid (25 ml). The solution was cooled to −5° C. and a solution of sodium nitrite (780 mg) in 15 ml of water was added dropwise within 10 min. After 40 min at −5° C., the cooling bath was removed and the mixture was heated to 100° C. for 2 h. After cooling, the mixture was extracted twice with EA. The combined EA phases were washed with saturated sodium hydrogencarbonate solution, dried, filtered and concentrated. The residue was purified using silica gel (80 g cartridge, n-heptane/MtB ether gradient of 0-100% within 40 min). 1.62 g of the title compound were obtained.

$^1$H NMR (500 MHz, DMSO-$d_6$) [ppm]: 10.71 (1H); 7.73 (1H); 7.59 (1H); 7.47 (1H); 2.61 (3H)

31c) 1-[3-(2-Methoxyethoxy)-5-(pentafluorosulfanyl)phenyl]ethanone

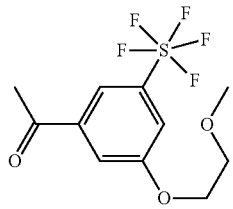 [SMILES: COCCOc1cc(C(C)=O)cc(S(F)(F)(F)(F)F)c1]

1-[3-Hydroxy-5-(pentafluorosulfanyl)phenyl]ethanone (592 mg) and 1-bromo-2-methoxyethane (255 μl) were dissolved in DMF (14.8 ml), and sodium hydride (65 mg) was added. After stirring at RT for 2 h, further bromide (80 μl) was added and the mixture was heated to 50° C. for 12 h. Then the DMF was drawn off and the residue was taken up in EA, washed with water, dried, filtered and concentrated. 578 mg of the title compound were obtained.

LC-MS rt: 1.58 min [M+H]$^+$: 321.1

31d) 2-Bromo-1-[3-(2-methoxyethoxy)-5-(pentafluorosulfanyl)phenyl]ethanone

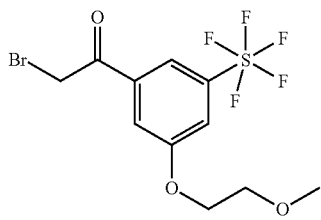 [SMILES: COCCOc1cc(C(=O)CBr)cc(S(F)(F)(F)(F)F)c1]

1-[3-(2-Methoxyethoxy)-5-(pentafluorosulfanyl)phenyl]ethanone (578 mg) was brominated analogously to example 30c). 290 mg of the title compound were obtained.

LC-MS rt: 1.70 min [M+H]$^+$: 399.0

31e) 2-(5,6-Diethoxy-7-fluoro-1-imino-1,3-hydroisoindol-2-yl)-1-[3-(2-methoxyethoxy)-5-(pentafluorosulfanyl)phenyl]ethanone hydrochloride 5,6-Diethoxy-7-fluoro-3H-isoindol-1-ylamine (25 mg, prepared according to EP 1391451 or CA 2515715) and 2-bromo-1-[3-(2-methoxyethoxy)-5-(pentafluorosulfanyl)phenyl]ethanone (43 mg) were converted, worked up and purified analogously to example 26e). 37 mg of the title compound were obtained.

LC-MS rt: 0.97 min [M+H]$^+$: 568.2 (met. b)

Example 32

2-(5,6-Diethoxy-7-fluoro-1-imino-1,3-dihydroisoindol-2-yl)-1-[3-ethoxy-5-(pentafluorosulfanyl)phenyl]propan-1-one as the trifluoroacetic acid salt

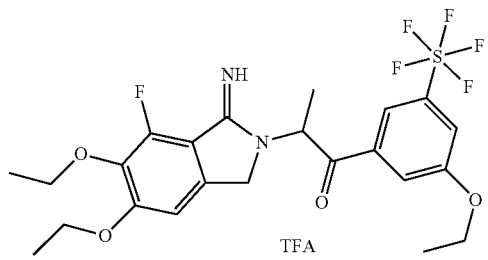 [SMILES: CCOc1cc(C(=O)C(C)N2Cc3cc(OCC)c(OCC)c(F)c3C2=N)cc(S(F)(F)(F)(F)F)c1]

32a) 1-[3-Ethoxy-5-(pentafluorosulfanyl)phenyl]propan-1-one

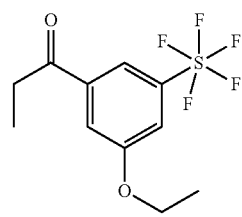 [SMILES: CCOc1cc(C(=O)CC)cc(S(F)(F)(F)(F)F)c1]

3-Ethoxy-N-methoxy-N-methyl-5-(pentafluorosulfanyl)benzamide (170 mg, example 24b) was dissolved in absolute THF (5 ml), and ethylmagnesium bromide (0.65 ml; 2 M in diethyl ether) was added dropwise at 0° C. while stirring. After addition, the ice bath was removed and the mixture was stirred at RT for 2 h. Then further ethylmagnesium bromide (0.1 ml) was added and the mixture was stirred once again for 2 h. Subsequently, 1N hydrochloric acid was added dropwise while cooling, followed by water and ethyl acetate. The organic phase was removed and the aqueous phase was extracted twice with ethyl acetate. The combined extracts were dried over magnesium sulfate, filtered and concentrated. 150 mg of the desired compound were obtained.

LC-MS rt: 1.26 min [M+H]$^+$: 305.1 (met. b)

32b) 2-Bromo-1-[3-ethoxy-5-(pentafluorosulfanyl) phenyl]propan-1-one

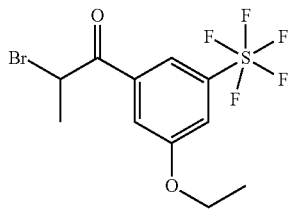 [SMILES: CCOc1cc(C(=O)C(C)Br)cc(S(F)(F)(F)(F)F)c1]

1-[3-Ethoxy-5-(pentamethylsulfanyl)phenyl]propan-1-one (150 mg) was dissolved in THF (15 ml), and phenyltrimethylammonium tribromide (185 mg) was added at RT while stirring. After stirring at RT for 5 h, water, saturated sodium hydrogencarbonate solution and EA were added. The EA phase was removed and the alkaline water phase was extracted three times with EA. The combined organic phases were washed once with saturated sodium chloride solution, dried over magnesium sulfate, filtered and concentrated. The crude product was purified by means of preparative HPLC. The clean product fractions were combined, freed of the acetonitrile under reduced pressure, alkalyzed with saturated sodium hydrogencarbonate solution and extracted five times with EA. The combined organic phases were dried over magnesium sulfate and, after filtering off the desiccant, dried under reduced pressure. 120 mg of the title compound were isolated.

LC-MS rt: 1.29 min [M+H]$^+$: 383.0 (met. b)

32c) 2-(5,6-Diethoxy-7-fluoro-1-imino-1,3-dihydroisoindol-2-yl)-1-[3-ethoxy-5-(pentafluorosulfanyl)phenyl]propan-1-one as the trifluoroacetic acid salt 5,6-Diethoxy-7-fluoro-3H-isoindol-1-ylamine (5 mg, prepared according to EP 1391451 or CA 2515715) was suspended in THF (5 ml) and, after stirring at RT for 5 min, 2-bromo-1-[3-ethoxy-5-(pentafluorosulfanyl)phenyl]propan-1-one (40 mg, dissolved in 3 ml of THF) was added dropwise. After stirring at RT for 12 h, the mixture was admixed with water and EA, and the phases were separated. The water phase was extracted three times with EA. The combined EA phases were purified by means of preparative HPLC, and the product-containing fractions were combined, freed of the acetonitrile and freeze-dried. For further purification, the residue was passed through silica gel (40:1 DCM/methanol). The combined clean fractions were dried, taken up with ACN/water (with 0.05% TFA) and freeze-dried. 6 mg of the title compound were obtained.

LC-MS rt: 1.04 min [M+H]$^+$: 541.2 (met. b)

Example 33

2-(5,6-Diethoxy-7-fluoro-1-imino-1,3-dihydroisoindol-2-yl)-1-[3-(pentafluorosulfanyl)-5-pyrrolidin-1-ylphenyl]ethanone as the trifluoroacetic acid salt

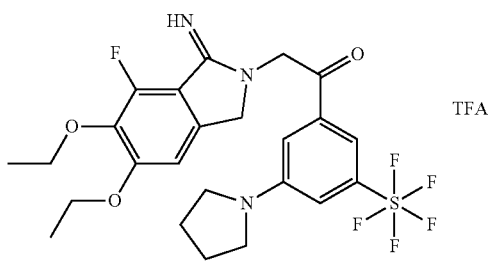 [SMILES: CCOc1cc2c(c(F)c1OCC)C(=N)N(CC(=O)c1cc(N3CCCC3)cc(S(F)(F)(F)(F)F)c1)C2]

TFA

33a) 1-Bromo-3-(1,1-dimethoxyethyl)-5-(pentafluorosulfanyl)benzene

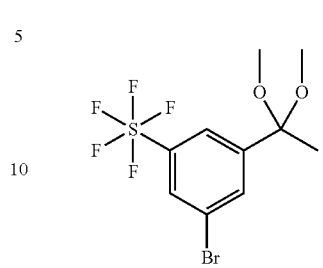

1-[3-Bromo-5-(pentafluorosulfanyl)phenyl]ethanone (835 mg, example 26c) was dissolved in methanol (50 ml), and admixed at RT with DL-10-camphorsulfonic acid (0.9 mg) and with trimethyl orthoformate (0.85 ml). The reaction mixture was stirred at RT for 2 h and then stood overnight. Then the mixture was stirred at RT for a further 5 h. Subsequently, saturated sodium hydrogencarbonate solution was used to adjust the pH to 9, and a large amount of EA and water were added. The organic phase was removed and the aqueous phase was extracted five times with EA. The combined EA phases were dried over magnesium sulfate, filtered and concentrated. 900 mg of the title compound were obtained.

$^1$H NMR (400 MHz, DMSO-d$_6$) [ppm]: 8.14 (1H); 7.87 (1H); 7.81 (1H); 3.10 (6H); 1.50 (3H)

33b) 1-[3-(Pentafluorosulfanyl)-5-pyrrolidin-1-ylphenyl]ethanone

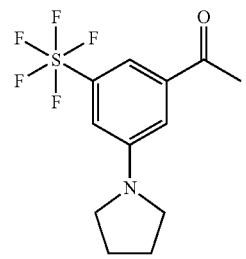 [SMILES: CC(=O)c1cc(N2CCCC2)cc(S(F)(F)(F)(F)F)c1]

1-Bromo-3-(1,1-dimethoxyethyl)-5-(pentafluorosulfanyl)benzene (200 mg) was initially charged at RT in DME (30 ml) under argon. Two drops of water were added to the DME. A strong argon stream was used to displace the oxygen from the solution for 45 min. Then pyrrolidine (45 µl) was added dropwise through a septum, followed by (+)-2,2'-bis(diphenylphosphino)-1,1'-binaphthalene (5 mg), sodium tert-butoxide (73 mg) and palladium(II) acetate (1.2 mg). The reaction mixture was heated to 85° C. for 3 h. Then EA was added to the reaction mixture and, after removing the EA phase, the aqueous phase was extracted three times with EA. The combined EA phases were dried over magnesium sulfate, filtered and concentrated. The residue was dissolved in ACN/water and adjusted to pH 2 with 1N hydrochloric acid. After standing for 30 min, the mixture was concentrated and the residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 55 mg of the desired compound were obtained.

LC-MS rt: 1.24 min [M+H]$^+$: 316.1 (met. b)

33c) 2-Bromo-1-[3-(pentafluorosulfanyl)-5-pyrrolidin-1-ylphenyl]ethanone

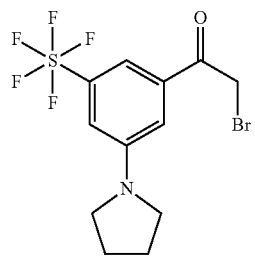 [SMILES: O=C(CBr)c1cc(N2CCCC2)cc(S(F)(F)(F)(F)F)c1]

1-[3-(Pentafluorosulfanyl)-5-pyrrolidin-1-ylphenyl]ethanone (78 mg) was dissolved in methanol (5 ml) and admixed while stirring with trimethyl orthoformate (80 mg) and DL-10-camphorsulfonic acid (57 mg). After stirring at RT for 3 h, THF (5 ml) was added, followed by phenyltrimethylammonium tribromide (83 mg). After stirring at RT for 3 h, the mixture was left to stand overnight. Then the mixture was heated to 50° C. for 3 h and subsequently dried. The residue was taken up in ACN, admixed with 2N sulfuric acid and stirred for 30 min. Then it was admixed with water and concentrated. The residue was purified by means of preparative HPLC. The product-containing fractions were combined, freed of the acetonitrile, admixed with saturated sodium hydrogencarbonate solution and extracted three times with ethyl acetate. The combined extracts were dried over magnesium sulfate, filtered and concentrated. 9 mg of the desired compound were obtained.

LC-MS rt: 1.23 min [M+H]$^+$: 394.0 (met. b)

33d) 2-(5,6-Diethoxy-7-fluoro-1-imino-1,3-dihydroisoindol-2-yl)-1-[3-(pentafluorosulfanyl)-5-pyrrolidin-1-ylphenyl]ethanone as the trifluoroacetic acid salt 5,6-Diethoxy-7-fluoro-3H-isoindol-1-ylamine (5 mg, prepared according to EP 1391451 or CA 2515715) and 2-bromo-1-[3-(pentafluorosulfanyl)-5-pyrrolidin-1-ylphenyl]ethanone (8 mg) were converted, worked up and purified analogously to example 26c). 5 mg of the title compound were obtained.

LC-MS rt: 1.05 min [M+H]$^+$: 552.2 (met. b)

Biological Examples

PAR1 Determination Method

Inhibition of PAR1-Mediated Platelet Aggregation

The biological testing of the substances took place in platelet aggregation induced by TRAP (thrombin receptor-activating peptide) in 96-well format. For this purpose, blood was taken from healthy volunteer donors in 20 ml syringes containing 2 ml of 3.13% sodium citrate solution. After centrifugation at 150×g for 20 minutes, the platelet-rich plasma (PRP) was separated off and admixed with 1 μl of PGE1 solution (500 μg/ml in ethanol)/ml of PRP. Incubation at RT for 5 minutes was followed by centrifugation at 120×g for 15 minutes to remove the leukocytes. The leukocyte-free PRP was transferred in 5 ml portions into 15 ml PP tubes and centrifuged at 360×g for 15 minutes in order to pellet the platelets. The plasma was then decanted off and the platelet sediment from 5 ml of PRP was resuspended in 1 ml of Tyrode's (120 mM NaCl, 2.6 mM KCl, 12 mM NaHCO$_3$, 0.39 mM NaH$_2$PO$_4$×H$_2$O, 10 mM HEPES, 0.35% BSA, 5.5 mM glucose, pH 7.4) and adjusted with Tyrode's to a platelet count of 3×10$^5$/microliter (μl). 13 ml of this cell suspension were then mixed with 866 μl of 10 mM CaCl$_2$ solution, and 120 μl thereof were pipetted into each well of a 96-well plate containing 15 μl of the substance to be tested. After incubation at RT in the dark for 30 minutes, 15 μl of a TRAP solution (70-100 μM) were added as agonist, and kinetics were recorded at 650 nm in a SpectraMax 340 at 37° C. for 20 minutes while shaking. The areas under the curves of negative control (Tyrode's/DMSO) and positive control (15 μl of agonist/DMSO) were calculated and the difference was fixed as the 100% value. The substances to be tested were pipetted as serial dilutions in duplicate determination, the AUC was likewise determined for each substance concentration, and the % inhibition of the AUC compared with the control was calculated. On the basis of the % inhibition, the IC$_{50}$ was calculated by nonlinear regression analysis according to the 4-parameter equation.

Table 1 shows the results.

TABLE 1

| Compound from example | Inhibition of platelet aggregation IC$_{50}$ [micro M] | Compound from example | Inhibition of platelet aggregation IC$_{50}$ [micro M] |
|---|---|---|---|
| 2 | 0.597 | 3 | 0.002 |
| 8 | 0.017 | 10 | 0.718 |
| 12 | 0.387 | 16 | 10.6 |
| 18 | 0.175 | 19 | 0.098 |
| 21 | 0.028 | | |

PAR1 Binding Test

The synthesized substances were examined in a PAR1 binding test. This tested whether the substances can inhibit the binding of a radioactively labeled PAR1 agonist known from the literature at the PAR1 receptor (Ho-Sam Ahn, Mol Pharm, 51:350-356, 1997).

The human PAR1 receptor was expressed transiently in High Five insect cells. From these cells, after 48 hours, a membrane preparation was produced by standard methods, aliquoted into 10 mM Tris-HCl; 0.3 mM EDTA; 1 mM EGTA; 250 mM sucrose pH 7.5, and stored at −80° C.

The substances were preincubated with the membrane at RT for 15 minutes, then the radioligand (ALA-(para-F-Phe)-Arg-ChA-homoArg-(3,4-$^3$H-Tyr)-NH$_2$; approx. 40 Ci/mMol) was added. The end concentration of the radioligand in the test buffer (50 mM Tris-HCl; 10 mM MgCl$_2$; 1 mM EGTA; 0.1% BSA; 2% DMSO) was 20 nM, that of the membrane 1 mg/ml. After an incubation time of 60 minutes, 25 μl of the mixture were transferred to a 96-well MultiScreenHTS FB microtiter filtration plate (from Millipore), which had been pretreated beforehand with a 0.75% aqueous polyethyleneimine solution for 5 hours at RT. Thereafter, with vacuum extraction, each well was washed four times with 300 μl of buffer (50 mM Tris-HCl; 10 mM MgCl$_2$; 1 mM EGTA). The plate was then dried overnight, 100 μl of scintillator per well were added, and the plate was analyzed after 6 hours in a Wallac MicroBeta (from PerkinElmer) liquid scintillation counter. The nonspecific binding was determined in the presence of 100 μM SCH79797 (PAR-1 antagonist; from Tocris, Cat. No. 1592) and subtracted from all measurements. The 100% value used was a control without inhibitor. The % inhibition values of a substance dilution series were used to calculate the IC$_{50}$ with the aid of nonlinear regression analysis according to the 4-parameter equation.

Table 2 shows the results.

TABLE 2

| Compound from example | Inhibition of binding IC$_{50}$ [micro M] |
| --- | --- |
| 4 | 4.80 |
| 14 | 0.227 |
| 17 | 0.360 |
| 20 | 0.128 |
| 24 | 0.512 |
| 27 | 1.7 |
| 30 | 0.225 |
| 34 | 0.268 |

What is claimed is:
1. A compound of formula I

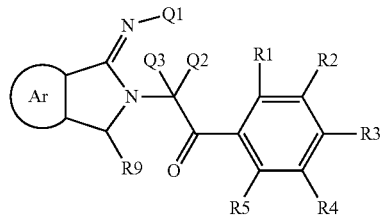

(I)

or a stereoisomeric or tautomeric form thereof, or a physiologically compatible salt of any of them, where Ar is a fused benzene, pyridine, pyrimidine, pyridazine or pyrazine ring, where the fused ring is unsubstituted or mono-, di-, tri- or tetrasubstituted independently by —(C$_1$-C$_6$)-alkyl, —(C$_3$-C$_6$)-cycloalkyl, —O—(C$_1$-C$_8$)-alkyl, —O—(C$_3$-C$_6$)-cycloalkyl, —(C$_0$-C$_4$)-alkylene-C(O)—N(R11)-R12, —(C$_0$-C$_4$)-alkylene-C(O)—O—R11, —(C$_0$-C$_4$)-alkylene-C(O)—R11, —(C$_0$-C$_4$)-alkylene-N(R11)-R12, —(C$_0$-C$_4$)-alkylene-N(R11)-C(O)—R12, halogen, OH, —CN, —NO$_2$, —SO$_2$CH$_3$, —SO$_2$CF$_3$, —SF$_5$, —Si[—(C$_1$-C$_4$)-alkyl]$_3$, —(C$_1$-C$_6$)-alkylene-O—(C$_1$-C$_6$)-alkyl, —(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl, —(C$_4$-C$_{15}$)-Het where Het is unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, or —O—(C$_1$-C$_6$)-alkylene-O—(C$_1$-C$_6$)-alkyl, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, —(C$_4$-C$_{15}$)-Het where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, or —O—(C$_3$-C$_6$)-cycloalkyl, where all or some of the hydrogen atoms in alkyl, alkylene or cycloalkyl may be replaced by fluorine, Q1 is a hydrogen atom, —(C$_1$-C$_6$)-alkyl, —(C$_3$-C$_6$)-cycloalkyl, —OH, —O—(C$_1$-C$_6$)-alkyl or —O—(C$_3$-C$_6$)-cycloalkyl, where alkyl and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where all or some of the hydrogen atoms in alkyl or cycloalkyl may be replaced by fluorine, Q2 and Q3 are the same or different and each independently a hydrogen atom, —(C$_1$-C$_6$)-alkyl or —(C$_3$-C$_6$)-cycloalkyl, where all or some of the hydrogen atoms in alkyl or cycloalkyl may be replaced by fluorine, R11 and R12 are each independently a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl, —(C$_0$-C$_4$)-alkylene-(C$_4$-C$_{15}$)-Het, —SO$_2$CH$_3$ or —SO$_2$CF$_3$, where all or some of the hydrogen atoms in alkyl, alkylene or cycloalkyl may be replaced by fluorine, or R11 and R12 in the "N(R11)-R12" and "N(R11)-C(O)—R12" fragments are a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where all or some of the hydrogen atoms in alkyl or cycloalkyl may be replaced by fluorine, R1, R2, R3, R4 and R5 are the same or different and are each independently a hydrogen atom, —(C$_1$-C$_6$)-alkyl, —(C$_3$-C$_6$)-cycloalkyl, OH, —CN, —NO$_2$, —O—(C$_1$-C$_6$)-alkyl, —O—(C$_3$-C$_6$)-cycloalkyl, —(C$_0$-C$_4$)-alkylene-(CO)—N(R21)-R22, —SO$_2$CH$_3$, —SO$_2$CF$_3$, —(C$_0$-C$_4$)-alkylene-C(O)—O—R21, halogen, —SF$_5$, —(C$_0$-C$_4$)-alkylene-C(O)—R21, —(C$_0$-C$_4$)-alkylene-N(R21)-R22, —(C$_0$-C$_4$)-alkylene-N(R21)-C(O)—R22, —(C$_1$-C$_6$)-alkylene-O—(C$_1$-C$_6$)-alkyl, —O—(C$_1$-C$_6$)-alkylene-O—(C$_1$-C$_6$)-alkyl, —(C$_6$-C$_{14}$)-aryl where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl, —Si[(C$_1$-C$_4$)-alkyl]$_3$ or —(C$_4$-C$_{15}$)-Het where Het is unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, —(C$_4$-C$_{15}$)-Het where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, or —O—(C$_3$-C$_6$)-cycloalkyl, where all or some of the hydrogen atoms in alkyl, alkylene or cycloalkyl may be replaced by fluorine, with the proviso that at least one R1, R2, R3, R4 or R5 is —SF$_5$, R9 is a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl, —($C_0$-$C_4$)-alkylene-($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments are a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

2. A compound as claimed in claim 1, where

Ar is a fused benzene or pyridine ring, where the fused ring is unsubstituted or mono-, di-, tri- or tetrasubstituted independently by —($C_1$-$C_6$)-alkyl, —($C_3$-$C_6$)-cycloalkyl, OH, —CN, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, $SO_2CH_3$, —($C_0$-$C_4$)-alkylene-N(R11)-R12, —($C_0$-$C_4$)-alkylene-N(R11)-C(O)—R12, halogen, —$SO_2CF_3$, —Si[($C_1$-$C_4$)-alkyl]$_3$, —($C_1$-$C_6$)-alkylene-O—($C_1$-$C_6$)-alkyl, —($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where all or some of the hydrogen atoms in alkyl, alkylene or cycloalkyl may be replaced by fluorine, Q1, Q2 and Q3 are the same or different and each independently a hydrogen atom, —($C_1$-$C_6$)-alkyl or —($C_3$-$C_6$)-cycloalkyl, where all or some of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl, —$SO_2CH_3$ or —$SO_2CF_3$, where all or some of the hydrogen atoms in alkyl or cycloalkyl may be replaced by fluorine, or R11 and R12 in the "N(R11)-R12" and "N(R11)-C(O)—R12" fragments are a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine, R1, R2, R3, R4 and R5 are the same or different and are each independently a hydrogen atom, —($C_1$-$C_6$)-alkyl, —($C_3$-$C_6$)-cycloalkyl, OH, —CN, —$NO_2$, —O—($C_1$-$C_6$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —O—($C_1$-$C_6$)-alkylene-O—($C_1$-$C_6$)-alkyl, —($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —Si[($C_1$-$C_4$)-alkyl]$_3$ or —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where all or some of the hydrogen atoms in alkyl, alkylene or cycloalkyl may be replaced by fluorine, with the proviso that at least one R1, R2, R3, R4 or R5 is —$SF_5$, R9 is a hydrogen atom, —($C_1$-$C_6$)-alkyl, —($C_3$-$C_6$)-cycloalkyl, —($C_0$-$C_4$)-alkylene-($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, or —($C_0$-$C_4$)-alkylene-($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments are a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

3. A compound as claimed in claim 1, where

Ar is a fused benzene or pyridine ring, where the fused ring is unsubstituted or mono-, di-, tri- or tetrasubstituted independently by —($C_1$-$C_6$)-alkyl, —($C_3$-$C_6$)-cycloalkyl, OH, —CN, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, $SO_2CH_3$, —($C_0$-$C_4$)-alkylene-N(R11)-R12, —($C_0$-$C_4$)-alkylene-N(R11)-C(O)—R12, halogen, —Si[($C_1$-$C_4$)-alkyl]$_3$, —($C_1$-$C_6$)-alkylene-O—($C_1$-$C_6$)-alkyl or —O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, OH, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where all or some of the hydrogen atoms in alkyl, alkylene or cycloalkyl may be replaced by fluorine, Q1, Q2 and Q3 are the same or different and each independently a hydrogen atom, —($C_1$-$C_6$)-alkyl or —($C_3$-$C_6$)-cycloalkyl, where all or some of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl or —$SO_2CH_3$, where all or some of the hydrogen atoms in alkyl, alkylene or cycloalkyl may be replaced by fluorine, or R11 and R12 in the "N(R11)-R12" and "N(R11)-C(O)—R12" fragments are a 5- to 8-membered ring which is selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where all or some of the hydrogen atoms in alkyl or cycloalkyl may be replaced by fluorine, R1, R2, R3, R4 and R5 are the same or different and are each independently a hydrogen atom, —($C_1$-$C_6$)-alkyl, —($C_3$-$C_6$)-cycloalkyl, OH, —CN, —$NO_2$, —O—($C_1$-$C_6$)-alkyl, —O—($C_3$-$C_6$)-cycloalkyl, —($C_0$-$C_4$)-alkylene-(CO)—N(R21)-R22, —$SO_2CH_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —O—($C_1$-$C_6$)-alkylene-O—($C_1$-$C_6$)-alkyl, —Si[($C_1$-$C_4$)-alkyl]$_3$ or —($C_4$-$C_{15}$)-Het, where alkyl, alkylene and cycloalkyl are each unsubstituted or mono-, di- or trisubstituted independently by —($C_1$-$C_4$)-alkyl, OH, —($C_3$-$C_6$)-cycloalkyl, —O—($C_1$-$C_6$)-alkyl or —O—($C_3$-$C_6$)-cycloalkyl, where all or some of the hydrogen atoms in alkyl or cycloalkyl may be replaced by fluorine, with the proviso that one R1, R2, R3, R4 or R5 is —$SF_5$, R9 is a hydrogen atom, —($C_1$-$C_6$)-alkyl or —($C_3$-$C_6$)-cycloalkyl, where all or some of the hydrogen atoms in alkyl or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments are a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

4. A compound as claimed in claim 1, where

Ar is a fused benzene ring, where the fused ring is unsubstituted or mono- or disubstituted independently by —O—($C_1$-$C_6$)-alkyl, —C(O)—N(R11)-R12 or halogen, Q1, Q2 and Q3 are the same and are each a hydrogen atom, R11 and R12 are each independently a hydrogen atom or —($C_1$-$C_6$)-alkyl, R1, R2, R3, R4 and R5 are the same or different and are each independently a hydrogen atom, —($C_1$-$C_6$)-alkyl, —O—($C_1$-$C_6$)-alkyl, halogen, —$SF_5$, —($C_0$-$C_4$)-alkylene-N(R21)-R22, —O—($C_1$-$C_6$)-alkylene-O—($C_1$-$C_6$)-alkyl or —($C_0$-$C_4$)-alkylene-N(R21)-C(O)—R22, with the proviso that one R1, R2, R3, R4 or R5 is —$SF_5$, R9 is a hydrogen atom, R21 and R22 are each independently a hydrogen atom, —($C_1$-$C_6$)-alkyl, —($C_3$-$C_6$)-cycloalkyl, $CF_3$ or —$SO_2CH_3$, where some or all of the hydrogen atoms in alkyl, alkylene or cycloalkyl may be replaced by fluorine, or R21 and R22 in the "N(R21)-R22" fragment are a ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl.

5. A compound as claimed in claim 1, selected from:

2-(1-imino-1,3-dihydroisoindol-2-yl)-1-(3-pentafluorosulfanylphenyl)ethanone as the hydrobromide, N-methyl-2-[2-(3-dimethylamino-5-pentafluorosulfanylphenyl)-2-oxoethyl]-6-ethoxy-3-imino-2,3-dihydro-1H-isoindole-5-carboxamide, N-methyl-6-ethoxy-3-imino-2-[2-(3-methylamino-5-pentafluorosulfanylphenyl)-2-oxoethyl]-2,3-dihydro-1H-isoindole-5-carboxamide, N-methyl-6-ethoxy-3-imino-2-{2-[3-pentafluorosulfanyl-5-(2,2,2-trifluoroacetylamino)phenyl]-2-oxoethyl}-2,3-dihydro-1H-isoindole-5-carboxamide, N-methyl-6-ethoxy-2-(2-{3-[ethyl-(2,2,2-trifluoroacetyl)amino]-5-pentafluorosulfanylphenyl}-2-oxoethyl)-3-imino-2,3-dihydro-1H-isoindole-5-carboxamide, N-methyl-6-ethoxy-2-[2-(3-ethylamino-5-pentafluorosulfanylphenyl)-2-oxo ethyl]-3-imino-2,3-dihydro-1H-isoindole-5-carboxamide as the hydrochloride, N-methyl-2-[2-(3-amino-5-pentafluorosulfanylphenyl)-2-oxoethyl]-6-ethoxy-3-imino-2,3-dihydro-1H-isoindole-5-carboxamide, N-methyl-2-[2-(3-acetylamino-5-pentafluorosulfanylphenyl)-2-oxoethyl)-6-ethoxy-3-imino-2,3-dihydro-1H-isoindole-5-carboxamide, 2-(5,6-diethoxy-7-fluoro-1-imino-1,3-dihydroisoindol-2-yl)-1-[3-methylamino-5-(pentamethylsulfanyl)phenyl]ethanone, N-methyl-6-ethoxy-3-imino-2-{2-[3-dimethanesulfonylamino-5-(pentafluorosulfanyl)phenyl]-2-oxoethyl}-2,3-dihydro-1H-isoindole-5-carboxamide, N-methyl-2-{2-[3-(acetylmethylamino)-5-(pentafluorosulfanyl)phenyl]-2-oxo ethyl}-6-ethoxy-3-imino-2,3-dihydro-1H-isoindole-5-carboxamide, N-[3-[2-(5,6-diethoxy-7-fluoro-1-imino-1,3-dihydroisoindol-2-yl)acetyl]-5-(pentafluorosulfanyl)phenyl]-N-methylacetamide, N-[3-[2-(5,6-diethoxy-7-fluoro-1-imino-1,3-dihydroisoindol-2-yl)acetyl]-5-(pentafluorosulfanyl)phenyl]isobutyramide, N-[3-[2-(5,6-diethoxy-7-fluoro-1-imino-1,3-dihydroisoindol-2-yl)acetyl]-5-(pentafluorosulfanyl)-phenyl]acetamide as the hydrobromide, N-[5-[2-(5,6-diethoxy-7-fluoro-1-imino-1,3-dihydroisoindol-2-yl)acetyl]-4-methyl-2-(pentafluorosulfanyl)phenyl]acetamide, 1-[5-amino-2-methyl-4-(pentafluorosulfanyl)phenyl]-2-(5,6-diethoxy-7-fluoro-1-imino-1,3-dihydroisoindol-2-yl)ethanone, N-{3-[2-(5,6-diethoxy-7-fluoro-1-imino-1,3-dihydroisoindol-2-yl)acetyl]-5-(pentafluorosulfanylphenyl}-3,3-dimethylbutyramide, 1-{3-[2-(5,6-diethoxy-7-fluoro-1-imino-1,3-dihydroisoindol-2-yl)acetyl]-5-pentafluorosulfanylphenyl}pyrrolidine-2,5-dione, 1-[2-amino-4-(pentafluorosulfanyl)phenyl]-2-(5,6-diethoxy-7-fluoro-1-imino-1,3-dihydroisoindol-2-yl)ethanone, 1-[2-amino-5-bromo-4-(pentafluorosulfanyl)phenyl]-2-(5,6-diethoxy-7-fluoro-1-imino-1,3-dihydroisoindol-2-yl)ethanone, 2-(5,6-diethoxy-7-fluoro-1-imino-1,3-dihydroisoindol-2-yl)-1-[3-methoxy-5-(pentafluorosulfanyl)-phenyl]ethanone, N-[3-[2-(5,6-diethoxy-7-fluoro-1-imino-1,3-dihydroisoindol-2-yl)acetyl]-5-(pentafluorosulfanyl)phenyl]cyclobutanecarboxamide as the hydrochloride, N-[3-[2-(5,6-diethoxy-7-fluoro-1-imino-1,3-dihydroisoindol-2-yl)acetyl]-5-(pentafluorosulfanyl)-phenyl]cyclopropanecarboxamide as the hydrochloride, 2-(5,6-diethoxy-7-fluoro-1-imino-1,3-dihydroisoindol-2-yl)-1-[3-ethoxy-5-(pentafluorosulfanyl)phenyl]ethanone, N-methyl-6-ethoxy-3-imino-2-{2-[3-methoxy-5-(pentafluorosulfanyl)phenyl]-2-oxoethyl}-2,3-dihydro-1H-isoindole-5-carboxamide, 1-[3-bromo-5-(pentafluorosulfanyl)phenyl]-2-(5,6-diethoxy-7-fluoro-1-imino-1,3-dihydroisoindol-2-yl) ethanone, 1-[3-chloro-5-(pentafluorosulfanyl)phenyl]-2-(5,6-diethoxy-7-fluoro-1-imino-1,3-dihydroisoindol-2-yl) ethanone, 1-[2-bromo-4-(pentafluorosulfanyl)phenyl]-2-(5,6-diethoxy-7-fluoro-1-imino-1,3-dihydroisoindol-2-yl) ethanone, 1-[2-chloro-4-(pentafluorosulfanyl)phenyl]-2-(5,6-diethoxy-7-fluoro-1-imino-1,3-dihydroisoindol-2-yl) ethanone, 2-(5,6-diethoxy-7-fluoro-1-imino-1,3-dihydroisoindol-2-yl)-1-[3-morpholin-4-yl-5-(pentafluorosulfanyl)phenyl]ethanone or 2-(5,6-diethoxy-7-fluoro-1-imino-1,3-dihydroisoindol-2-yl)-1-[3-(2-methoxyethoxy)-5-(pentafluorosulfanyl)phenyl]ethanone as the hydrochloride.

6. A pharmaceutical composition comprising at least one compound as claimed in claim 1 and a pharmaceutically acceptable carrier.

7. A method for the treatment of a disorder associated with thromboses, embolisms, or hypercoagulability, the method comprising administering to a patient in need thereof an effective dose of a compound as claimed in claim 1, wherein the disorder is selected from myocardial infarction, angina pectoris, stroke, deep vein thrombosis, pulmonary embolism, restenosis following revascularization, angioplasty, rheumatoid arthritis, arthrosis, chronic obstructive pulmonary disease, stent implantations and bypass operations, or reduction of a risk of thrombosis following surgical procedures that involve blood contact with foreign surfaces.

8. A process for preparing a compound of formula I as claimed in claim 1, comprising a) reacting a compound of formula II

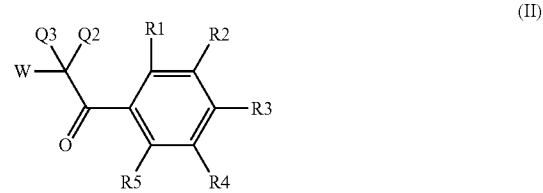

(II)

wherein R1, R2, R3, R4, R5, Q2 and Q3 are each as defined in claim 1 and W is chloride, bromide, mesylate or tosylate with a compound of formula III

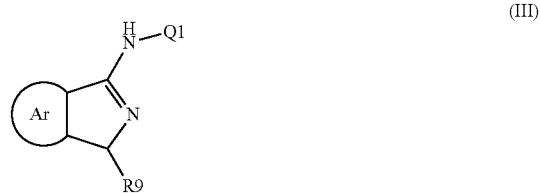

(III)

where Ar, R9 and Q1 are each as defined in claim 1, with or without addition of base, in a solvent, to give a compound of formula I, or b) reacting a compound of the formula VII

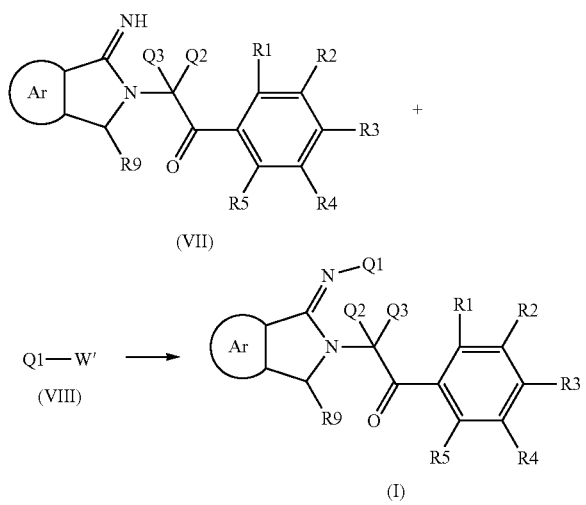

where R1, R2, R3, R4, R5, R9, Ar, Q1, Q2 and Q3 are each as defined in claim 1 with the compound Q1-W' where W' is chloride, bromide, mesylate, tosylate, methylsulfate or a similarly good leaving group, with or without addition of base, to give a compound of formula I, or c) either isolating the compound of the formula I prepared by process a) or b) in free form or releasing it from physiologically unacceptable salts or, in the case of presence of acidic or basic groups, converting them to physiologically acceptable salts, or d) separating a compound of the formula I prepared by process a) or b), or a suitable precursor of the formula I, which, owing to its chemical structure, occurs in enantiomeric or diastereomeric forms into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and detachment of the chiral auxiliary groups.

9. The method as claimed in claim 7, wherein the method reduces the risk of thrombosis following knee and hip joint operations or procedures involving contact of blood with foreign surfaces for dialysis patients and patients with indwelling catheters, or the method is directed to the treatment of a disorder selected from rheumatoid arthritis, arthrosis, and chronic obstructive pulmonary disease.

* * * * *